US010167303B2

(12) United States Patent
Murer et al.

(10) Patent No.: US 10,167,303 B2
(45) Date of Patent: Jan. 1, 2019

(54) IRIDIUM ORGANOMETALLIC COMPLEX CONTAINING A SUBSTITUTED DIBENZO[F,H]QUINOXALINE AND AN ELECTRONIC DEVICE HAVING AN EMITTING LAYER CONTAINING THE IRIDIUM COMPLEX

(71) Applicant: UDC IRELAND LIMITED, Dublin (IE)

(72) Inventors: Peter Murer, Oberwil (CH); Stephan Allenbach, Sisseln (CH); Gerhard Wagenblast, Wachenheim (DE); Christian Schildknecht, Fremont, CA (US); Christian Lennartz, Schifferstadt (DE)

(73) Assignee: UDC IRELAND LIMITED, Dublin (IE)

( * ) Notice: Subject to any disclaimer, the term of this patent is extended or adjusted under 35 U.S.C. 154(b) by 0 days.

(21) Appl. No.: 15/253,096

(22) Filed: Aug. 31, 2016

(65) Prior Publication Data
US 2017/0044194 A1    Feb. 16, 2017

Related U.S. Application Data

(62) Division of application No. 14/371,064, filed as application No. PCT/EP2013/050267 on Jan. 9, 2013, now Pat. No. 9,472,762.

(60) Provisional application No. 61/585,676, filed on Jan. 12, 2012.

(30) Foreign Application Priority Data

Jan. 12, 2012 (EP) .................................. 12150969

(51) Int. Cl.
| | | |
|---|---|---|
| C01G 55/00 | (2006.01) | |
| C07D 487/04 | (2006.01) | |
| C07F 15/00 | (2006.01) | |
| H01L 51/00 | (2006.01) | |
| H01L 51/05 | (2006.01) | |
| H01L 51/42 | (2006.01) | |
| H01L 51/50 | (2006.01) | |
| C09K 11/06 | (2006.01) | |

(52) U.S. Cl.
CPC .......... *C07F 15/0033* (2013.01); *C07F 15/00* (2013.01); *C09K 11/06* (2013.01); *H01L 51/009* (2013.01); *H01L 51/0035* (2013.01); *H01L 51/0036* (2013.01); *H01L 51/0083* (2013.01); *H01L 51/0085* (2013.01); *H01L 51/05* (2013.01); *H01L 51/42* (2013.01); *H01L 51/5012* (2013.01); *C09K 2211/1044* (2013.01); *C09K 2211/185* (2013.01); *H01L 51/4206* (2013.01); *H01L 51/5056* (2013.01); *H01L 51/5072* (2013.01)

(58) Field of Classification Search
CPC .............................. C01G 55/00; C07D 487/04

USPC ............................................ 423/22; 544/343
See application file for complete search history.

(56) References Cited

U.S. PATENT DOCUMENTS

| | | |
|---|---|---|
| 7,166,368 B2 | 1/2007 | Lecloux et al. |
| 8,471,248 B2 | 6/2013 | Schmidhalter et al. |
| 2003/0138662 A1 | 7/2003 | Li et al. |
| 2004/0001970 A1 | 1/2004 | Qiu et al. |
| 2008/0160345 A1 | 7/2008 | Inoue et al. |
| 2009/0283757 A1 | 11/2009 | Seo et al. |
| 2009/0322217 A1 | 12/2009 | Inoue et al. |
| 2010/0001638 A1 | 1/2010 | Kawakami et al. |
| 2010/0060154 A1 | 3/2010 | Nomura et al. |
| 2010/0060155 A1 | 3/2010 | Seo et al. |
| 2010/0076201 A1 | 3/2010 | Suzuki et al. |
| 2010/0096981 A1 | 4/2010 | Seo et al. |
| 2010/0156957 A1 | 6/2010 | Ogita et al. |
| 2011/0089407 A1 | 4/2011 | Schmidhalter et al. |
| 2011/0186825 A1 | 8/2011 | Egawa et al. |
| 2011/0198574 A1 | 8/2011 | Egawa et al. |
| 2011/0210316 A1 | 9/2011 | Kadoma et al. |
| 2011/0215714 A1 | 9/2011 | Seo et al. |
| 2011/0284835 A1 | 11/2011 | Osaka et al. |
| 2015/0005497 A1* | 1/2015 | Murer .................. C07F 15/0033 544/225 |

FOREIGN PATENT DOCUMENTS

| | | |
|---|---|---|
| EP | 1939208 | 7/2008 |
| EP | 2363398 | 9/2011 |
| JP | 2005298483 | 10/2005 |

(Continued)

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Zhiwei Liu, et al., "Red phosphorescent iridium complex containing carbazole-functionalized b-Diketonate for highly efficient nondoped organic light-emitting diodes", Advanced Functional Materials, vol. 16, 2006, pp. 1441-1448.
Jiun-Pey Duan, et al., "New iridium complexes as highly efficient orange-red emitters in organic light-emitting diodes". Advanced Materials, vol. 15, No. 3, Feb. 5, 2003, pp. 224-228.
International Search Report dated Mar. 7, 2013 in PCT/EP2013/050267.

*Primary Examiner* — Douglas M Willis
(74) *Attorney, Agent, or Firm* — Riverside Law LLP

(57) ABSTRACT

Iridium organometallic complexes containing a substituted dibenzo[f,h]quinoxaline having the formula

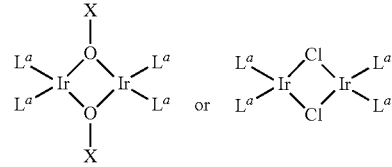

are provided. These compounds are useful as orange or red emitting components of a light emitting layer in an electronic device.

13 Claims, 1 Drawing Sheet

(56) References Cited

FOREIGN PATENT DOCUMENTS

| | | |
|---|---|---|
| JP | 2006241124 | 9/2006 |
| KR | 1020060036670 | 5/2006 |
| KR | 1020060079625 | 7/2006 |
| WO | 03058667 | 7/2003 |
| WO | 2005019373 | 3/2005 |
| WO | 2005049762 | 6/2005 |
| WO | 2006000544 | 1/2006 |
| WO | 2006056418 | 6/2006 |
| WO | 2006097419 | 9/2006 |
| WO | 2006100298 | 9/2006 |
| WO | 2005113704 | 12/2006 |
| WO | 2007115970 | 10/2007 |
| WO | 2007115981 | 10/2007 |
| WO | 2008000727 | 1/2008 |
| WO | 2008031743 | 3/2008 |
| WO | 2008034758 | 3/2008 |
| WO | 2008065975 | 6/2008 |
| WO | 2009003898 | 1/2009 |
| WO | 2009003919 | 1/2009 |
| WO | 2009069535 | 6/2009 |
| WO | 2009100991 | 8/2009 |
| WO | 2009157498 | 12/2009 |
| WO | 2010002850 | 1/2010 |
| WO | 2010047707 | 4/2010 |
| WO | 2010145991 | 12/2010 |
| WO | 2012045710 | 4/2012 |

\* cited by examiner

IRIDIUM ORGANOMETALLIC COMPLEX CONTAINING A SUBSTITUTED DIBENZO[F,H]QUINOXALINE AND AN ELECTRONIC DEVICE HAVING AN EMITTING LAYER CONTAINING THE IRIDIUM COMPLEX

CROSS-REFERENCE TO RELATED APPLICATIONS

The present application is a divisional of U.S. patent application Ser. No. 14/371,064, filed on Jul. 8, 2014, now allowed, which is a 35 U.S.C. § 371 national stage patent application of International Patent Application No. PCT/EP2013/050267, filed on Jan. 9, 2013, and which claims priority to U.S. Provisional Application No. 61/585,676, filed on Jan. 12, 2012, and European Application No. 12150969.9, filed on Jan. 12, 2012, all of which applications are incorporated by reference herein in their entireties.

BACKGROUND OF THE INVENTION

Field of the Invention

This invention relates to electroluminescent metal complexes with dibenzo[f,h]quinoxalines, a process for their preparation, electronic devices comprising the metal complexes and their use in electronic devices, especially organic light emitting diodes (OLEDs). The metal complexes with dibenzo[f,h]quinoxalines show high emission efficiency, excellent vaporiza-bility, thermal stability, processing stability, high charge carrier mobilities, low turn-on volt-age and high temperature stability of the emission color.

Discription of Related Art

JP2005298483 describes an iridium complex, such as, for example,

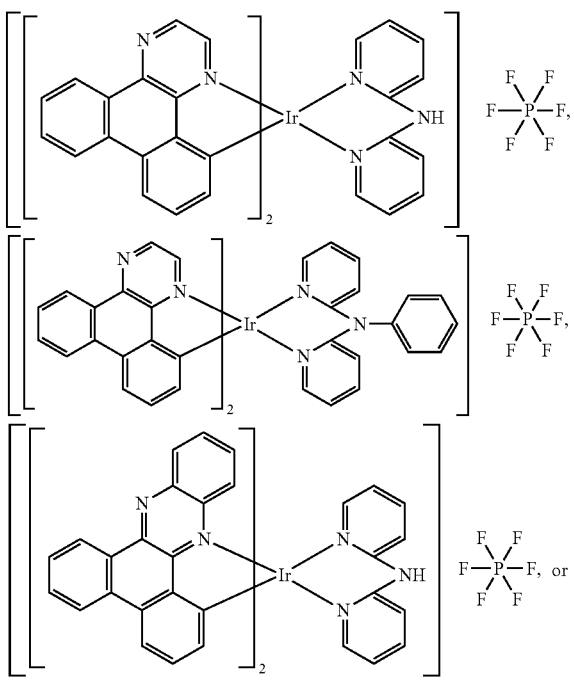

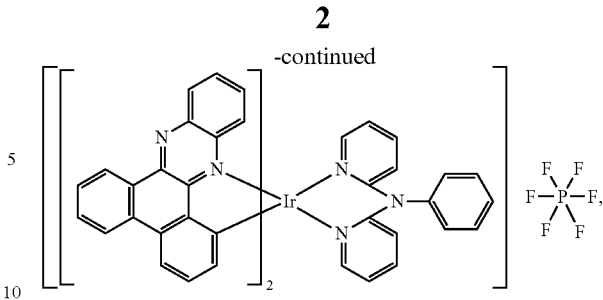

which can be used for the luminous element and is also suitable for an organic electroluminescent element material, an electrochemiluminescent (ECL) element material, a luminescence sensor, a photosensitizer, a display, etc., its preparation method and a luminous material.

KR20060079625 relates to phosphorescent red-emitting iridium complexes, such as, for example,

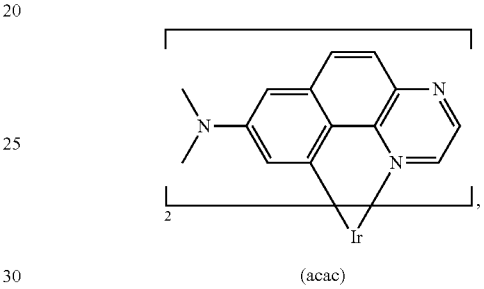

and organic electroluminescent device comprising same. Z. Liu et al, Adv. Funct. Mat. 2006, 16, 1441, describe the use of the complexes

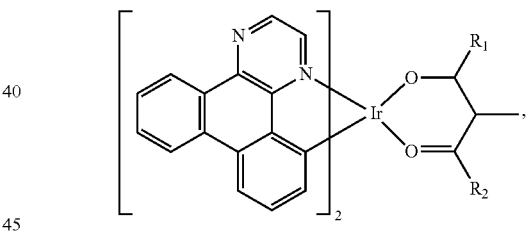

wherein $R^1$ is t-butyl and $R^2$ is

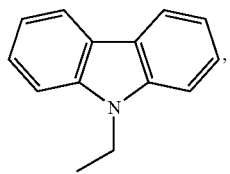

or $R^1$ is t-butyl and $R^2$ is

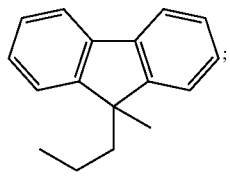 [SMILES: CCCC1(C)c2ccccc2-c2ccccc21]

for highly efficient non-doped organic light emitting diodes.

J.-P. Duan et al., Adv. Mat. 2003, 15, 224, describe the use of the complexes

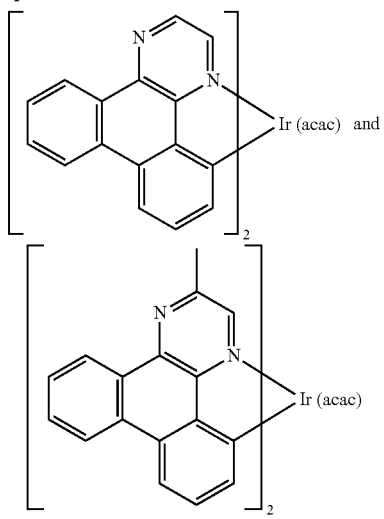

as orange-red emitters in an OLED.

KR20060036670 relates to phosphorescent iridium complexes and organic electroluminescent devices comprising the same. The following phosphorescent iridium complexes are explicitly disclosed

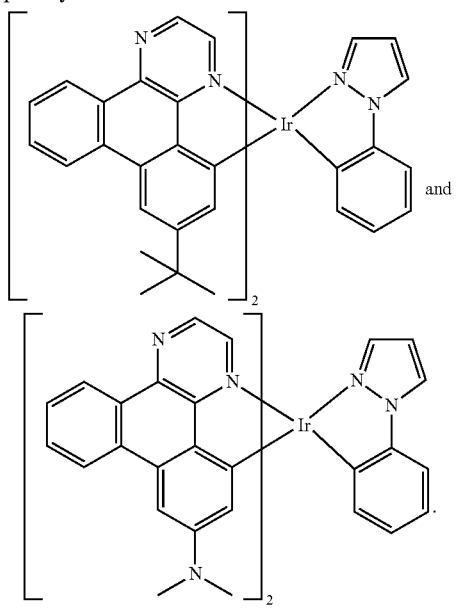

KR20060079625 relates to iridium complexes represented by the formula (1)

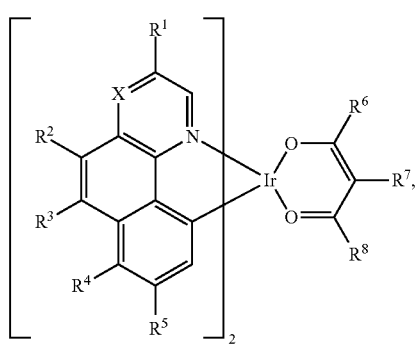

wherein $R_1$, $R_2$, $R_3$, $R_6$, $R_7$ and $R_8$ are independently H, a halogen atom, a carboxy group, an amino group, a cyano group, a nitro group, a $C_1$-$C_6$alkyl group, a $C_6$-$Ci_{18}$aryl group, a $C_1$-$C_6$alkoxy group or a $C_4$-$C_6$hetero ring containing a hetero atom such as S or N, or $R_2$ and $R_3$ can be fused to form an aromatic ring; $R_4$ and $R_5$ are independently H, a $C_1$-$C_6$ alkyl group, a $C_1$-$C_6$haloalkyl group, a $C_6$-$C_{18}$aryl group, a $C_4$-$C_{12}$hetero ring, an amino group substituted with an alkyl or aryl group, a $C_1$-$C_6$alkoxy group, a cyano group or a nitro group; and X is CH or N (claim 1), and an OLED device containing the metal complex of formula (1).

EP1939208A1 is directed to an organometallic complex having a structure represented by the general formula

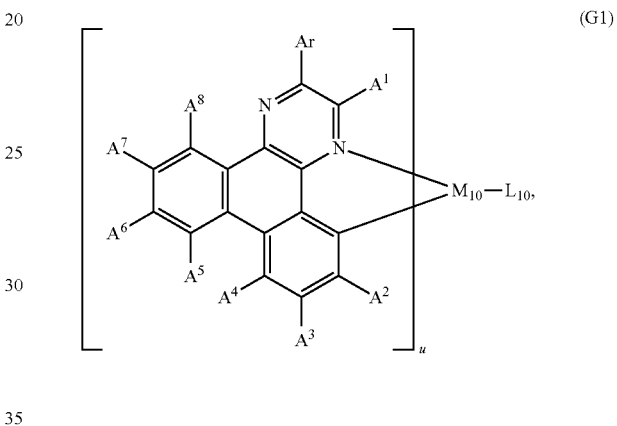

(G1)

wherein Ar represents an aryl group having 6 to 25 carbon atoms;

$A^1$ represents any one of hydrogen, an alkyl group having 1 to 4 carbon atoms, and an alkoxy group having 1 to 4 carbon atoms;

$A^2$ to $A^8$ each represent any one of hydrogen, an alkyl group having 1 to 4 carbon atoms, an alkoxy group having 1 to 4 carbon atoms, and a halogen group;

$M_{10}$ represents a metal of Group 9 elements and Group 10 elements;

$L_{10}$ represents a monoanionic ligand; and u is 2 when the metal is a Group 9 element, and u is 1 when the metal is a Group 10 element.

WO2009069535 relates to a light-emitting element comprising a light-emitting layer between a first electrode and a second electrode, wherein the light-emitting layer comprises a first organic compound having a hole-transporting property, a second organic compound having an electron-transporting property, and an organometallic complex, wherein a ligand of the organometallic complex has a dibenzo[th]quinoxaline skeleton, especially a 2-aryldibenzo[f,h]quinoxaline derivative, and wherein a central metal of the organometallic complex is a Group 9 or Group 10 element.

WO2009157498 relates to metal complexes of the formula

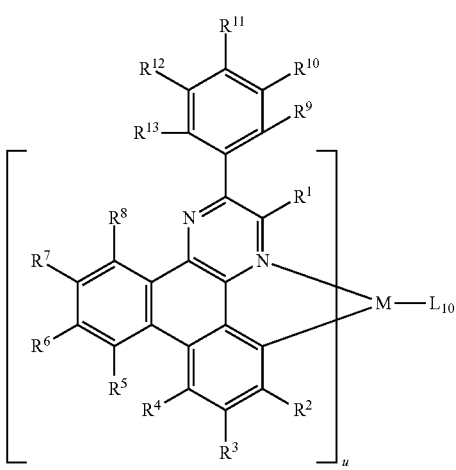

wherein R¹ to R¹³ represent any of hydrogen, an alkyl group having 1 to 4 carbon atoms, or an alkoxy group having 1 to 4 carbon atoms;
M represents a central metal selected from a Group 9 or Group 10 elements;
$L_{10}$ represents a monoanionic ligand; and u is 2 when the central metal is a Group 9 element or 1 when the central metal is a Group 10 element; and their use in light emitting devices.

WO2009100991 relates to metal complexes of the formula

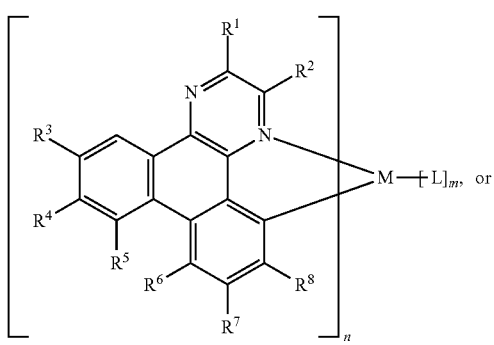

and their use in OLEDs. Among others compounds of formula

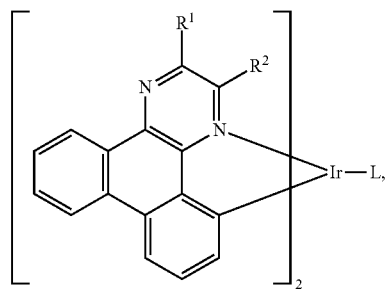

wherein R¹ is $C_2$-$C_{10}$alkyl, R² is H, or $CH_3$, and L is

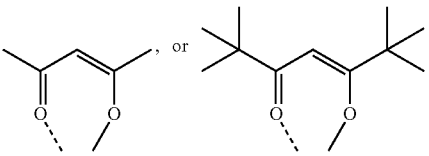

are preferred.

WO2005049762 relates to a light-emitting device comprising at least a substrate, an anode, a light-emitting layer and a cathode whereby the light-emitting layer contains an iridium complex $IrL_3$ and whereby at least two ligands L are a dibenzoquinoline. WO2005049762 relates in particular to the complexes Ir(dibenzo[f,h]quinoline)₂(pentane-2,4-dionate) and Ir(dibenzo[f,h]quinoline)₃ which emit light with a wavelength of $\lambda_{max}$=545 nm and $\lambda_{max}$=595 nm respectively:

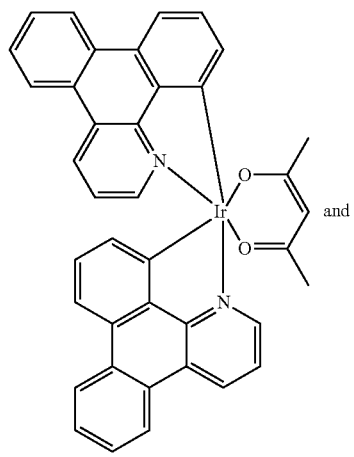

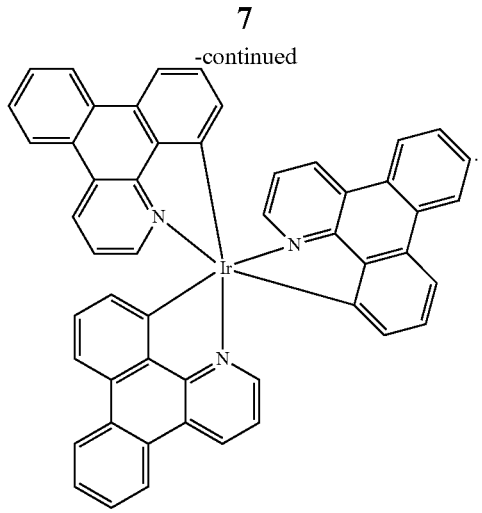

However, there is a continuing need for electroluminescent compounds, especially orange, or red emitters, having improved performance, such as for example, compounds having high emission efficiency, excellent vaporizability, thermal stability, processing stability, high charge carrier mobilities, low turn-on voltage and high temperature stability of the emission color.

BREIF SUMMARY OF THE INVENTION

Surprisingly, it was found that compounds of formula I, wherein $R^3$ and $R^8$ are $C_1$-$C_8$alkyl, show a narrower full width half maximum (FWHM) of the emission, such as, for example, by a narrowing of the green portion of the emission, in comparison to compounds of formula I known from the prior art, wherein $R^3$ and $R^8$ are H. Compounds of formula I, wherein $R^1$ is branched $C_1$-$C_8$ alkyl, show an even narrower FWHM of the emission. Due to the narrower FWHM of the emission the compounds of formula I show a more saturated orange to red emission, with deeper orange to red color index coordinates (CIE x,y), when used as emitter in an organic light emitting device (OLED), surprisingly by the introduction of alkyl groups at the appropriate positions alone. Moreover, alkyl substituents are particularly important because they offer a wide range of tunability in terms of evaporation temperature, solubility, energy levels, device efficiency etc. Moreover they are stable as functional groups chemically and in device operation when applied appropriately.

Accordingly the present invention is directed to compounds (metal complexes) of the formula

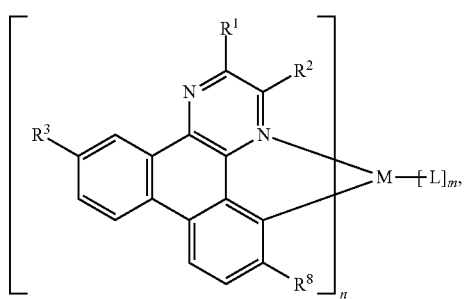

(I)

wherein
$R^1$ is H, $C_3$-$C_8$cycloalkyl, which is optionally substituted by $C_1$-$C_8$alkyl or $C_1$-$C_8$perfluoroalkyl; or $C_1$-$C_8$alkyl, or $R^1$ is a group of formula

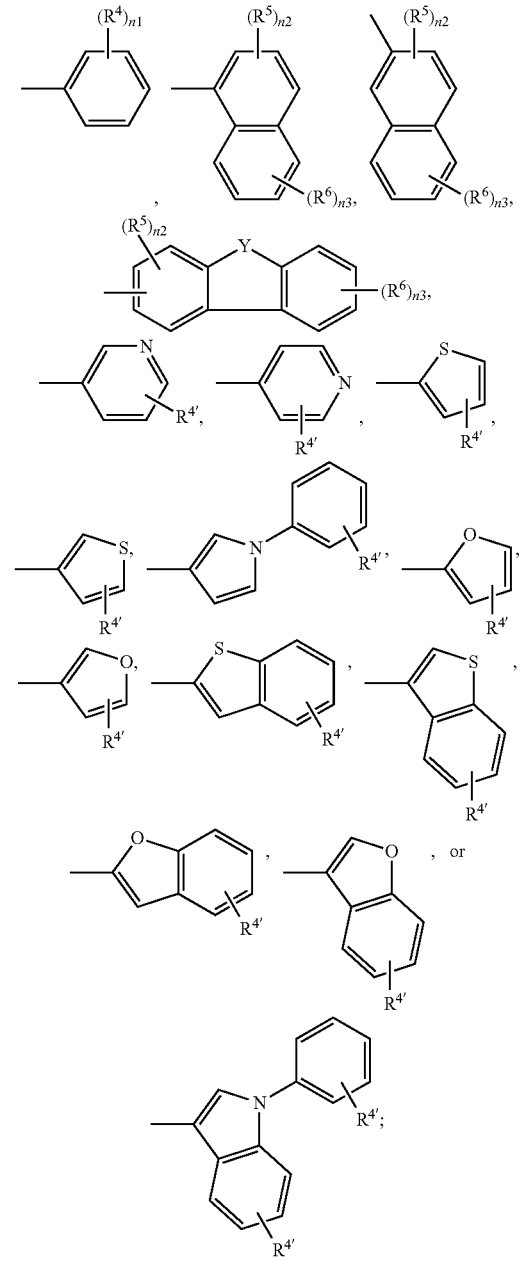

$R^2$ is H, or $C_1$-$C_8$alkyl, or
$R^1$ and $R^2$ together form a ring —(CH$_2$)$_3$—, or —(CH$_2$)$_4$—, which are optionally substituted by one, or two $C_1$-$C_8$alkyl and/or by one, or two $C_1$-$C_8$perfluoroalkyl;
$R^3$ and $R^8$ are independently of each other $C_1$-$C_8$alkyl, —Si($C_1$-$C_8$alkyl)$_3$, or $C_3$-$C_8$cycloalkyl;
n1 is 0, or an integer of 1 to 5, n2 is 0, or an integer of 1 to 3, n3 is 0, or an integer of 1 to 4,
Y is —O—, —S—, —NR$^{30}$—, or —CR$^{31}$R$^{32}$—;
$R^4$ is $C_1$-$C_8$alkyl, cyclohexyl, F, $C_1$-$C_8$perfluoroalkyl, or NR$^7$R$^9$, $R^{4'}$ is H, $C_1$-$C_8$alkyl, cyclohexyl, or $C_1$-$C_8$perfluoroalkyl, especially H, $C_1$-$C_8$alkyl, or $CF_3$, very especially H, or $C_1$-$C_8$alkyl, $R^5$ and $R^6$ are independently of each other $C_1$-$C_8$alkyl, or cyclohexyl; <CWU-Call number ="41"/>

$R^7$ and $R^9$ are independently of each other a group of formula

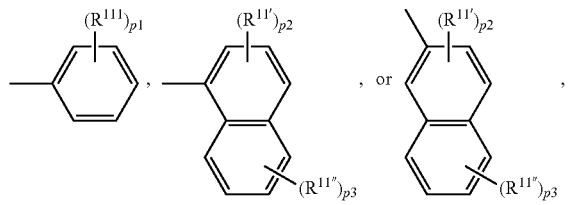

$R^{111}$, $R^{11'}$ and $R^{11''}$ are independently of each other $C_1$-$C_8$alkyl, or $C_1$-$C_8$alkoxy; or $R^7$ and $R^9$ together with the nitrogen atom to which they are bonded form a group of formula

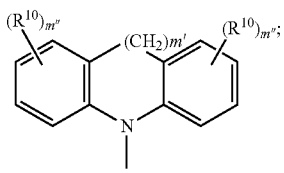

m' is 0, 1, or 2;

$R^{10}$ can be the same or different at each occurence and is $C_1$-$C_8$alkyl, or $C_3$-$C_8$cycloalkyl, $R^{30}$ is $C_1$-$C_{18}$alkyl; a group of formula

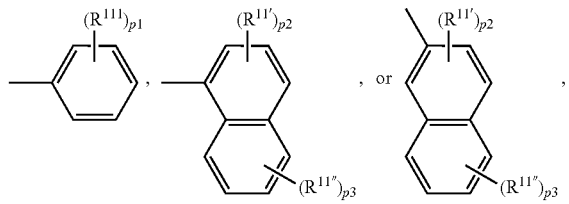

p1 is 0, or an integer of 1 to 3, p2 is 0, or an integer of 1 to 2, p3 is 0, or an integer of 1 to 2, $R^{31}$ and $R^{32}$ are independently of each other hydrogen, $C_1$-$C_{18}$alkyl, $C_7$-$C_{25}$arylalkyl, or a phenyl group, which optionally can be substituted one to three times with $C_1$-$C_8$alkyl and/or $C_1$-$C_8$alkoxy, m" can be the same or different at each occurence and is 0, 1, 2, or 3;

M is Pt, Pd, Rh, Ir, or Re,

L is a mono-, or bi-dentate ligand, if L is a monodentate ligand, m is 0, or 2, and n is 1, or 2, if M is Pd, or Pt, m is 0,2, or 4, and n is 1, 2, or 3, if M is Rh, Ir or Re, if L is a bidentate ligand, m is 0, or 1, and n is 1, or 2, if M is Pd, or Pt, m is 0,1, or 2, and n is 1,2, or 3, if M is Rh, Ir or Re.

The compounds of the present invention are preferably orange, or red emitters having a $\lambda_{max}$ above about 580 nm, especially above about 610 nm and very especially above about 615 nm. The dibenzo[f,h] quinoxaline compound or compounds should have a colour coordinate (CIE x,y) of between about (0.62, 0.38) and about (0.68, 0.32), especially a colour coordinate of between about (0.63, 0.37) and about (0.68, 0.32), very especially a colour coordinate of between about (0.64, 0.36) and about (0.68, 0.32).

The metal complexes with dibenzo[f,h]quinoxalines show high emission efficiency, excellent vaporizability, thermal stability, processing stability, high charge carrier mobilities, low turn-on voltage and high temperature stability of the emission color.

DETAILED DESCRIPTION OF THE DRAWINGS

Figure 1:
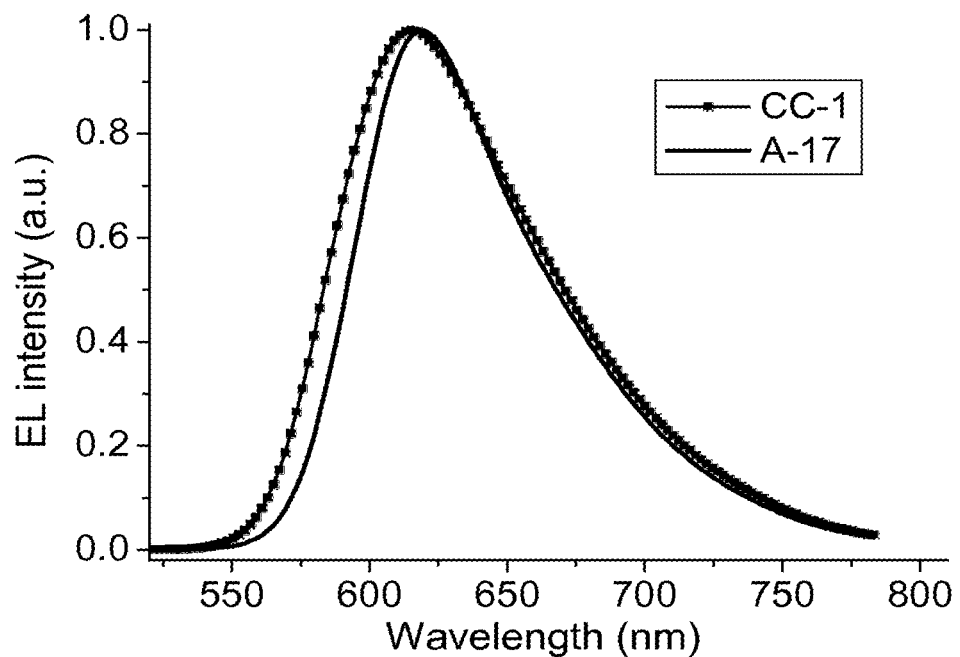
FIG. 1 provides a plot of the EL intensity of compounds CC-1 and A-17 as a function of wavelength.

According to the present invention the metal complex comprise at least a dibenzo[f,h]-quinoxaline ligand, i.e. it may comprise two or three dibenzo[f,h] quinoxaline ligands. The term "ligand" is intended to mean a molecule, ion, or atom that is attached to the coordination sphere of a metallic ion. The term "complex", when used as a noun, is intended to mean a compound having at least one metallic ion and at least one ligand. The term "group" is intended to mean a part of a compound, such a substituent in an organic compound or a ligand in a complex. The term "facial" is intended to mean one isomer of a complex, $Ma_3b_3$, having octahedral geometry, in which the three "a" groups are all adjacent, i.e. at the corners of one triangular face of the octahedron. The term "meridional" is intended to mean one isomer of a complex, $Ma_3b_3$, having octahedral geometry, in which the three "a" groups occupy three positions such that two are trans to each other, i.e. the three "a" groups sit in three coplanar positions, forming an arc across the coordination sphere that can be thought of as a meridion. The phrase "adjacent to" when used to refer to layers in a device, does not necessarily mean that one layer is immediately next to another layer.

The metal complexes of the present invention are characterized in that at least one ligand is derived from a dibenzo[f,h]quinoxaline compound. Suitable dibenzo[f,h] quinoxalines, or intermediates thereof, are known or can be produced according to known procedures. The synthesis of suitable dibenzo[f, h]quinoxaline and intermediates thereof is, for example, described in J.-P. Duan et al., Adv. Mat. 2003, 15, 224, WO2006/097419 and WO2008031743A1, as well as the references cited therein.

The compounds have preferably a structure (Va), (Vb), (Vc), (VIa), (VIb), or (VIc) below:

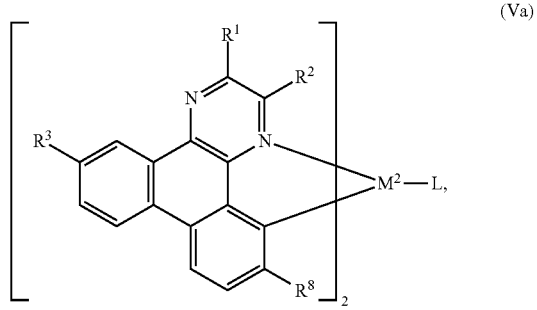

$R^1$, $R^2$, $R^3$ and $R^8$ are as defined above. More preferred are compounds of formula (Va), (Vb), (Vc), (VIa), (VIb), or (VIc), wherein $R^2$ is H.

The metal M is selected from Ir, Rh and Re as well as Pt and Pd, wherein Pt and Ir are preferred and Ir is most preferred.

In a preferred embodiment $R^1$ is $C_3$-$C_8$cycloalkyl, which is optionally substituted by one, or two $C_1$-$C_8$alkyl and/or by one, or two $C_1$-$C_8$perfluoroalkyl; or $C_1$-$C_8$alkyl, or $R^1$ and $R^2$together form a ring —$(CH_2)_3$—, or —$(CH_2)_4$—, which are optionally substituted by one, or two $C_1$-$C_8$alkyl and/or by one, or two $C_1$-$C_8$perfluoroalkyl. $R^2$ is preferably H. More preferred, $R^1$ is $C_3$-$C_8$cycloalkyl, or $C_1$-$C_8$alkyl, $R^2$ is H; or $R^1$ and $R^2$together form a ring —$(CH_2)_4$—. Most preferred $R^1$ is $C_3$-$C_8$cycloalkyl, or $C_1$-$C_5$alkyl, such as, for example, methyl, ethyl, iso-butyl, tert-butyl, or neopentyl. $R^2$ is preferably H.

In another preferred embodiment $R^1$ is a group of formula especially wherein
$M^2$ is Rh, Ir or Re,
$M^4$ is Pd, or Pt,
L is a bidentate ligand, and
L''' is a monodentate ligand, and -continued

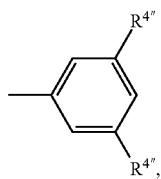

even more especially

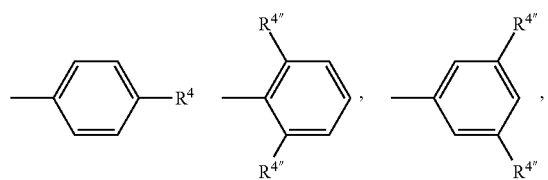

very especially

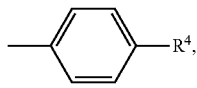

R⁴ is H, C₁-C₈alkyl, cyclohexyl, F, C₁-C₈perfluoroalkyl, or NR⁷R⁹, especially C₁-C₈alkyl, CF₃, or NR⁷R⁹, even more especially CF₃, NR⁷R⁹, very especially NR⁷R⁹, R⁵ and R⁶ are independently of each other H, C₁-C₈alkyl, especially H, or C₁-C₈alkyl;

R⁴‴ is C₁-C₈alkyl, cyclohexyl, F, C₁-C₈perfluoroalkyl, NR⁷R⁹, especially C₁-C₈alkyl, or CF₃, NR⁷R⁹, even more especially C₁-C₈alkyl, or CF₃, very especially C₁-C₈alkyl, R⁷ and R⁹ are independently of each other

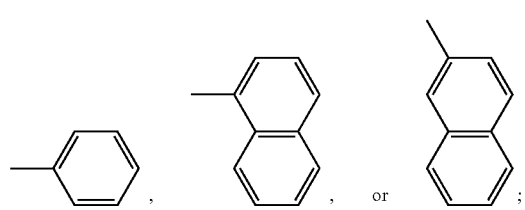

or

R⁷ and R⁹ together with the nitrogen atom to which they are bonded form a group of formula

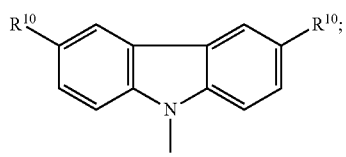

R¹⁰ is H, or C₁-C₈alkyl, and R² is H.

In another preferred embodiment R¹ is a group of formula

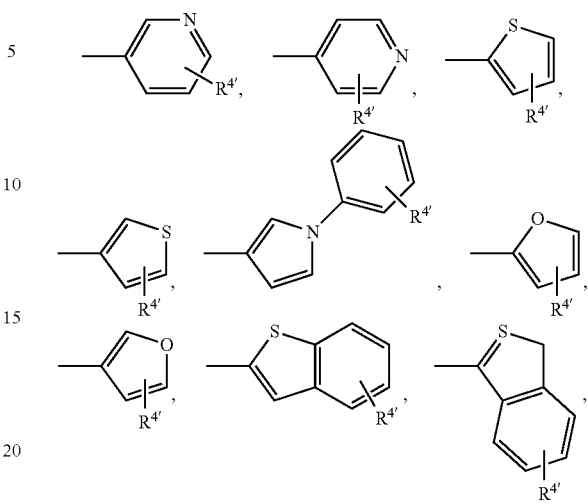

especially

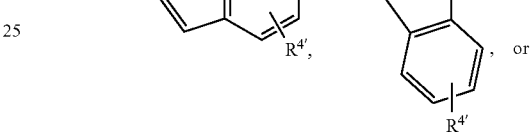

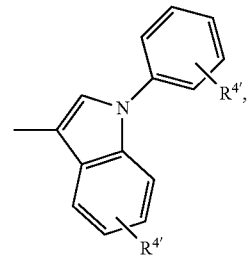

more especially

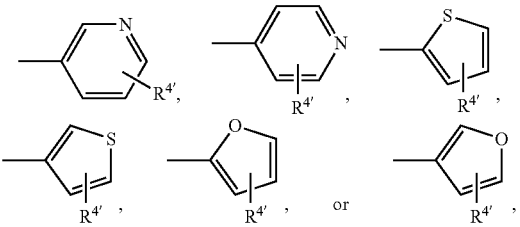

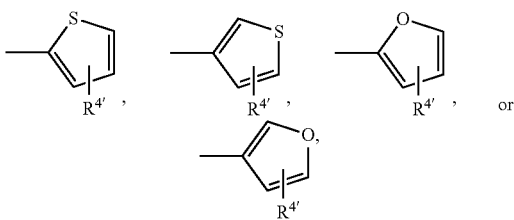

wherein R⁴' is H, C₁-C₈alkyl, cyclohexyl, or C₁-C₈perfluoroalkyl, especially H, C₁-C₈alkyl, or CF₃, very especially H, or C₁-C₈alkyl.

If $R^1$ is a group of formula

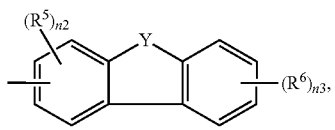

groups of formula

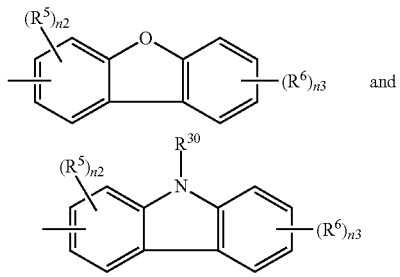

are preferred and groups of formula

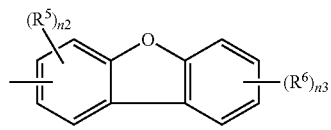

are even more preferred.

For the above described preferred embodiments for $R^1$ the following preferences for $R^2$, $R^3$, $R^8$, L and M apply:

M is preferably Pt and Ir, more preferably Ir.

L is preferably a group of formula

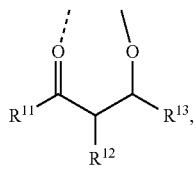

more preferably

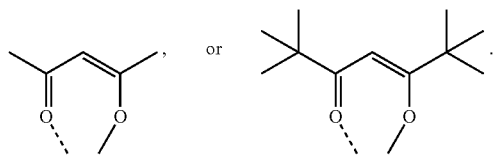

$R^2$ is preferably H.

$R^3$ and $R^8$ are preferably $C_1$-$C_8$alkyl, $Si(C_1$-$C_4$alkyl$)_3$, or $C_3$-$C_6$cycloalkyl.

If $R^3$ and $R^8$ represent a cycloalkyl group, they are preferably cyclopropyl, cyclobutyl, or cyclopentyl.

If $R^3$ and $R^8$ represent a trialkylsilyl group, they are preferably trimethyl silyl.

If $R^3$ and $R^8$ represent a $C_1$-$C_8$alkyl group, they are preferably $C_1$-$C_5$alkyl, especially methyl, ethyl, iso-butyl, or neopentyl.

Monodentate ligands are preferably monoanionic. Such ligands can have O or S as coordinating atoms, with coordinating groups such as alkoxide, carboxylate, thiocarboxylate, dithiocarboxylate, sulfonate, thiolate, carbamate, dithiocarbamate, thiocarbazone anions, sulfonamide anions, and the like. In some cases, ligands such as β-enolates can act as monodentate ligands. The monodentate ligand can also be a coordinating anion such as halide, nitrate, sulfate, hexahaloantimonate, and the like. Examples of suitable monodentate ligands are shown below:

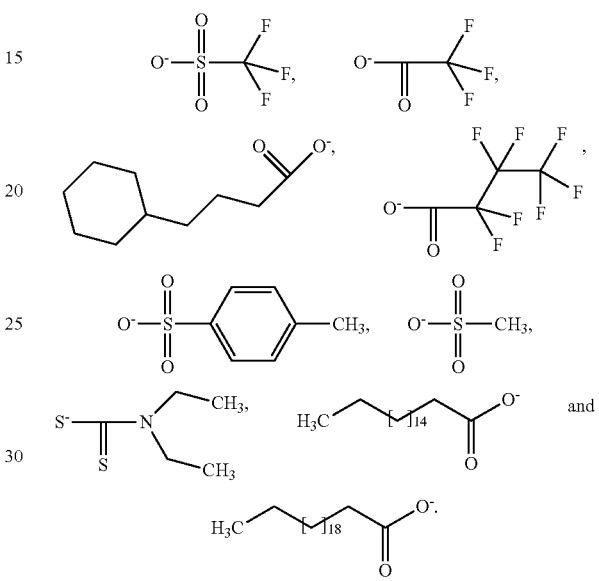

The monodentate ligands are generally available commercially.

In a preferred embodiment of the present invention the ligand is a (monoanionic) bidentate ligand. In general these ligands have N, O, P, or S as coordinating atoms and form 5- or 6 membered rings when coordinated to the iridium. Suitable coordinating groups include amino, imino, amido, alkoxide, carboxylate, phosphino, thiolate, and the like. Examples of suitable parent compounds for these ligands include p-dicarbonyls (β-enolate ligands), and their N and S analogs; amino carboxylic acids (aminocarboxylate ligands); pyridine carboxylic acids (iminocarboxylate ligands); salicylic acid derivatives (salicylate ligands); hydroxyquinolines(hydroxyquinolinate ligands) and their S analogs; and diarylphosphinoalkanols (diarylphosphinoalkoxide ligands).

Examples of such bidentate ligands L are

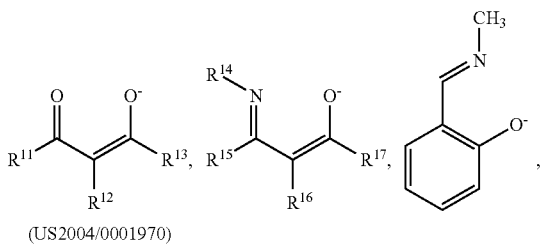

(US2004/0001970)

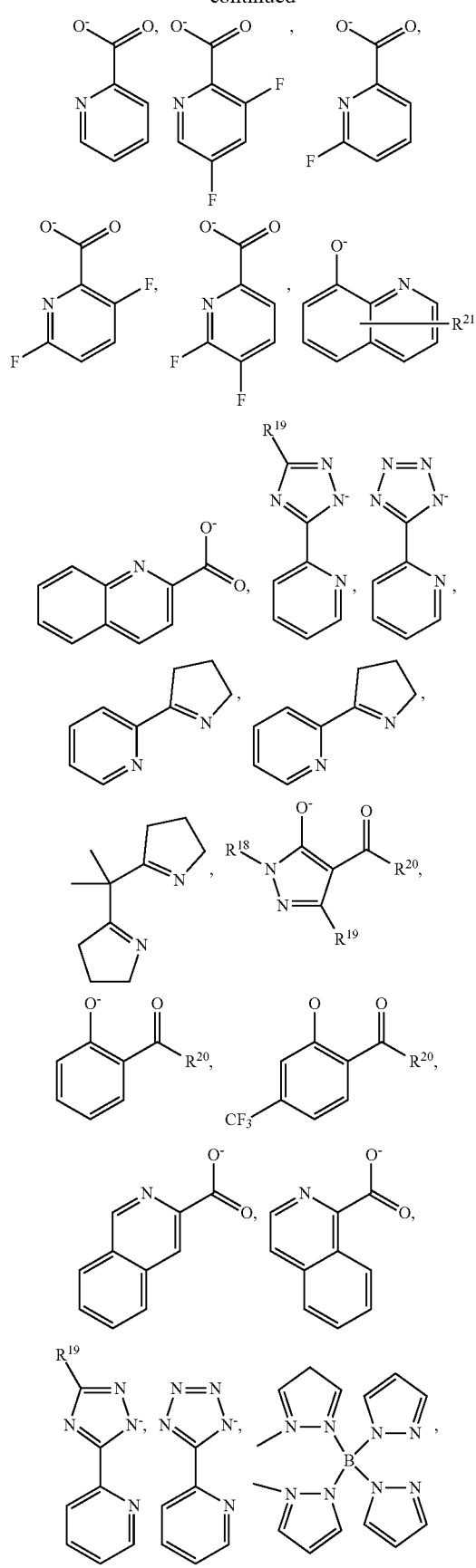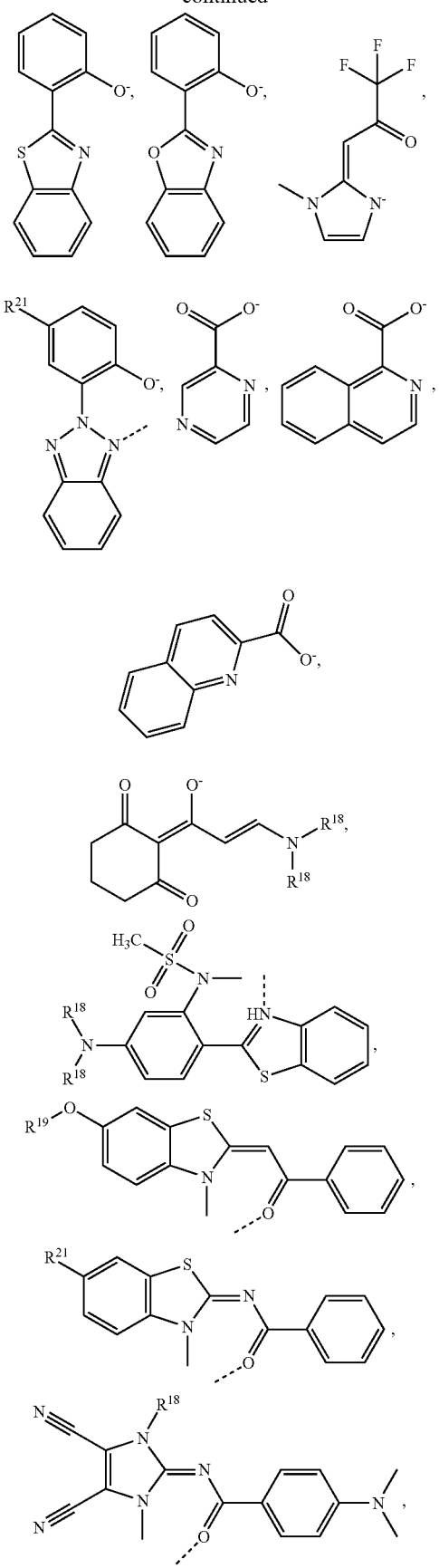

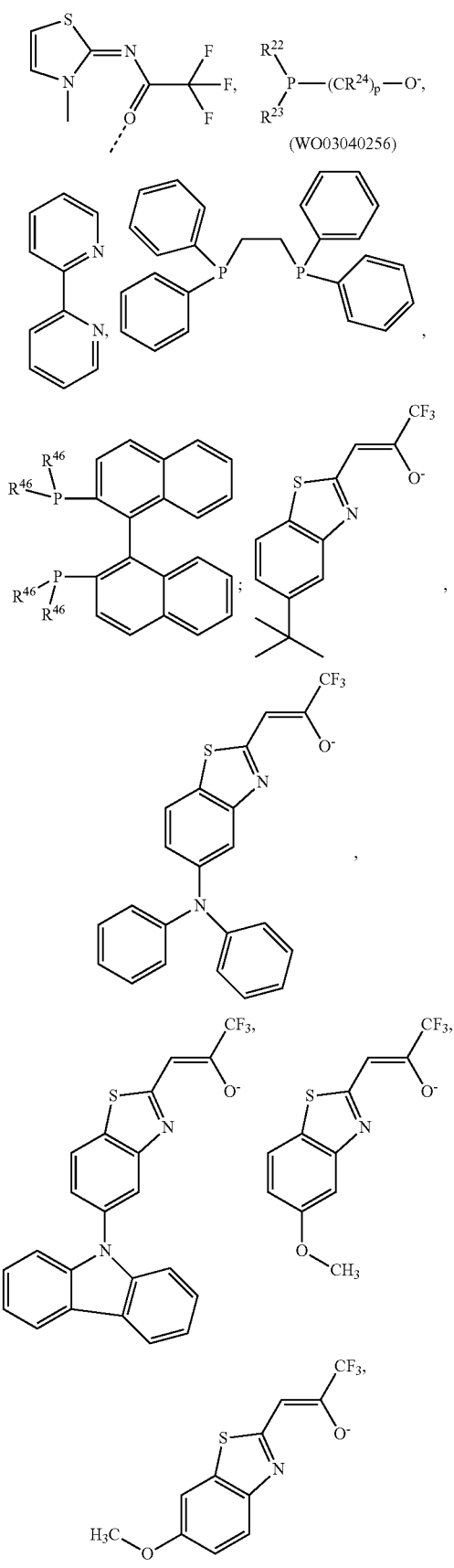

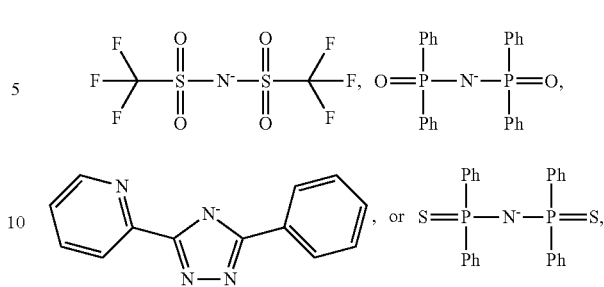

wherein R[11] and R[15] are independently of each other hydrogen, $C_1$-$C_8$alkyl, $CC_6$-$C_{18}$aryl, which can optionally be substituted by $C_1$-$C_8$alkyl; cyclopentyl, which can optionally be substituted by $C_1$-$C_8$alkyl, or phenyl; cyclohexyl, which can optionally be substituted by $C_1$-$C_8$alkyl, or phenyl; $C_2$-$C_{10}$heteroaryl, or $C_1$-$C_8$perfluoroalkyl, R[12] and R[16] are independently of each other hydrogen, $C_6$-$C_{18}$aryl, or $C_1$-$C_8$alkyl, or R[12] is a group of formula

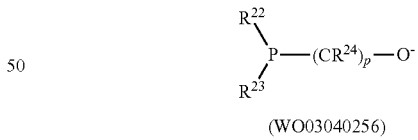

R[13] and R[17] are independently of each other hydrogen, $C_1$-$C_8$alkyl, $C_6$-$C_{18}$aryl, $C_2$-$C_{10}$heteroaryl, $C_1$-$C_8$perfluoroalkyl, or $C_1$-$C_8$alkoxy, and R[14] is $C_1$-$C_8$alkyl, $C_6$-$C_{10}$aryl, or $C_7$-$C_{11}$aralkyl, R[18] is $C_6$-$C_{10}$aryl, R[19] is $C_1$-$C_8$alkyl, $C_1$-$C_8$perfluoroalkyl, R[20] is $C_1$-$C_8$alkyl, or $C_6$-$C_{10}$aryl, R[21] is hydrogen, $C_1$-$C_8$alkyl, or $C_1$-$C_8$alkoxy, which may be partially or fully fluorinated, R[22] and R[23] are independently of each other $C_q(H+F)_{2q+1}$, or $C_6(H+F)_5$, R[24] can be the same or different at each occurrence and is selected from H, or $C_q(H+F)_{2q+1}$, q is an integer of 1 to 24, p is 2, or 3, and R[46] is $C_1$-$C_8$alkyl, $C_6$-$C_{18}$aryl, or $C_6$-$C_{18}$aryl, which is substituted by $C_1$-$C_8$alkyl.

Examples of suitable phosphino alkoxide ligands $$R^{22}\diagdown_{P}-(CR^{24})_p-O^-$$
$$R^{23}\diagup$$

(WO03040256)

are
listed below:
3-(diphenylphosphino)-1-oxypropane [dppO]
1,1-bis(trifluoromethyl)-2-(diphenylphosphino)-ethoxide [tfmdpeO].

Examples of particularly suitable compounds HL,

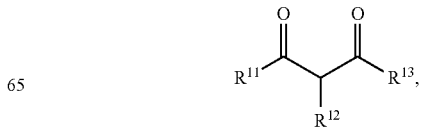

from which the ligands L are derived, include
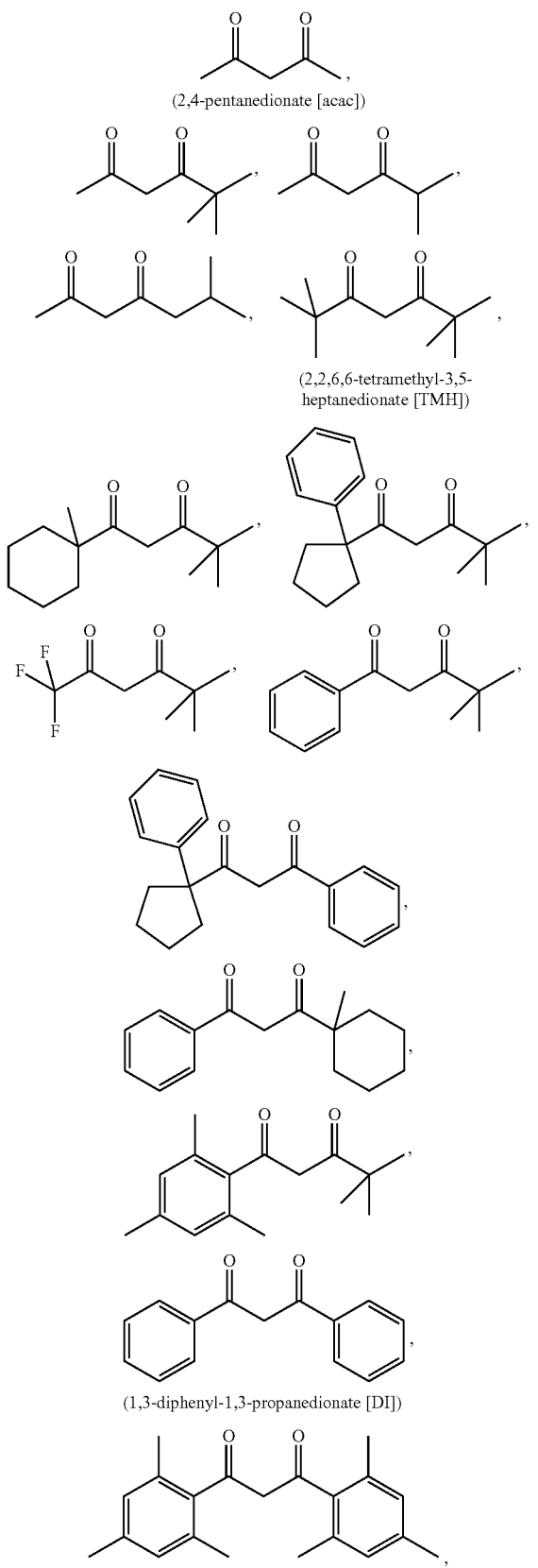
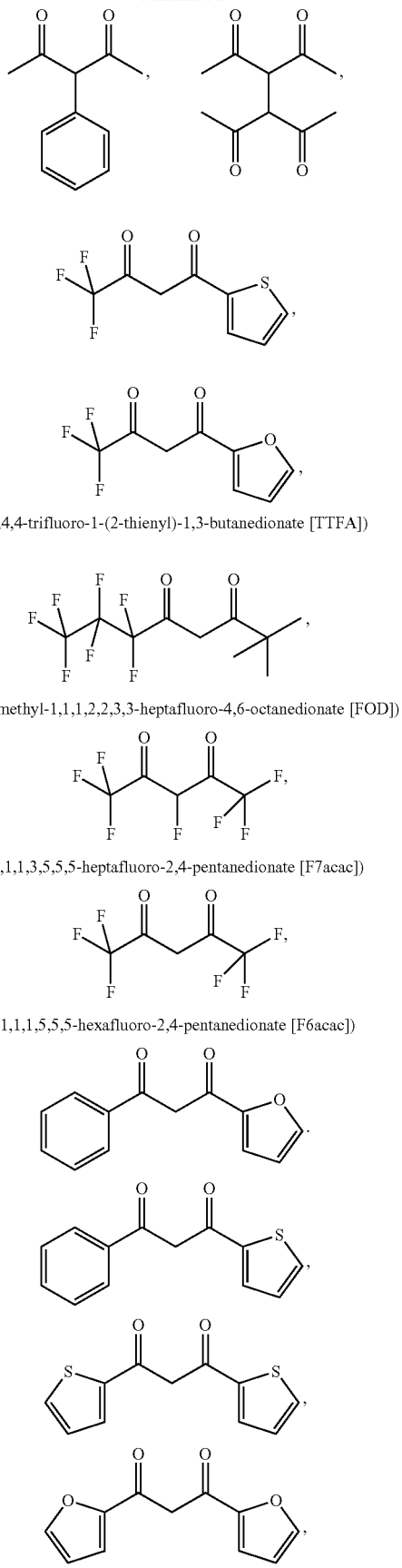

-continued

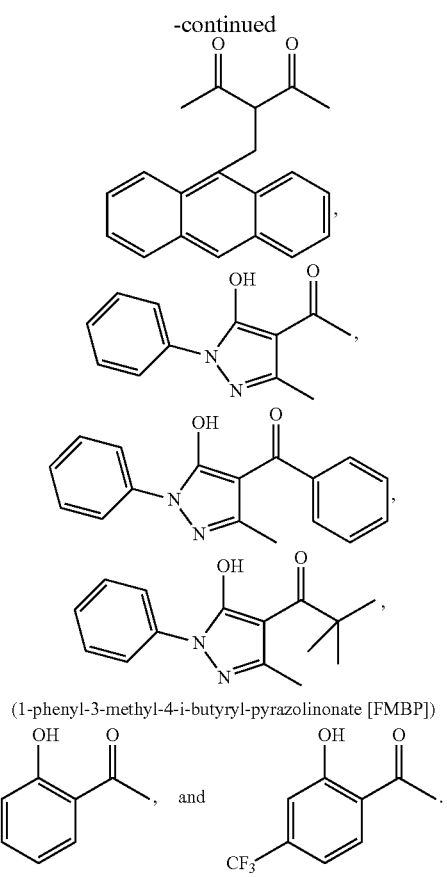

(1-phenyl-3-methyl-4-i-butyryl-pyrazolinonate [FMBP])

The hydroxyquinoline parent compounds, HL, can be substituted with groups such as alkyl or alkoxy groups which may be partially or fully fluorinated. In general, these compounds are commercially available. Examples of suitable hydroxyquinolinate ligands, L, include:

8-hydroxyquinolinate [8hq]
2-methyl-8-hydroxyquinolinate [Me-8hq]
10-hydroxybenzoquinolinate [10-hbq]

In a further embodiment of the present invention the bidentate ligand L is a ligand of formula wherein the ring A, represents an optionally substituted aryl group which can optionally contain heteroatoms, the ring B, represents an optionally substituted nitrogen containing aryl group, which can optionally contain further heteroatoms, or the ring A may be taken with the ring B binding to the ring A to form a ring.

The preferred ring A includes a phenyl group, a substituted phenyl group, a naphthyl group, a substituted naphthyl group, a furyl group, a substituted furyl group, a benzofuryl group, a substituted benzofuryl group, a thienyl group, a substituted thienyl group, a benzothienyl group, a substituted benzothienyl group, and the like. The substitutent on the substituted phenyl group, substituted naphthyl group, substituted furyl group, substituted benzofuryl group, substituted thienyl group, and substituted benzothienyl group include $C_1$-$C_{24}$alkyl groups, $C_2$-$C_{24}$alkenyl groups, $C_2$-$C_{24}$alkynyl groups, aryl groups, heteroaryl groups, $C_1$-$C_{24}$alkoxy groups, $C_1$-$C_{24}$alkylthio groups, a cyano group, $C_2$-$C_{24}$acyl groups, $C_1$-$C_{24}$alkyloxycarbonyl groups, a nitro group, halogen atoms, alkylenedioxy groups, and the like.

In said embodiment the bidentate ligand is preferably a group of formula wherein $R^{211}$, $R^{212}$, $R^{213}$, $R^{214}$ are independently of each other hydrogen, $C_1$-$C_{24}$alkyl, $C_2$-$C_{24}$alkenyl, $C_2$-$C_{24}$alkynyl, aryl, heteroaryl, $C_1$-$C_{24}$alkoxy, $C_1$-$C_{24}$alkylthio, cyano, acyl, alkyloxycarbonyl, a nitro group, or a halogen atom; the ring A represents an optionally substituted aryl or heteroaryl group; or the ring A may be taken with the pyridyl group binding to the ring A to form a ring; the alkyl group, alkenyl group, alkynyl group, aryl group, heteroaryl group, alkoxy group, alkylthio group, acyl group, and alkyloxycarbonyl group represented by $R^{211}$, $R^{212}$, $R^{213}$, and $R^{214}$ may be substituted; or $R^{213}$ and $R^{214}$ or $R^{212}$ and $R^{213}$ are a group of formula

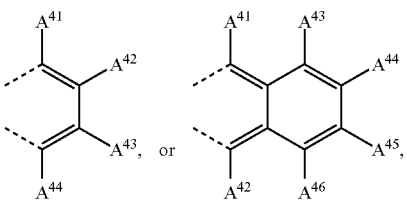

wherein $A^{41}$, $A^{42}$, $A^{43}$, $A^{44}$, $A^{45}$, and $A^{46}$ are as defined above.

Examples of preferred classes of such bidentate ligands L are compounds of the formula

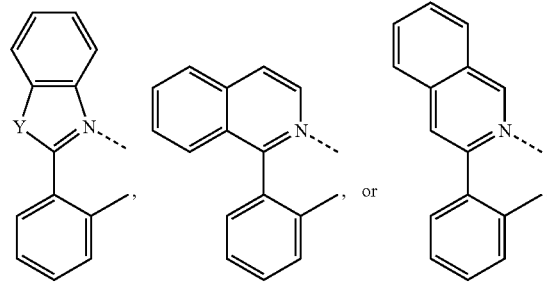

especially

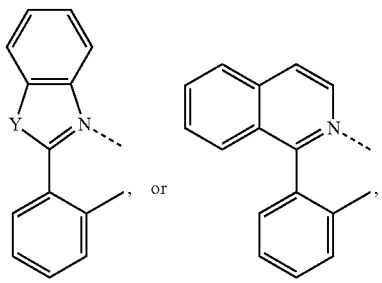

wherein Y is S, O, $NR^{200}$, wherein $R^{200}$ is $C_1$-$C_4$alkyl, $C_2$-$C_4$alkenyl, optionally substituted $C_6$-$C_{10}$-aryl, especially phenyl, —(CH2)$_r$—Ar, wherein Ar is an optionally substituted $C_6$-$C_{10}$aryl, especially

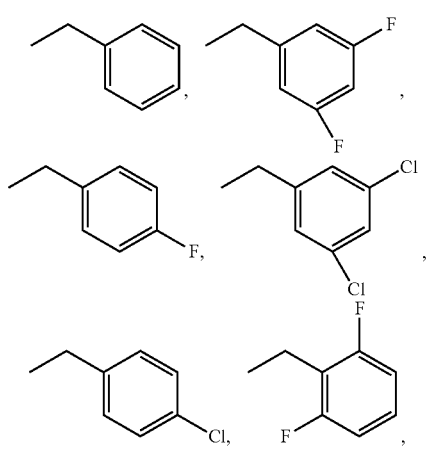

a group —(CH$_2$)$_r$—$X^{20}$, wherein r' is an integer of 1 to 5, $X^{20}$ is halogen, especially F, or Cl; hydroxy, cyano, —O—$C_1$-$C_4$alkyl, di($C_1$-$C_4$alkyl)amino, amino, or cyano; a group —(CH$_2$)$_r$OC(O)(CH$_2$)$_{r''}$-CH$_3$, wherein r is 1, or 2, and r" is 0, or 1;

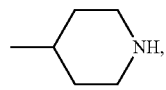

—NH-Ph, —C(O)CH$_3$, —CH$_2$—O—(CH$_2$)$_2$—Si(CH$_3$)$_3$, or

Another preferred class of ligands L is described in WO06/000544, of which the following can advantageously be used according to the present invention:

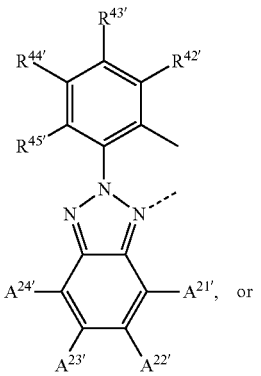 or 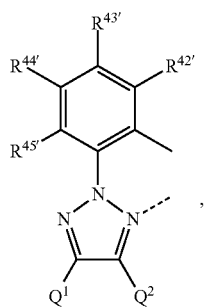, wherein
$Q^1$ and $Q^2$ are independently of each other hydrogen, $C_1$-$C_{24}$alkyl, or $C_6$-$C_{18}$aryl,
$A^{21'}$ is hydrogen,
$A^{22'}$ is hydrogen, or $C_6$-$C_{10}$aryl,
$A^{23'}$ is hydrogen, or $C_6$-$C_{10}$aryl,
$A^{24'}$ is hydrogen, or
$A^{23'}$ and $A^{24'}$, or $A^{23'}$ and $A^{24'}$ together form a group

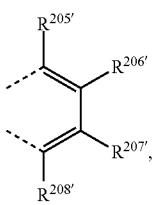

wherein $R^{205'}$, $R^{206'}$, $R^{207'}$ and $R^{208'}$ are independently of each other H, or $C_1$-$C_8$alkyl,
$R^{42'}$ is H, F, $C_1$-$C_4$alkyl, $C_1$-$C_8$alkoxy, or $C_1$-$C_4$perfluoroalkyl,
$R^{43'}$ is H, F, $C_1$-$C_4$alkyl, $C_1$-$C_8$alkoxy, $C_1$-$C_4$perfluoroalkyl, or $C_6$-$C_{10}$aryl,
$R^{44'}$ is H, F, $C_1$-$C_4$alkoxy, $C_1$-$C_8$alkoxy, or $C_1$-$C_4$perfluoroalkyl, and $R^{45'}$ is H, F, $C_1$-$C_4$alkyl, $C_1$-$C_8$alkoxy, or $C_1$-$C_4$ perfluoroalkyl.

Another preferred class of bidentate ligands L is a compound of formula

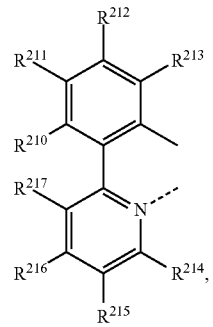

(5)

wherein $R^{214}$ is hydrogen, halogen, especially F, or Cl; $C_1$-$C_4$alkyl, $C_1$-$C_4$perfluoroalkyl, $C_1$-$C_4$alkoxy, or optionally substituted $C_6$-$C_{10}$aryl, especially phenyl, $R^{215}$ is hydrogen, halogen, especially F, or Cl; $C_1$-$C_4$ alkyl, $C_1$-$C_4$perfluoroalkyl, optionally substituted $C_6$-$C_{10}$aryl, especially phenyl, or optionally substituted $C_6$-$C_{10}$perfluoroaryl, especially $C_6F_5$, $R^{216}$ is hydrogen, $C_1$-$C_4$alkyl, $C_1$-$C_4$perfluoroalkyl, optionally substituted $C_6$-$C_{10}$aryl, especially phenyl, or optionally substituted $C_6$-$C_{10}$perfluoroaryl, especially $C_6F_5$, $R^{217}$ is hydrogen, halogen, especially F, or Cl; nitro, cyano, $C_1$-$C_4$alkyl, $C_1$-$C_4$perfluoroalkyl, $C_1$-$C_4$alkoxy, or optionally substituted $C_6$-$C_{10}$aryl, especially phenyl, $R^{210}$ is hydrogen, $R^{211}$ is hydrogen, halogen, especially F, or Cl; nitro, cyano, $C_1$-$C_4$alkyl, $C_1$-$C_4$alkoxy, $C_2$-$C_4$alkenyl, $C_1$-$C_4$perfluoroalkyl, —O-$C_1$-$C_4$perfluoroalkyl, tri($C_1$-$C_4$alkyl)silanyl, especially tri(methyl)silanyl, optionally substituted $C_6$-$C_{10}$aryl, especially phenyl, or optionally substituted $C_6$-$C_{10}$perfluoroaryl, especially $C_6F_5$, $R^{212}$ is hydrogen, halogen, especially F, or Cl; nitro, hydroxy, mercapto, amino, $C_1$-$C_4$alkyl, $C_2$-$C_4$alkenyl, $C_1$-$C_4$perfluoroalkyl, $C_1$-$C_4$alkoxy, —O-$C_1$-$C_4$perfluoroalkyl, —S-$C_1$-$C_4$alkyl, tri($C_1$-$C_4$alkyl)siloxanyl, optionally substituted —O-$C_6$-$C_{10}$aryl, especially phenoxy, cyclohexyl, optionally substituted $C_6$-$C_{10}$aryl, especially phenyl, or optionally substituted $C_6$-$C_{10}$perfluoroaryl, especially $C_6F_5$, and $R^{213}$ is hydrogen, nitro, cyano, $C_1$-$C_4$alkyl, $C_2$-$C_4$alkenyl, $C_1$-$C_4$perfluoroalkyl, —O -$C_1$-$C_4$perfluoroalkyl, tri($C_1$-$C_4$alky)silanyl, or optionally substituted $C_6$-$C_{10}$aryl, especially phenyl.

Specific examples of bidentate ligands L are the following compounds (X-1) to (X-57):

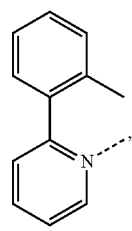

(X-1)

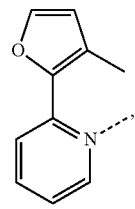

(X-2)

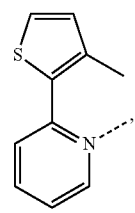

(X-3)

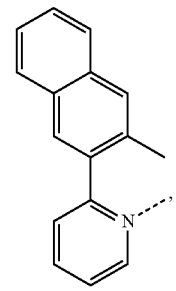

(X-4)

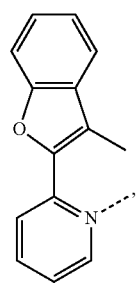

(X-5)

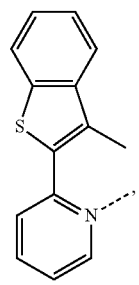

(X-6)

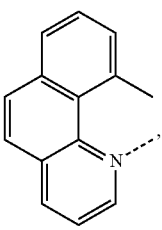

(X-7)

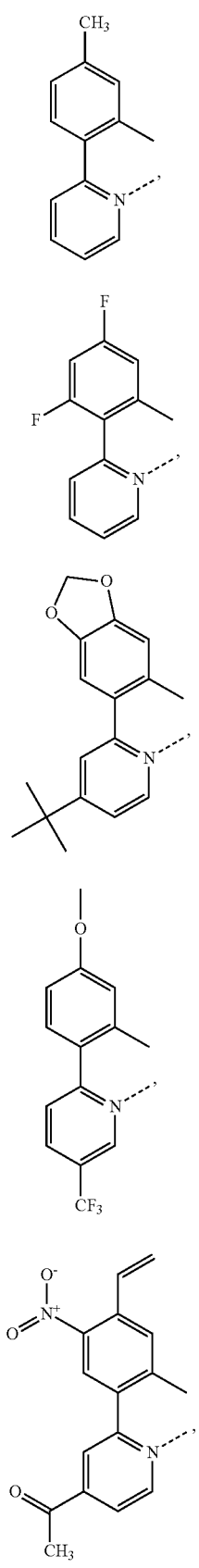
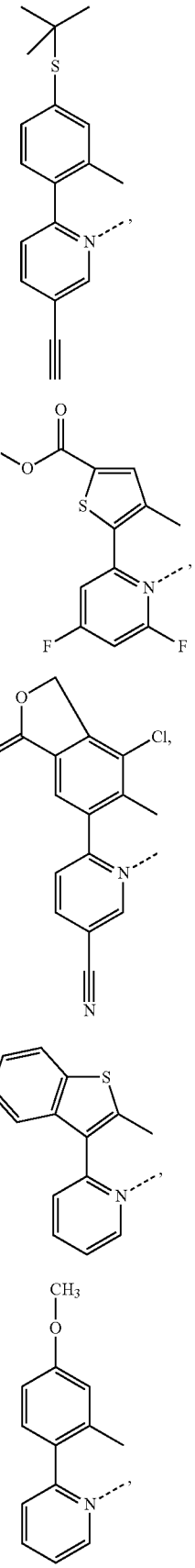

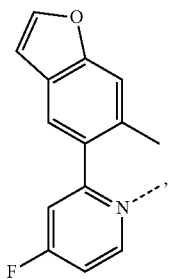
(X-18)
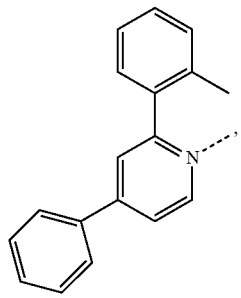
(X-19)
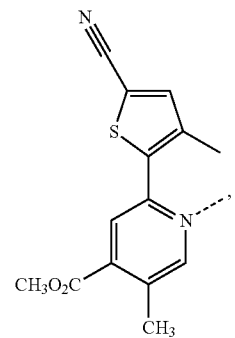
(X-20)
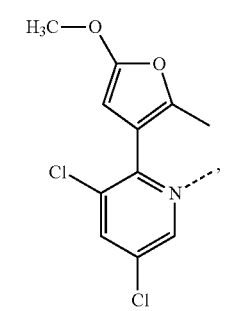
(X-21)
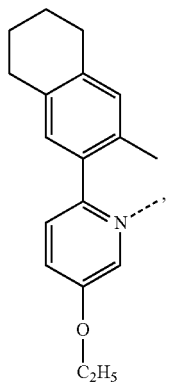
(X-22)
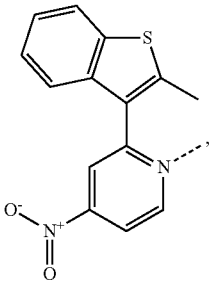
(X-23)
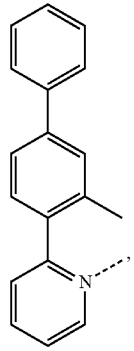
(X-24)
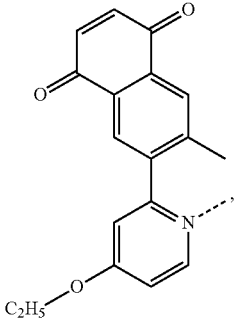
(X-25)
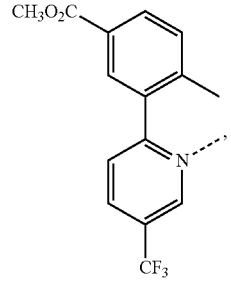
(X-26)
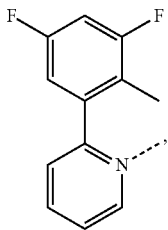
(X-27)

(X-28)
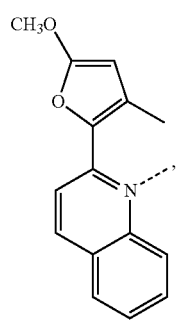
(X-29)
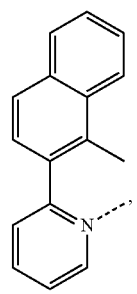
(X-30)
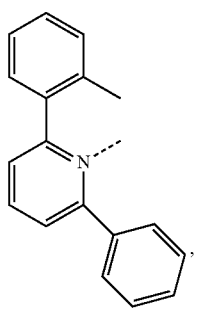
(X-31)
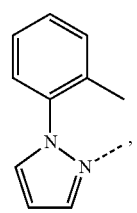
(X-32)
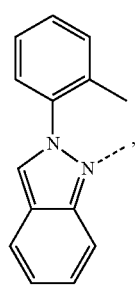
(X-33)
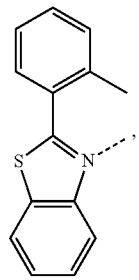
(X-34)
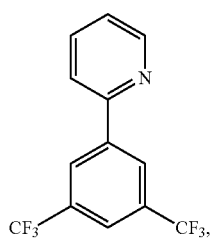
(X-35)
(X-36)
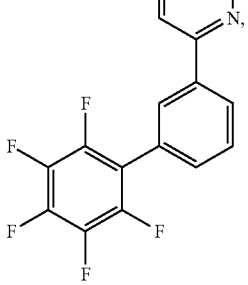
(X-37)
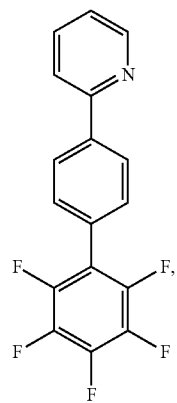

(X-37) 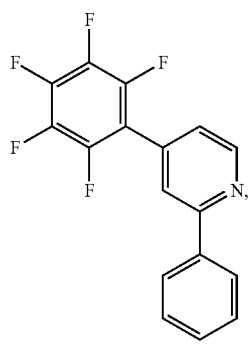
(X-38) 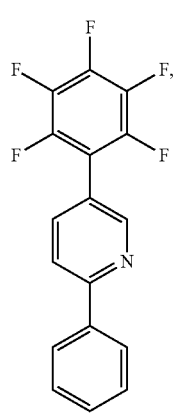
(X-39)
(X-40)
(X-41)
(X-42) 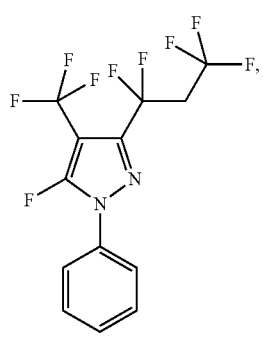
(X-43) 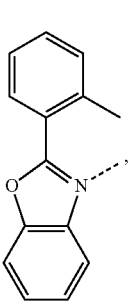
(X-44) 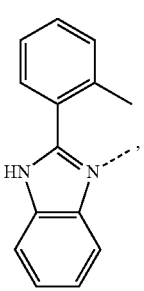
(X-45) 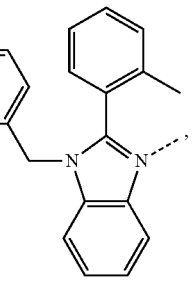
(X-46) 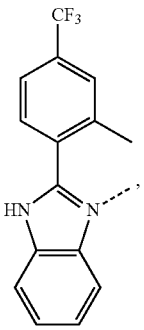

(X-47) 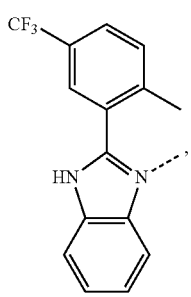
(X-48) 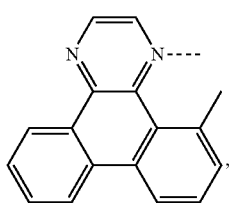
(X-49) 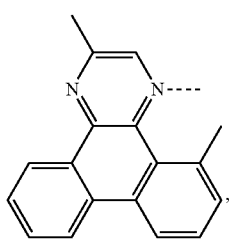
(X-50) 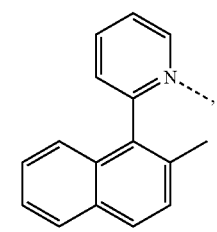
(X-51) 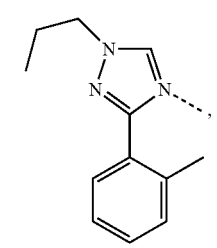
(X-52) 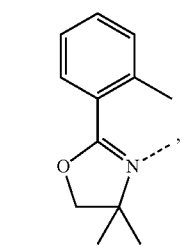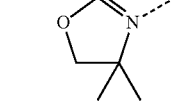
(X-53) 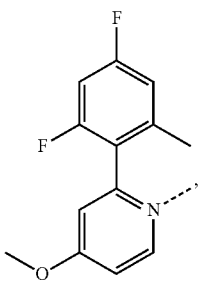
(X-54) 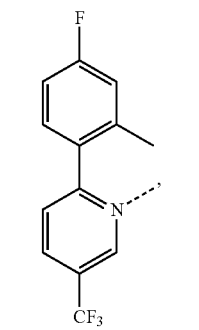
(X-55) 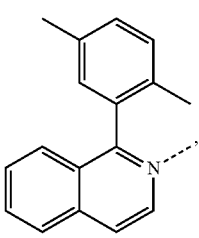
(X-56) 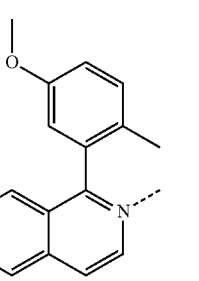
and
(X-57) 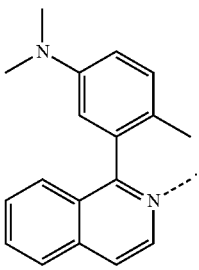
In case of the metal complex $(L^a)_2IrL'$ three isomers can exist.
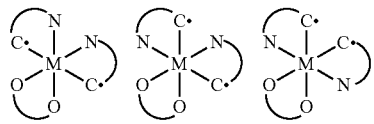
($L^a$ = C・ ⌒ N; $L'$ = O ⌒ O)

In some cases mixtures of isomers are obtained. Often the mixture can be used without isolating the individual isomers. The isomers can be separated by conventional methods, as described in A. B. Tamayo et al., J. Am. Chem. Soc. 2003, 125, 7377-7387.
The at present most preferred ligands L are listed below:
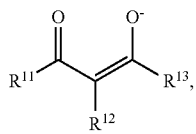
especially
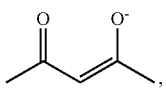
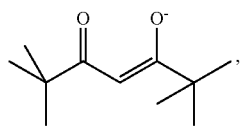
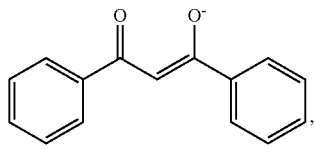
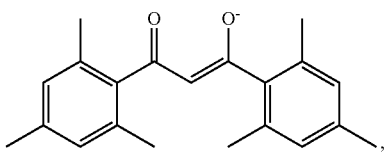
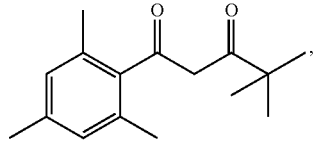
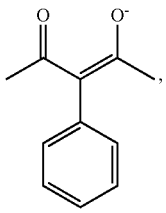
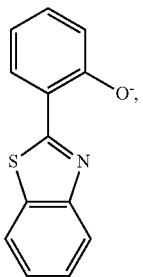
-continued
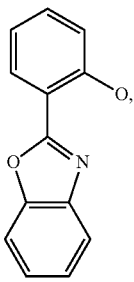
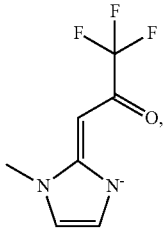
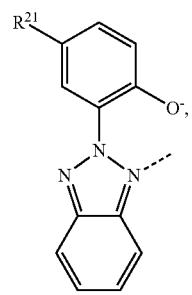
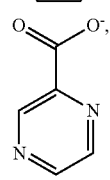
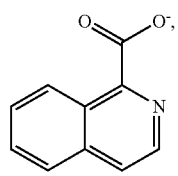
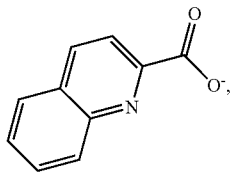
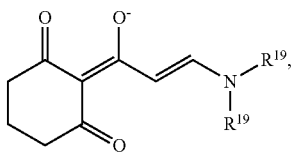
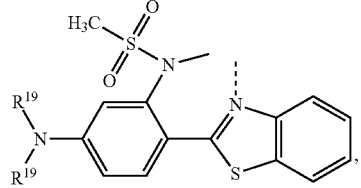

-continued
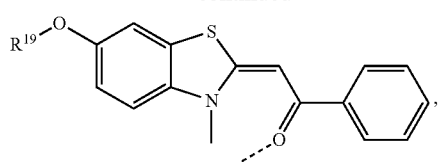
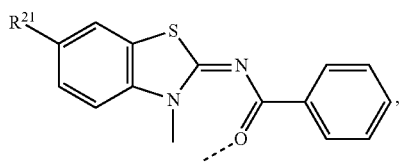
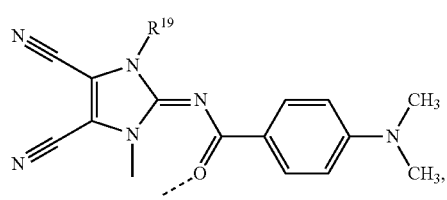
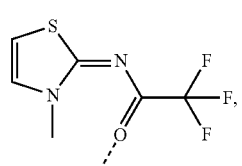
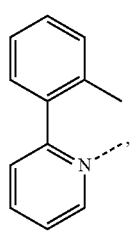
(X-1)
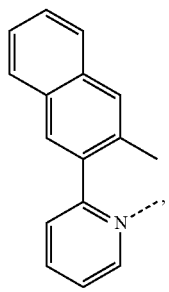
(X-4)
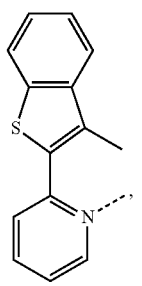
(X-6)
-continued
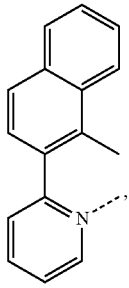
(X-29)
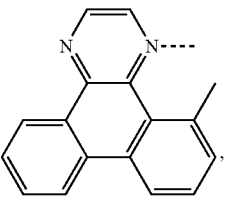
(X-48)
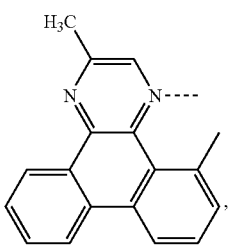
(X-49)
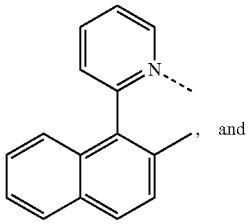
(X-50)
, and
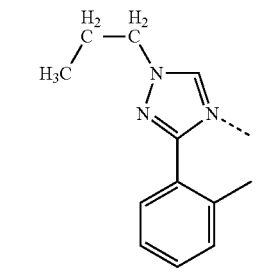
(X-51)
In a preferred embodiment the present invention is directed to compounds of formula
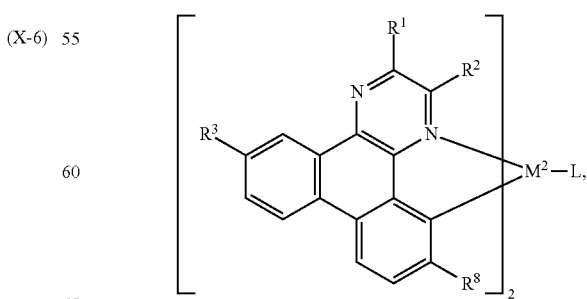
wherein M² is iridium,
R¹ is $C_1$-$C_8$alkyl, $R^2$ is H; or
$R^1$ and $R^2$ together form a ring —(CH$_2$)$_3$—, or —(CH$_2$)$_4$—, which are optionally substituted by one or two $C_1$-$C_8$alkyl,
$R^3$ and $R^8$ are $C_1$-$C_8$alkyl, —Si($C_1$-$C_4$alkyl)$_3$, or $C_3$-$C_6$cycloalkyl and
L is

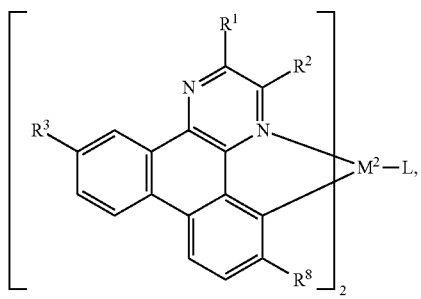

If $R^1$ and $R^2$ together form a ring, —(CH$_2$)$_4$— is preferred.

In another preferred embodiment the present invention is directed to compounds of formula

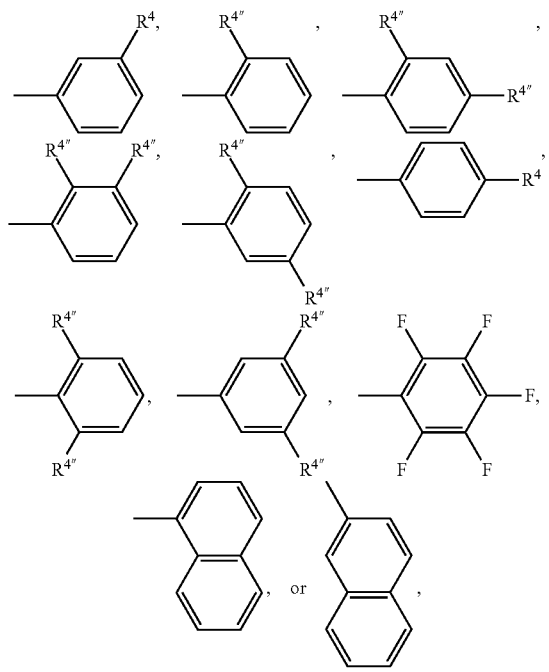

wherein $M^2$ is iridium,
$R^1$ is a group of formula

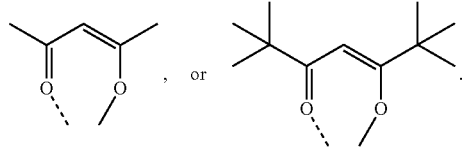,

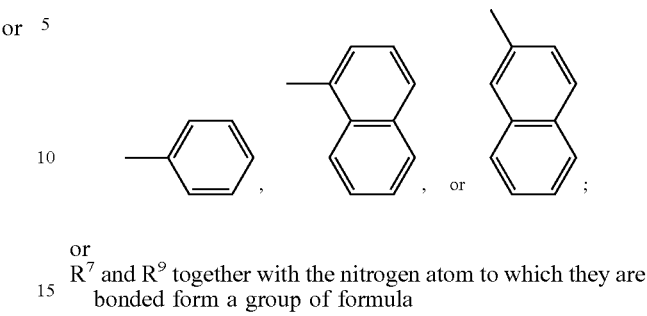

$R^2$ is H;
$R^4$ is cyclohexyl, F, especially $C_1$-$C_8$alkyl, CF$_3$, or NR$^7$R$^9$,
$R^{4''}$ is $C_1$-$C_8$alkyl, or CF$_3$,
$R^7$ and $R^9$ are independently of each other

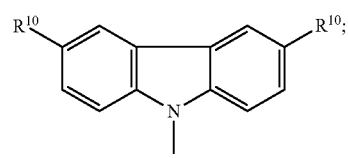

or
$R^7$ and $R^9$ together with the nitrogen atom to which they are bonded form a group of formula

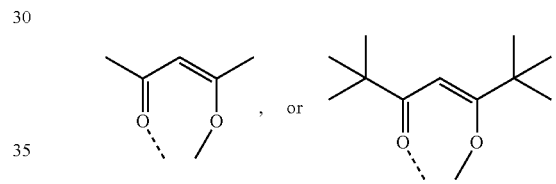

$R^{10}$ is H, or $C_1$-$C_8$alkyl,
$R^3$ and $R^8$ are $C_1$-$C_8$alkyl, —Si($C_1$-$C_4$alkyl)$_3$, or $C_3$-$C_6$cycloalkyl; and
L is

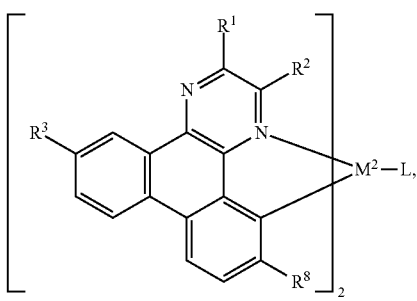

In another preferred embodiment the present invention is directed to compounds of formula

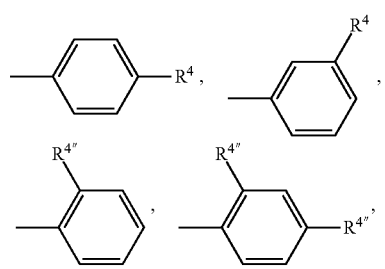

wherein $M^2$ is iridium, $R^1$ is a group of formula

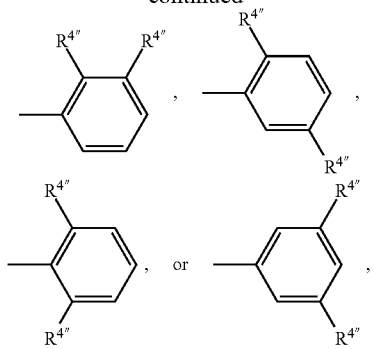

$R^4$ is $C_1$-$C_8$alkyl, or $CF_3$, $R^{4'''}$ is $C_1$-$C_8$alkyl, $R^2$ is H, $R^3$ and $R^8$ are $C_1$-$C_8$alkyl, —Si($C_1$-$C_4$alkyl)$_3$, or $C_3$-$C_6$cycloalkyl; and L is

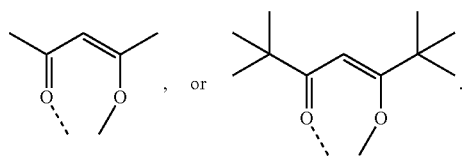

In another preferred embodiment the present invention is directed to compounds of formula

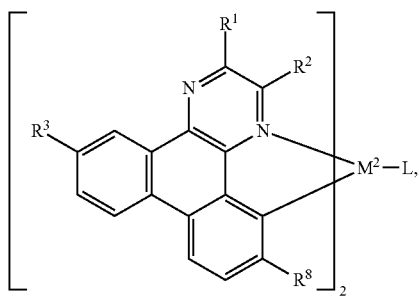

wherein $M^2$ is iridium, $R^1$ is a group of formula

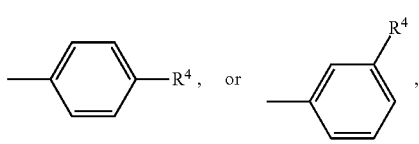

$R^4$ is $NR^7R^9$, $R^7$ and $R^9$ are independently of each other

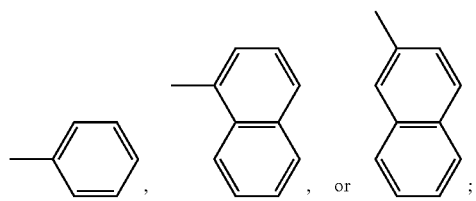

or $R^7$ and $R^9$ together with the nitrogen atom to which they are bonded form a group of formula

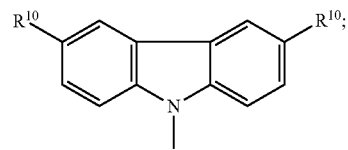

$R^{10}$ is H, or $C_1$-$C_8$alkyl, $R^2$ is H, $R^3$ and $R^8$ are $C_1$-$C_8$alkyl, —Si($C_1$-$C_4$alkyl)$_3$, or $C_3$-$C_6$cycloalkyl; and L is

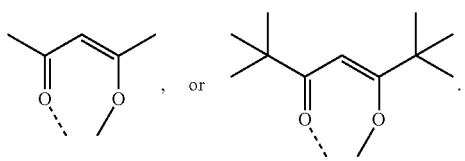

In another preferred embodiment the present invention is directed to compounds of formula

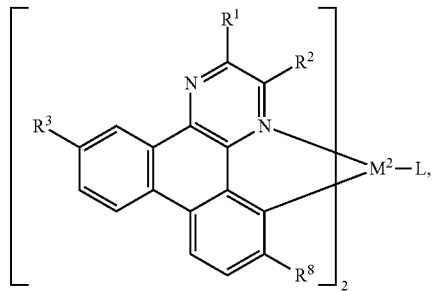

wherein $M^2$ is iridium, $R^1$ is a group of formula

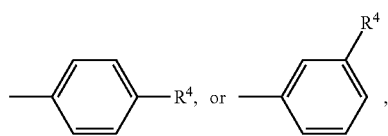

$R^4$ is $CF_3$, $R^2$ is H, $R^3$ and $R^8$ are $C_1$-$C_8$alkyl, —Si($C_1$-$C_4$alkyl)$_3$, or $C_3$-$C_6$cycloalkyl; and L is

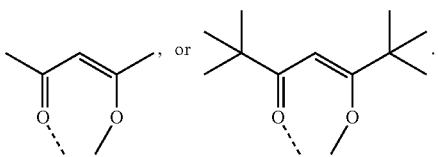

In another preferred embodiment the present invention is directed to compounds of formula

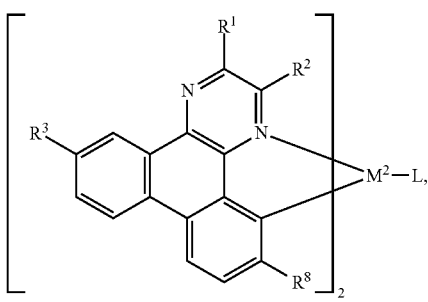

wherein $M^2$ is iridium, $R^1$ is a group of formula

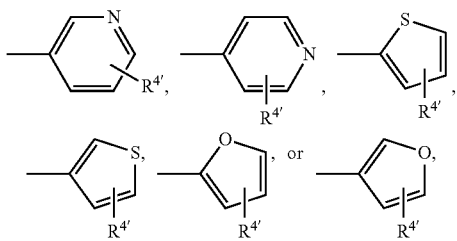

$R^{4'}$ is H, $CF_3$ or $C_1$-$C_8$alkyl; $R^2$ is H, $R^3$ and $R^8$ are $C_1$-$C_8$alkyl, —Si($C_1$-$C_4$alkyl)$_3$, or $C_3$-$C_6$cycloalkyl; and L is

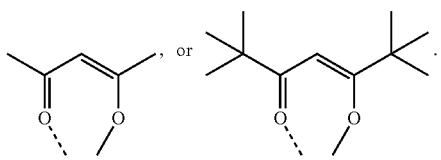

Most preferred are compounds of formula:

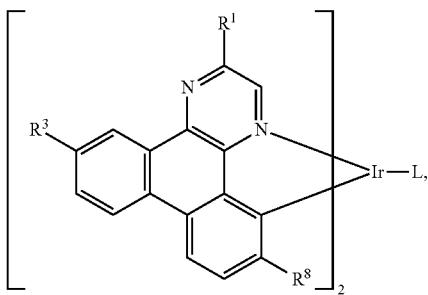

wherein $R^1$ is $C_1$-$C_5$alkyl, especially methyl, ethyl, tert-butyl, iso-butyl, or neopentyl,
$R^3$ and $R^8$ are $C_1$-$C_5$alkyl, especially methyl, ethyl, iso-butyl, or neopentyl and L is

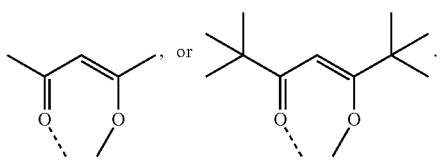

Examples of specific compounds of formula I are compounds A-1 to A-114, B-1 to B-144, C-1 to C-120 and D-1 to D41. Reference is made to claim 9. Compounds, A-1, A-16, A-30, A-44, A-58, A-72, A-87 and A-101, wherein $R^1$ is H, are less preferred.

Special emphasis among them is given to compounds A-9, A-23, A-37, A-2, A-3, A-31, A-10, A-24, A-38, A-65, A-79, A-94, A-59, A-73, A-88, A-66, A-80, A-95, A-12, A-14, A-26, A-28, A-40, A-42, A-54, A-56, A-68, A-70, A-82, A-84, A-97, A-99, A-111, A-113, B-1, B-2, B-3, B-4, B-7, B-9, B-13, B-15, B-17, B-20, B-21, B-22, B-23, B-26, B-27, B-31, B-33, B-35, B-38, B-39, B-40, B-41, B-44, B-45, B-49, B-51, B-53, B-56, B-57, B-58, B-59, B-62, B-63, B-67, B-69, B-71, B-74, B-75, B-76, B-79, B-80, B-84, B-86, B-88, B-91, B-92, B-93, B-94, B-97, B-98, B-102, B-104, B-106, B-109, B-110, B-111, B-112, B-115, B-116, B-120, B-122, B-124, B-127, B-128, B-129, B-133, B-134, B-138, B-140, B-142, C-2 to C-4, C-6, C-9 to C-12, C-14, C-63 to C-65, C-67, C-69 to C-72, C-74, D-2 to D-4, D-6, D-9 to D-12, and D-14. More preferred compounds are A-9, A-23, A-37, A-2, A-3, A-31, A-10, A-24, A-38, A-65, A-79, A-94, A-59, A-73, A-88, A-66, A-80, A-95, A-12, A-14, A-26, A-28, A-40, A-42, A-54, A-56, A-68, A-70, A-82, A-84, A-97, A-99, A-111, A-113, C-2 to C-4, C-6, C-9 to C-12, C-14, C-63 to C-65, C-67, C-69 to C-72, and C-74. Even more preferred compounds are A-9, A-23, A-37, A-2, A-3, A-31, A-10, A-24, A-38, A-65, A-79, A-94, A-59, A-73, A-88, A-66, A-80, A-95, A-12, A-14, A-26, A-28, A-40, A-42, A-54, A-56, A-68, A-70, A-82, A-84, A-97, A-99, A-111, and A-113. Most preferred are compounds of formula:

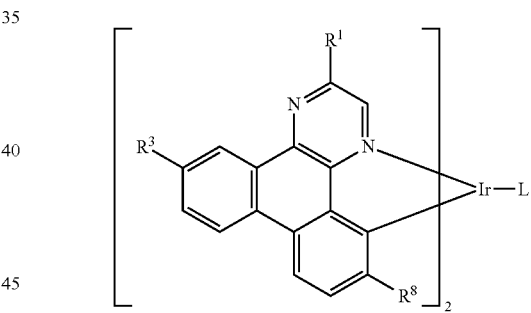

| Cpd. | L | $R^1$ | $R^3$ | $R^8$ |
|---|---|---|---|---|
| A-9 | $A^{1)}$ | —CH$_2$CH(CH$_3$)$_2$ | —CH$_3$ | —CH$_3$ |
| A-23 | $A^{1)}$ | —CH$_2$CH(CH$_3$)$_2$ | —CH$_2$CH$_3$ | —CH$_2$CH$_3$ |
| A-37 | $A^{1)}$ | —CH$_2$CH(CH$_3$)$_2$ | —CH$_2$CH(CH$_3$)$_2$ | —CH$_2$CH(CH$_3$)$_2$ |
| A-2 | $A^{1)}$ | —CH$_3$ | —CH$_3$ | —CH$_3$ |
| A-3 | $A^{1)}$ | —CH$_3$ | —CH$_2$CH$_3$ | —CH$_2$CH$_3$ |
| A-31 | $A^{1)}$ | —CH$_3$ | —CH$_2$CH(CH$_3$)$_2$ | —CH$_2$CH(CH$_3$)$_2$ |
| A-10 | $A^{1)}$ | —C(CH$_3$)$_3$ | —CH$_3$ | —CH$_3$ |
| A-24 | $A^{1)}$ | —C(CH$_3$)$_3$ | —CH$_2$CH$_3$ | —CH$_2$CH$_3$ |
| A-38 | $A^{1)}$ | —C(CH$_3$)$_3$ | —CH$_2$CH(CH$_3$)$_2$ | —CH$_2$CH(CH$_3$)$_2$ |
| A-65 | $A^{1)}$ | —CH$_2$CH(CH$_3$)$_2$ | —CH$_3$ | —CH$_3$ |
| A-79 | $B^{1)}$ | —CH$_2$CH(CH$_3$)$_2$ | —CH$_2$CH$_3$ | —CH$_2$CH$_3$ |
| A-94 | $B^{1)}$ | —CH$_2$CH(CH$_3$)$_2$ | —CH$_2$CH(CH$_3$)$_2$ | —CH$_2$CH(CH$_3$)$_2$ |
| A-59 | $B^{1)}$ | —CH$_3$ | —CH$_3$ | —CH$_3$ |
| A-73 | $B^{1)}$ | —CH$_3$ | —CH$_2$CH$_3$ | —CH$_2$CH$_3$ |
| A-88 | $B^{1)}$ | —CH$_3$ | —CH$_2$CH(CH$_3$)$_2$ | —CH$_2$CH(CH$_3$)$_2$ |
| A-66 | $B^{1)}$ | —C(CH$_3$)$_3$ | —CH$_3$ | —CH$_3$ |
| A-80 | $B^{1)}$ | —C(CH$_3$)$_3$ | —CH$_2$CH$_3$ | —CH$_2$CH$_3$ |
| A-95 | $B^{1)}$ | —C(CH$_3$)$_3$ | —CH$_2$CH(CH$_3$)$_2$ | —CH$_2$CH(CH$_3$)$_2$ |

| Cpd. | L | R¹ | R³ | R⁸ |
|---|---|---|---|---|

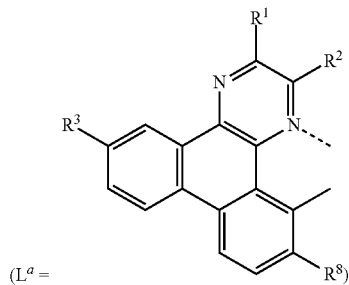

The metal complexes of the present invention can be prepared according to usual methods known in the prior art. A convenient one-step method for preparing iridium metal complexes of formula Ir(L^a)_3

(L^a =
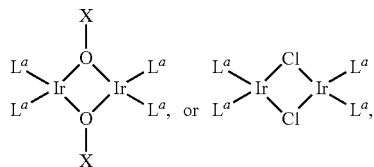
)

comprises reacting commercially available iridium trichloride hydrate with an excess of L^aH in the presence of 3 equivalents silver trifluoroacetate and optionally in the presence of a solvent (such as halogen based solvents, alcohol based solvents, ether based solvents, ester based solvents, ketone based solvents, nitrile based solvents, and water). The tris-cyclometalated iridium complexes are isolated and purified by conventional methods. In some cases mixtures of isomers are obtained. Often the mixture can be used without isolating the individual isomers.

The iridium metal complexes of formula Ir(L^a)_2L can, for example, be prepared by first preparing an intermediate iridium dimer of formula

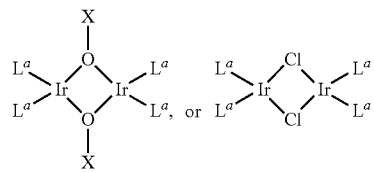

wherein X is H, methyl, or ethyl, and L^a is as defined above, and then addition of HL. The iridium dimers can generally be prepared by first reacting iridium trichloride hydrate with HL^a and adding NaX and by reacting iridium trichloride hydrate with HL^a in a suitable solvent, such as 2-ethoxyethanol. The compounds of formula

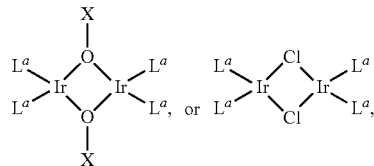

are new and form a further aspect of the present invention.

Accordingly, the present invention relates to compounds of formula

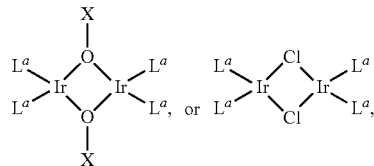

wherein X is H, methyl, or ethyl,
L^a is

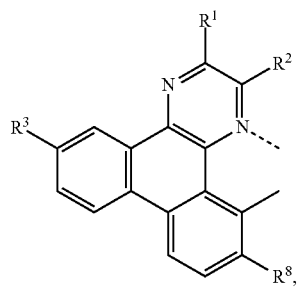

wherein R¹, R², R³ and R⁸ are as defined above.

Compounds of formula VIa, or VIb can be synthesized, for example, as outlined in FIGS. 7 and 8 of U.S. Pat. No. 7,166,368.

$C_1$-$C_{18}$alkyl is a branched or unbranched radical such as for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl,1,1,3,3,5,5-hexamethylhexyl, tridecyl, tetradecyl, pentadecyl, hexadecyl, heptadecyl, octadecyl, icosyl or docosyl. $C_1$-$C_8$alkyl is a branched or unbranched radical such as for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl,1,1,3,3-tetramethylbutyl, 1-methylheptyl, 3-methylheptyl, n-octyl, or 2-ethylhexyl.

$C_1$-$C_8$perfluoroalkyl is a branched or unbranched radical, such as, for example, —$CF_3$, —$CF_2CF_3$, -$CF_2CF_2CF_3$, —$CF(CF_3)_2$, —$(CF_2)_3CF_3$, and —$C(CF_3)_3$.

$C_3$-$C_8$cycloalkyl is preferably $C_5$-$C_{12}$cycloalkyl or said cycloalkyl substituted by one, or two $C_1$-$C_8$alkyl, or $C_1$-$C_8$perfluoroalkyl groups, such as, for example, cyclopropyl, cyclobutyl, cyclopentyl, methylcyclopentyl, dimethylcyclopentyl, cyclohexyl, methylcyclohexyl, dimethylcyclohexyl, trimethylcyclohexyl, and tert-butylcyclohexyl.

$C_1$-$C_8$alkoxy radicals are straight-chain or branched alkoxy radicals, e.g. methoxy, ethoxy, n-propoxy, isopropoxy, n-butoxy, sec-butoxy, tert-butoxy, amyloxy, isoamyloxy or tertamyloxy, heptyloxy, or octyloxy.

Aryl is usually $C_6$-$C_{18}$aryl, preferably $C_6$-$C_{10}$aryl, which optionally can be substituted, such as, for example, phenyl, 4-methylphenyl, 4-methoxyphenyl, naphthyl, biphenylyl, 2-fluorenyl, phenanthryl, anthryl, tetracenyl, terphenylyl or quadphenylyl; or phenyl substituted by one to three $C_1$-$C_4$alkyl groups, for example o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

$C_7$-$C_{24}$aralkyl radicals are preferably $C_7$-$C_{15}$aralkyl radicals, which may be substituted, such as, for example, benzyl, 2-benzyl-2-propyl, β-phenethyl, α-methylbenzyl, α,α-dimethylbenzyl, ω-phenyl-butyl, ω-phenyl-octyl, ω-phenyl-dodecyl; or phenyl-$C_1$-$C_4$alkyl substituted on the phenyl ring by one to three $C_1$-$C_4$alkyl groups, such as, for example,2-methylbenzyl, 3-methylbenzyl, 4-methylbenzyl, 2,4-dimethyl benzyl, 2,6-dimethylbenzyl or 4-tert-butylbenzyl.or 3-methyl-5-(1',1',3',3'-tetramethyl-butyl)-benzyl.

Heteroaryl is typically $C_2$-$C_{10}$heteroaryl, i.e. a ring with five to seven ring atoms or a condensed rig system, wherein nitrogen, oxygen or sulfur are the possible hetero atoms, and is typically an unsaturated heterocyclic radical with five to 12 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, or indazolyl, which can be unsubstituted or substituted.

Possible substituents of the above-mentioned groups are $C_1$-$C_8$alkyl, $C_1$-$C_8$alkoxy, fluorine, $C_1$-$C_8$perfluoroalkyl, or a cyano group.

The tri$C_1$-$C_8$alkylsilyl group is preferably a tri$C_1$-$C_4$alkylsilylgroup, such as, for example, a trimethylsilyl group.

If a substituent, such as, for example, $R^4$, $R^5$, or $R^6$, occurs more than one time in a group, it can be different in each occurrence.

It has been found that the compounds of the formula I are particularly suitable for use in applications in which charge carrier conductivity is required, especially for use in organic electronics applications, for example selected from switching elements such as organic transistors, e.g. organic FETs and organic TFTs, organic solar cells and organic light-emitting diodes (OLEDs), the compounds of the formula I being particularly suitable in OLEDs for use as guest material in a light-emitting layer, especially in combination with a host material. In the case of use of the inventive compounds of the formula I in OLEDs, OLEDs which have good efficiencies and a long lifetime and which can be operated especially at a low use and operating voltage are obtained. The inventive compounds of the formula I are suitable especially for use as emitting materials (phosphorescence emitters).

Suitable structures of organic electronic devices are known to those skilled in the art and are specified below.

The organic transistor generally includes a semiconductor layer formed from an organic layer with hole transport capacity and/or electron transport capacity; a gate electrode formed from a conductive layer; and an insulating layer introduced between the semiconductor layer and the conductive layer. A source electrode and a drain electrode are mounted on this arrangement in order thus to produce the transistor element. In addition, further layers known to those skilled in the art may be present in the organic transistor.

The organic solar cell (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes. When, however, plate-type electrodes arranged in parallel are used, at least one electrode is preferably formed from a transparent electrode, for example an ITO electrode or a fluorine-doped tin oxide electrode. The organic layer is formed from two sublayers, i.e. a layer with p-type semiconductor properties or hole transport capacity, and a layer formed with n-type semiconductor properties or electron transport capacity. In addition, it is possible for further layers known to those skilled in the art to be present in the organic solar cell.

The present invention further provides an organic light-emitting diode comprising an anode An and a cathode Ka and a light-emitting layer E arranged between the anode An and the cathode Ka, and if appropriate at least one further layer selected from the group consisting of at least one blocking layer for holes/excitons, at least one blocking layer for electrons/excitons, at least one hole injection layer, at least one hole transport layer, at least one electron injection layer and at least one electron transport layer, wherein the at least one compound of the formula I is present in the light-emitting layer E and/or in at least one of the further layers. The at least one compound of the formula I is preferably present in the light-emitting layer and/or the blocking layer for holes and/or electron transport layer. For the use of the compounds of formula I in electronic devices the same preferences with respect to the compounds of formula I apply as specified above with respect to the compounds of formula I.

Structure of the Inventive OLED

The inventive organic light-emitting diode (OLED) thus generally has the following structure:
an anode (An) and a cathode (Ka) and a light-emitting layer E arranged between the anode (An) and the cathode (Ka).

The inventive OLED may, for example—in a preferred embodiment—be formed from the following layers:
1. Anode
2. Hole transport (conductor) layer
3. Light-emitting layer
4. Blocking layer for holes/excitons
5. Electron transport (conductor) layer
6. Cathode Layer sequences different than the aforementioned structure are also possible, and are known to those skilled in the art. For example, it is possible that the OLED does not have all of the layers mentioned; for example, an OLED with layers (1) (anode), (3) (light-emitting layer) and (6) (cathode) is likewise suitable, in which case the functions of the layers (2) (hole conductor layer) and (4) (blocking layer for holes/excitons) and (5) (electron conductor layer) are assumed by the adjacent layers. OLEDs which have layers (1), (2), (3) and (6), or layers (1), (3), (4), (5) and (6), are likewise suitable. In addition, the OLEDs may have a blocking layer for electrons/excitons between the anode (1) and the hole conductor layer (2).

It is additionally possible that a plurality of the aforementioned functions (electron/exciton blocker, hole/exciton blocker, hole injection, hole conduction, electron injection, electron conduction) are combined in one layer and are assumed, for example, by a single material present in this layer. For example, a material used in the hole conductor layer, in one embodiment, may simultaneously block excitons and/or electrons.

Furthermore, the individual layers of the OLED among those specified above may in turn be formed from two or more layers. For example, the hole conductor layer may be formed from a layer into which holes are injected from the electrode, and a layer which transports the holes away from the hole-injecting layer into the light-emitting layer. The electron conduction layer may likewise consist of a plurality of layers, for example a layer in which electrons are injected by the electrode, and a layer which receives electrons from the electron injection layer and transports them into the light-emitting layer.

In order to obtain particularly efficient OLEDs, for example, the HOMO (highest occupied molecular orbital) of the hole transport layer should be matched to the work function of the anode, and the LUMO (lowest unoccupied molecular orbital) of the electron transport layer should be matched to the work function of the cathode, provided that the aforementioned layers are present in the inventive OLEDs.

The anode (1) is an electrode which provides positive charge carriers. It may be formed, for example, from materials which comprise a metal, a mixture of various metals, a metal alloy, a metal oxide or a mixture of various metal oxides. Alternatively, the anode may be a conductive polymer. Suitable metals comprise metals and alloys of the metals of the main groups, transition metals and of the lanthanoids, especially the metals of groups Ib, IVa, Va and VIa of the periodic table of the elements, and the transition metals of group VIIIa. When the anode is to be transparent, generally mixed metal oxides of groups IIb, IIIb and IVb of the periodic table of the elements (IUPAC version) are used, for example indium tin oxide (ITO). It is likewise possible that the anode (1) comprises an organic material, for example polyaniline, as described, for example, in Nature, Vol. 357, pages 477 to 479 (Jun. 11, 1992). At least either the anode or the cathode should be at least partly transparent in order to be able to emit the light formed. The material used for the anode (1) is preferably ITO.

Suitable hole transport materials for layer (2) of the inventive OLEDs are disclosed, for example, in Kirk-Othmer Encyclopedia of Chemical Technology, 4th edition, Vol. 18, pages 837 to 860, 1996. Both hole-transporting molecules and polymers can be used as the hole transport material. Hole-transporting molecules typically used are selected from the group consisting of tris[N-(1-naphthyl)-N-(phenylamino)]triphenylamine (1-NaphDATA), 4,4'-bis[N-(1-naphthyl)-N-phenylamino]piphenyl (α-NPD), N,N'-diphenyl-N,N'-bis(3-methylphenyl)-[1,1'-biphenyl]-4,4%-diamine (TPD), 1,1-bis[(di-4-tolylamino)phenyl]cyclohexane (TAPC), N,N'-bis(4-methylphenyl)-N,N'-bis(4-ethylphenyl)[1,1'-(3,3',-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl)(4-methylphenyl)methane (MPMP), 1-phenyl-3[p-(diethylamino)styryl]-54p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), 4,4',4"-tris(N,N-diphenylamino)triphenylamine (TDTA), 4,4',4"-tris(N-carbazolyl)triphenylamine (TCTA), N,N'-bis(naphthalen-2-yl)-N,N'-bis(phenyl)benzidine (β-NPB), N,N'-bis(3-methylphenyl)-N, N'-bis(phenyl)-9,9-spirobifluorene (Spiro-TPD), N,N'-bis(naphthalen-1-yl)-N,N'-bis(phenyl)-9,9-spirobifluorene (Spiro-NPB), N,N'-bis(3-methylphenyl)-N,N'-bis(phenyl)-9,9-dimethylfluorene (DMFL-TPD), di[4-(N,N-ditolylamino)phenyl]cyclohexane, N,N'-bis(naphthalene-1-yl)-N,N'-bis(phenyl)-9,9-dimethylfluorene, N,N'-bis(naphthalen-1-yl)-N,N'-bis (phenyl)-2,2-dimethylbenzidine, N,N'-bis(naphthalen-1-yl)-N,N'-bis(phenyl)benzidine, N,N'-bis(3-methylphenyl)-N,N'-bis(phenyl)benzidine, 2,3,5,6-tetrafluoro-7,7,8,8-tetracyanoquinodimethane (F4-TCNQ), 4,4',4"-tris(N-3-methylphenyl-N-phenylamino)triphenylamine, 4,4',4"-tris(N-(2-naphthyl)-N-phenyl-amino)triphenylamine, pyrazino[2,3-f][1,10]phenanthroline-2,3-dicarbonitrile (PPDN), N,N,N',N'-tetrakis(4-methoxyphenyl) benzidine (MeO-TPD), 2,7 -bis[N,N-bis(4-methoxyphenyl)amino]-9,9-spirobifluorene (MeO-Spiro-TPD), 2,2'-bis[N,N-bis(4-methoxyphenyl)amino]-9,9-spirobifluorene (2,2'-MeO-Spiro-TPD), N,N'-diphenyl-N,N'-di[4-(N,N-ditolylamino) phenyl]benzidine (NTNPB), N,N'-diphenyl-N,N'-di[4-(N,N-diphenylamino) phenyl]benzidine (NPNPB), N,N'-di(naphthalen-2-yl)-N,N'-diphenylbenzene-1,4-diamine (β-NPP), N,N'-bis(3-methylphenyl)-N,N'-bis(phenyl)-9,9-diphenylfluorene (DPFL-TPD), N,N'-bis(naphthalen-1-yl)-N,N'-bis(phenyl)-9,9-diphenylfluorene (DPFL-NPB), 2,2',7,7'-tetrakis(N,N-diphenylamino)-9,9'-spirobifluorene (Spiro-TAD), 9,9-bis[4-(N,N-bis(biphenyl-4-yl)amino)phenyl]-9H-fluorene (BPAPF), 9,9-bis[4-(N,N-bis(naphthalen-2-yl)amino)phenyl]-9H-fluorene (NPAPF), 9,9-bis[4-(N,N-bis(naphthalen-2-yl)-N,N'-bisphenylamino)phenyl]-9H-fluorene (NPBAPF), 2,2',7,7'-tetrakis[N-naphthalenyl (phenyl) amino]-9,9'-spirobifluorene (Spiro-2NPB), N,N'-bis(phenanthren-9-yl)-N,N'-bis(phenyl)benzidine (PAPB), 2,7-bis[N,N-bis(9,9-spirobifluoren-2-yl)amino]-9,9-spirobifluorene (Spiro-5), 2,2'-bis[N,N-bis(biphenyl-4-yl) amino]9,9-spirobifluorene (2,2'-Spiro-DBP), 2,2'-bis(N,N-diphenylamino)-9.9-spirobifluorene (Spiro-BPA), 2,2',7,7'-tetra(N,N-ditolyl)aminospirobifluorene (Spiro-TTB), N,N,N',N'-tetranaphthalen-2-ylbenzidine (TNB), porphyrin compounds and phthalocyanines such as copper phthalocyanines and titanium oxide phthalocyanines. Hole-transporting polymers typically used are selected from the group consisting of polyvinylcarbazoles, (phenylmethyl)polysilanes and polyanilines. It is likewise possible to obtain hole-transporting polymers by doping hole-transporting molecules into polymers such as polystyrene and polycarbonate. Suitable hole-transporting molecules are the molecules already mentioned above.

In addition—in one embodiment—it is possible to use carbene complexes as hole transport materials, the band gap of the at least one hole transport material generally being greater than the band gap of the emitter material used. In the context of the present application, "band gap" is understood to mean the triplet energy. Suitable carbene complexes are, for example, carbene complexes as described in WO 2005/019373 A2, WO 2006/056418 A2, WO2005/113704, WO 2007/115970, WO2007/115981 and WO2008/000727. One example of a suitable carbene complex is Ir(dpbic)$_3$ with the formula:

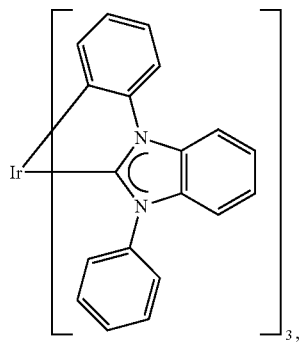

which is disclosed, for example, in WO2005/019373. In principle, it is possible that the hole transport layer comprises at least one compound of the formula I as hole transport material.

The light-emitting layer (3) includes a compound of formula I according to the present invention (emitter).

The light-emitting layer (3) may comprise a host material. Suitable host materials are, for example, described in EP2363398A1, WO2008031743, WO2008065975, WO2010145991, WO2010047707, US20090283757, US20090322217, US20100001638, WO2010002850, US20100060154, US20100060155, US20100076201, US20100096981, US20100156957, US2011186825, US2011198574, US20110210316, US2011215714, US2011284835, and PCT/EP2011/067255. The host material may be an organic compound having hole-transporting property and/or an organic compound having electron-transporting property. Preferably, the light-emitting layer (3) comprises a compound of formula I according to the present invention and an organic compound having hole-transporting property; or the light-emitting layer (3) comprises a compound of formula I according to the present invention, an organic compound having hole-transporting property and an organic compound having electron-transporting property.

The compound of formula I is used in the emitting layer (3) in an amount of 0.01 to 15% by weight, preferably 1 to 10% by weight based on the amount of the compound of formula I, the organic compound having hole-transporting property and/or the organic compound having electron-transporting property. Furthermore, the weight ratio of the organic compound having hole-transporting property to the organic compound having electron-transporting property is preferably in the range of 1:20 to 20:1. For the compound of formula I the same preferences apply as specified above.

In principle, any organic compound having hole-transporting property can be used as host in the emitting layer. Examples of organic compounds having a hole transport property which can be used for the host material include an aromatic amine compound such as 4,4'-bis[N-(1-naphthyl)-N-phenylamino]biphenyl (α-NPD), 4,4'-bis[N-(naphthyl)-N-phenylamino]biphenyl (=NPB), 4,4'-bis[N-(9-phenanthryl)-N-phenylamino]biphenyl (=PPB), 4,4'-bis[N-(3-methylphenyl)-N-phenylamino]biphenyl (=TPD), 4,4'-bis[N-(9,9-dimethylfluoren-2-yl)-N-phenylamino]biphenyl (=DFLDPBi), 4,4,4"-tris(N, N-diphenyl-amino) -triphenylamine (=TDATA), 4,4,4"-tris[N-(3-methylphenyl)-N-phenylamino]-triphenylamine (=m-MTDATA), 4,4,4"-tris-(N-carbazolyl)triphenylamine (=TCTA), 1,1-bis [4-(diphenylamino)phenyl]-cyclohexane (=TPAC), 9,9-bis[4-(diphenylamino)phenyl]-fluorene (=TPAF), N44-(9-carbazolyl)phenyl1-N-phenyl-9,9-dinnethylfluoren-2-amine (abbreviation: YGAF) and a carbazole derivative such as 4,4'-di(carbazolyl)biphenyl (abbreviation: CBP), 1,3-bis (carbazolyl)benzene (abbreviation: mCP) or 1,3,5-tris(N-carbazolyl) benzene (abbreviation: TCzB), =DNTPD,

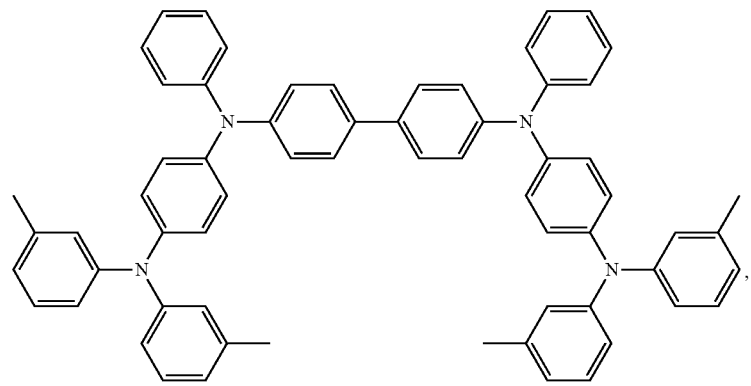

(abbreviation: DNTPD)

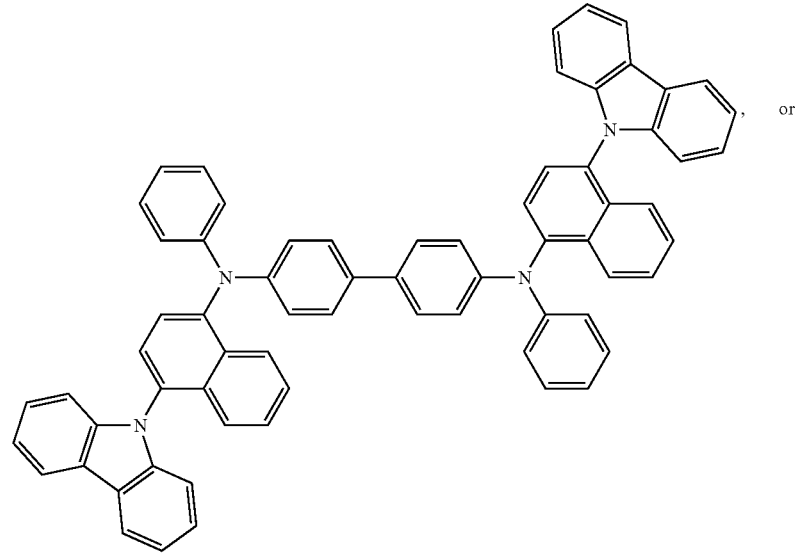

, or

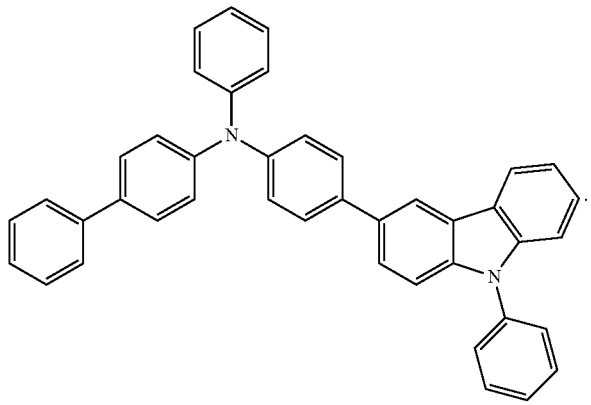

Examples of high molecular compounds having a hole-transport property which can be used for the host material include poly(N-vinylcarbazole) (=PVK), poly(4-vinyltriphenyl-amine) (=PVTPA), poly[N-(4-{N'-[4-(4-diphenylamino)phenyl]phenyl-N'-phenylamino}-phenyl)methacrylamide] (=PTP-DMA), poly[N,N'-bis(4-butylphenyl)-N,N'-bis(phenyl)-benzidine (=Poly-TPD), and the like.

In principle, any organic compound having electron-transporting property can be used as host in the emitting layer. Examples of organic compounds having an electron transport property which can be used for the host material include a heteroaromatic compound such as 9-[4-(5-phenyl-1,3,4-oxadiazol-2-yl)phenyl]carbazole, 1, 3-bis[5-(p-tert-butylphenyl)-1,3,4-oxadiazol-2-yl]benzene (=OXD-7), 2-(4-biphenylyl)-5-(4-tert-butylphenyl)-1,3,4-oxadiazole (=PBD), 2,2',2"-(1,3,5-benzenetriyl)tris(1-phenyl-1H-benzimidazole) (=TPBI), 3-(4-tert-butylphenyl)-4-phenyl-5-(4-biphenylyl)-1,2,4-triazole (=TAZ), 3-(4-tert-butylphenyl)-4-(4-ethylphenyl)-5-(4-biphenylyl)-1,2,4-triazole (=p-EtTAZ), 9,9',9"-[1,3,5-triazine-2,4,6-triyl]tricarbazole (=TCz TRZ), 2,2',2"-(1,3,5-benzenetriyl)tris(6,7-dimethyl-3-phenylquinoxaline) (=TriMeQn), 2,3-bis(4-diphenylaminophenyl)quinoxaline (=TPAQn), 9,9'-(quinoxaline-2,3-diyldi-4,1-phenylene)di(9H-carbazole) (=CzQn), 3,3',6,6'-tetraphenyl-9,9'-(quinoxaline-2, 3-diyldi-4,1 -phenylene)di(9H-carbazole) (=DCzPQ), bathophenanthro-line (=BPhen), or bathocuproine (=BCP), and a metal complex such as tris(8-quinolinolato)aluminum (=Alq$_3$), bis(2-methyl-8-quinolinolato) (4-phenylphenolato)aluminum(III) (=BAlq), tris[2(2-hydroxyphenyl)-5-phenyl-1,3,4-oxadiazolato]aluminum(III) (=Al(OXD)$_3$), tris(2-hydroxyphenyl-1-phenyl-1-H-benzimidazolato)aluminum(III) (=Al(BIZ)$_3$), bis[2-(2-hydroxyphenyl)benzothiazolato]zinc(II) (=Zn(BTZ)$_2$), bis[2-(2-hydroxyphenyl)benzoxazolato]zinc(II) (=Zn(PBO)$_2$), bis[2-(2-hydroxyphenyl)pyridinato]zinc (=Znpp$_2$),

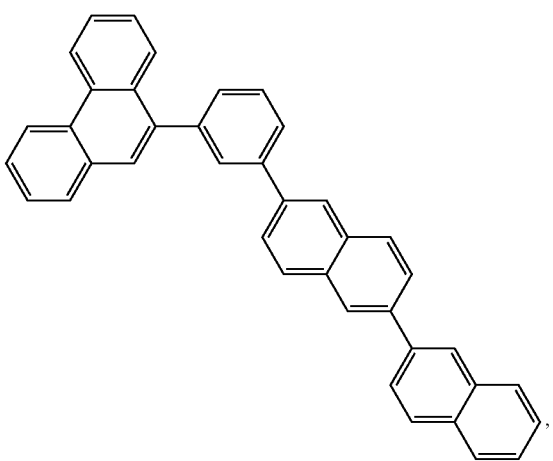

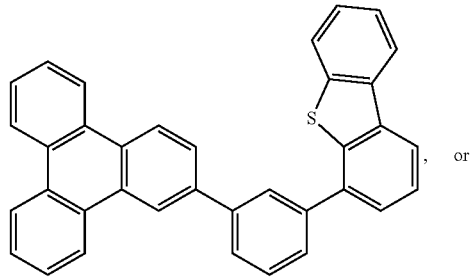

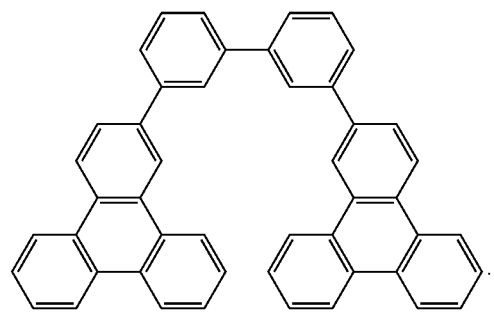

Examples of high molecular compounds having an electron-transport property which can be used for the host material include poly(2,5-pyridinediyl) (abbreviation: PPy), poly [(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] (abbreviation: PF-BPy), and the like.

In another embodiment of the present invention bipolar host materials, such as, for example,

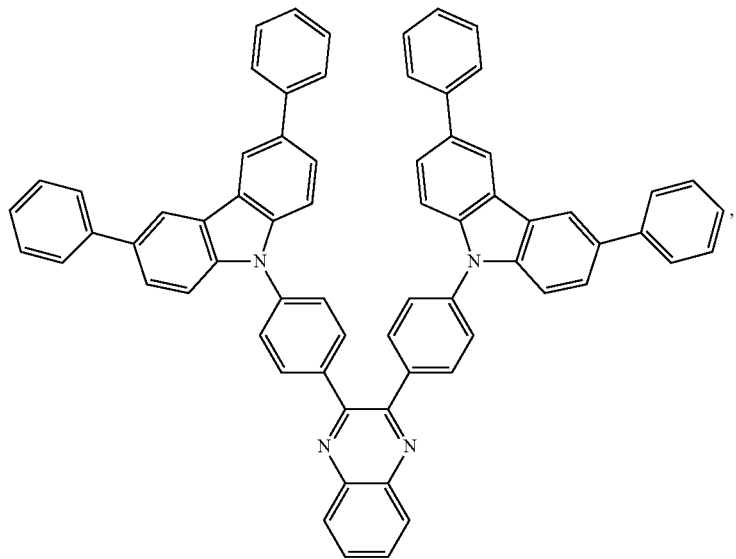

(abbreviation: DCzPQ)

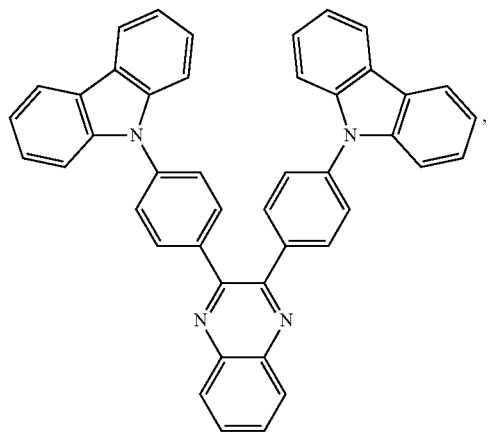

(abbreviation: CzQn)

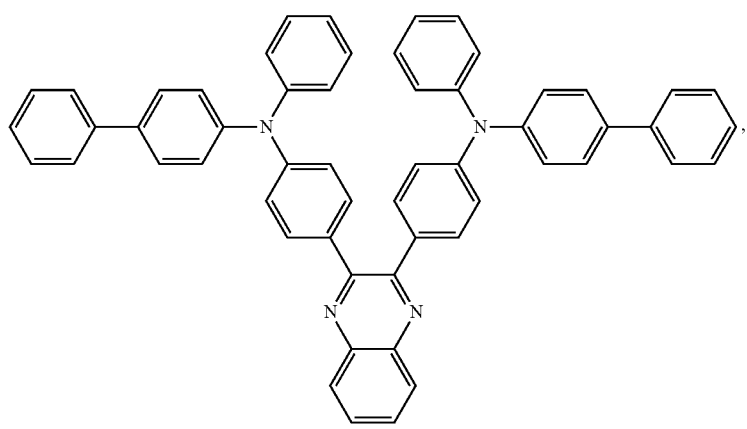

(abbreviation: BPAPQ)

-continued
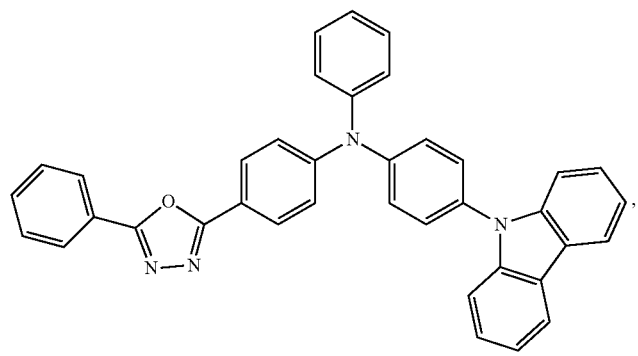
(abbreviation: YGA011)
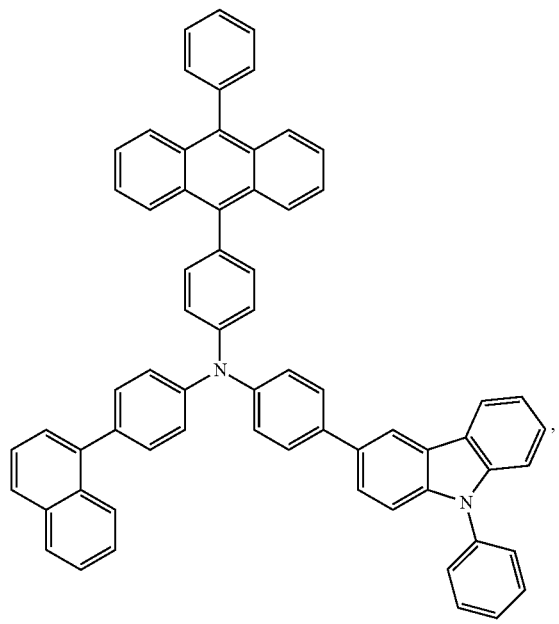
(abbreviation: PCBNAPA)
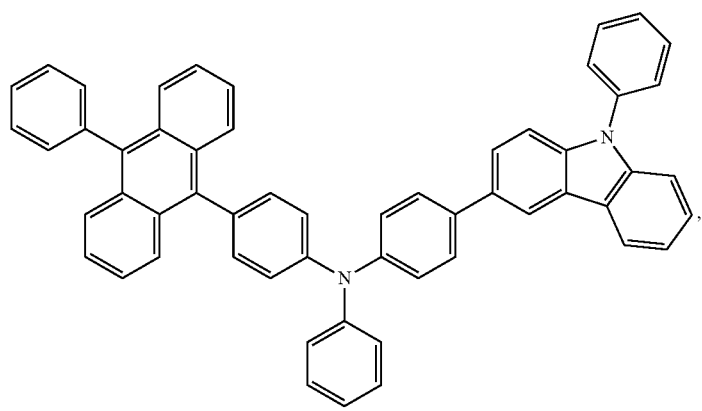
(abbreviation: PCBAPA)

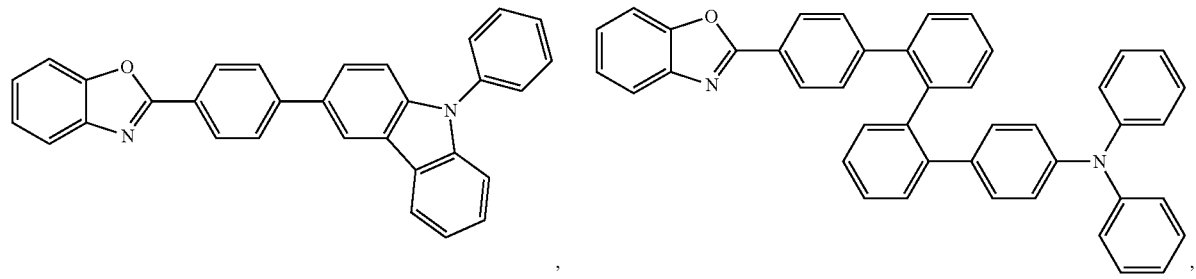
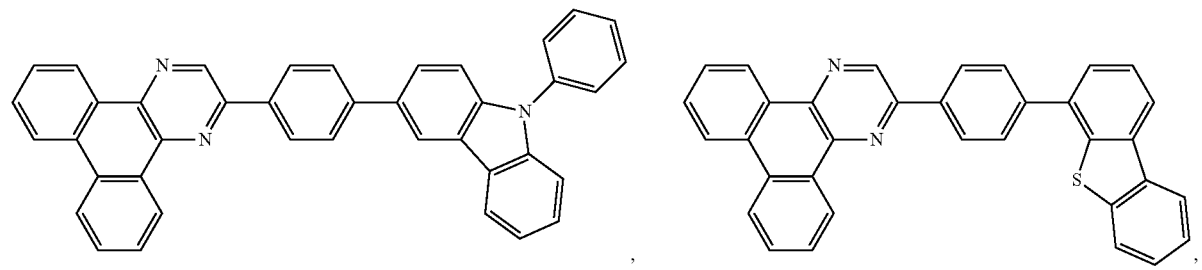
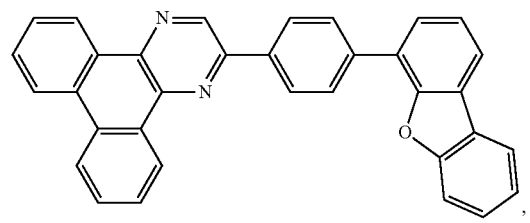
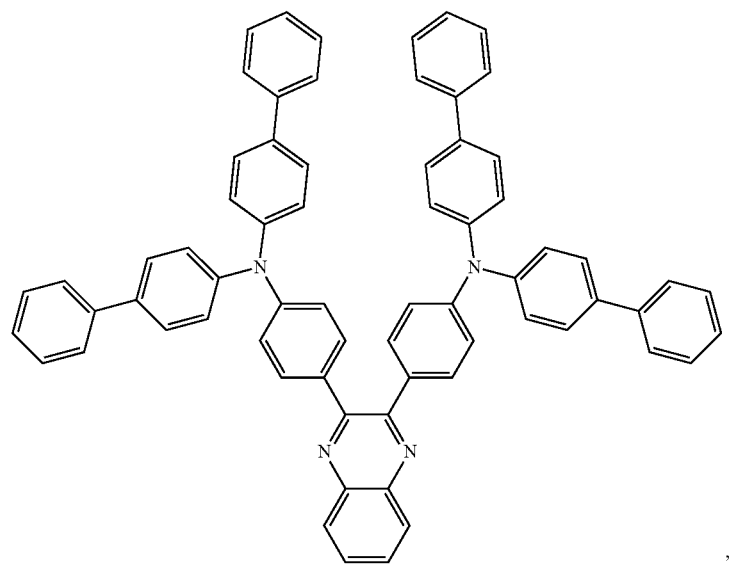

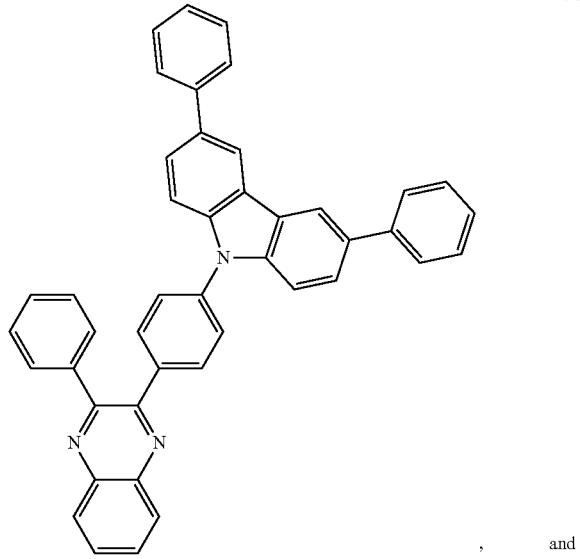

, and

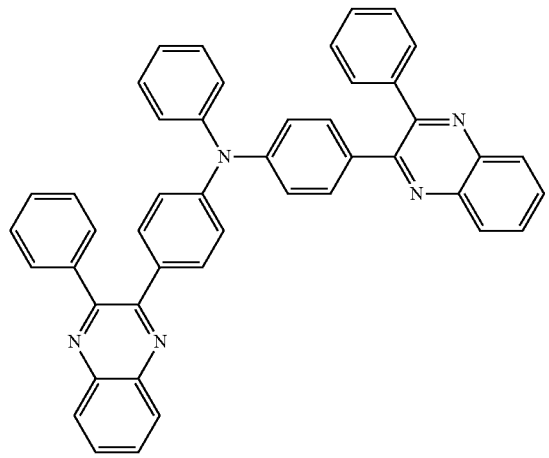

, can be used.

The light-emitting layer may comprise further components in addition to the emitter material. For example, a fluorescent dye may be present in the light-emitting layer in order to alter the emission color of the emitter material. In addition—in a preferred embodiment—a matrix material can be used. This matrix material may be a polymer, for example poly(N-vinylcarbazole) or polysilane. The matrix material may, however, be a small molecule, for example 4,4'-N,N'-dicarbazolebiphenyl (CDP=CBP) or tertiary aromatic amines, for example TCTA. In a preferred embodiment of the present invention, at least one compound of the formula 1 is used as matrix material.

A blocking layer for holes may be present. Examples of hole blocker materials typically used in OLEDs are 2,6-bis(N-carbazolyl)pyridine (mCPy), 2,9-dimethyl-4,7-diphenyl-1,10-phenanthroline (bathocuproin, (BCP)), bis(2-methyl-8-quinolinato)-4-phenyl-phenylato)aluminum(III) (BAlq), phenothiazine S,S-dioxide derivates and 1,3,5-tris(N-phenyl-2-benzylimidazolyl)benzene) (TPBI), TPBI also being suitable as electron-conducting material. Further suitable hole blockers and/or electron transport materials are 2,2',2"-(1,3,5-benzenetriyl)tris(1-phenyl-1-H-benzimidazole), 2-(4-biphenylyl)-5-(4-tert-butylphenyl)-1,3,4-oxadiazole, 8-hydroxyquinolinolatolithium, 4-(naphthalen-1-yl)-3,5-diphenyl-4H-1,2,4-triazole, 1,3-bis[2-(2,2'-bipyridin-6-yl)1,3,4-oxadiazo-5-yl]benzene,4,7-diphenyl-1,10-phenanthroline, 3-(4-biphenylyl)-4-phenyl-5-tert-butylphenyl-1,2,4-triazole, 6,6'-bis[5-(biphenyl-4-yl)-1,3,4-oxadiazo-2-yl]-2,2'-bipyridyl, 2-phenyl-9,10-di(naphthalene-2-yl)anthracene, 2,7-bis[2-(2,2'-bipyridin-6-yl)-1,3,4-oxadiazo-5-yl]-9,9-dimethylfluorene, 1,3-bis[2-(4-tert-butylphenyl)-1,3,4-oxadiazo-5-yl]benzene, 2-(naphthalene-2-yl)-4,7-di-phenyl-1,10-phenanthroline, tris(2,4,6-trimethyl-3-(pyridin-3-yl)phenyl)borane, 2,9-bis(naphthalene-2-yl)-4,7-diphenyl-1,10-phenanthroline, 1-methyl-2-(4-(naphthalene2-yl)phenyl)-1H-imidazo[4,5-f][1,10]phenanthroline. In a further embodiment, it is possible to use compounds which comprise aromatic or heteroaromatic rings joined via groups comprising carbonyl groups, as disclosed in WO2006/100298, disilyl compounds selected from the group consisting of disilylcarbazoles, disilylbenzofurans, disilylbenzothiophenes, disilylbenzophospholes, disilylbenzothiophene S-oxides and disilylbenzothiophene S,S-dioxides, as specified, for example, in PCT applications WO2009003919 and WO2009003898, which were yet to be published at the priority date of the present application, and disilyl compounds as disclosed in WO2008/034758, as a blocking layer for holes/excitons (4) or as matrix materials in the light-emitting layer (3).

Suitable electron transport materials for the layer (5) of the inventive OLEDs comprise metals chelated to oxinoid compounds, such as 2,2',2"-(1,3,5-phenylene)tris[1-phenyl-1H-benzimidazole] (TPBI), tris(8-quinolinolato)aluminum ($Alq_3$), compounds based on phenanthroline, such as 2,9-dimethyl-4,7-diphenyl-1,10-phenanthroline (DDPA=BCP) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), 8-hydroxyquinolinolatolithium (Liq), 4,7-diphenyl-1,10-phenanthroline (BPhen), bis(2-methyl-8-quinolinolato)-4-(phenylphenolato)aluminum (BAlq), 1,3-bis[2-(2,2'-bipyridin-6-yl)-1,3,4-oxadiazo-5-yl]benzene (Bpy-OXD), 6,6'-bis[5-(biphenyl-4-yl)-1,3,4-oxadiazo-2-yl]-2,2'-bipyridyl (BP-OXD-Bpy), 4-(naphthalen-1-yl)-3,5-diphenyl-4H-1,2,4-triazole (NTAZ), 2,9-bis(naphthalen-2-yl)-4,7-diphenyl-1,10-phenanthroline (NBphen), 2,7-bis[2-(2,2'-bipyridin-6-yl)-1,3,4-oxadiazo-5-yl]-9,9-dimethylfluorene (Bby-FOXD), 1,3-bis[2-(4-tertbutylphenyl)-1,3,4-oxadiazo-5-yl]benzene (OXD-7), tris(2,4,6-trimethyl-3-(pyridin-3-yl)phenyl)borane (3TPYMB), 1-methyl-2-(4-(naphthalen-2-yl)phenyl)-1H-imidazo[4,5-f][1,10]phenanthroline (2-NPIP), 2-phenyl-9,10-di(naphthalen-2-yl)anthracene (PADN),2-(naphthalene-2-yl)-4,7-diphenyl-1,10-phenanthroline (HN-Bphen). The layer (5) may serve both to facilitate electron transport and as a buffer layer or barrier layer in order to prevent quenching of the exciton at the interfaces of the layers of the OLED. The layer (5) preferably improves the mobility of the electrons and reduces quenching of the exciton. In a preferred embodiment, BCP is used as the electron transport material. In another preferred embodiment, the electron transport layer comprises at least one compound of the formula I as electron transport material.

Among the materials mentioned above as hole transport materials and electron transport materials, some may fulfil several functions. For example, some of the electron-conducting materials are simultaneously hole-blocking materials when they have a low-lying HOMO. These can be used, for example, in the blocking layer for holes/excitons (4). However, it is likewise possible that the function as a hole/exciton blocker is also adopted by the layer (5), such that the layer (4) can be dispensed with.

The charge transport layers can also be electronically doped in order to improve the transport properties of the materials used, in order firstly to make the layer thicknesses more generous (avoidance of pinholes/short circuits) and in order secondly to minimize the operating voltage of the device. For example, the hole transport materials can be doped can be doped with tetrafluorotetracyanquinodimethane (F4-TCNQ) or with $MoO_3$ or $WO_3$. The electron transport materials can be doped, for example, with alkali metals, for example $Alq_3$ with lithium. In addition, electron transports can be doped with salts such as $Cs_2CO_3$, or 8-hydroxyquinolato-lithium (Liq). Electronic doping is known to those skilled in the art and is disclosed, for example, in W. Gao, A. Kahn, J. Appl. Phys., Vol. 94, No. 1,1 Jul. 2003 (p-doped organic layers); A. G. Werner, F. Li, K. Harada, M. Pfeiffer, T. Fritz, K. Leo. Appl. Phys. Lett., Vol. 82, No. 25,23 Jun. 2003 and Pfeiffer et al., Organic Electronics 2003, 4, 89-103. For example, the hole transport layer may, in addition to a carbene complex, e.g. $Ir(dpbic)_3$, be doped with $MoO_3$ or $WO_3$. For example, the electron transport layer may comprise BCP doped with $Cs_2CO_3$.

The cathode (6) is an electrode which serves to introduce electrons or negative charge carriers. Suitable materials for the cathode are selected from the group consisting of alkali metals of group Ia, for example Li, Cs, alkaline earth metals of group IIa, for example calcium, barium or magnesium, metals of group IIb of the periodic table of the elements (old IUPAC version), comprising the lanthanides and actinides, for example samarium. In addition, it is also possible to use metals such as aluminum or indium, and combinations of all metals mentioned. In addition, alkali metal-comprising organometallic compounds, or alkali metal fluorides, such as, for example, LiF, CsF, or KF, can be applied between the organic layer and the cathode in order to reduce the operating voltage.

The OLED according to the present invention may additionally comprise further layers which are known to those skilled in the art. For example, a layer which facilitates the transport of the positive charge and/or matches the band gaps of the layers to one another may be applied between the layer (2) and the light-emitting layer (3). Alternatively, this further layer may serve as a protective layer. In an analogous manner, additional layers may be present between the light-emitting layer (3) and the layer (4) in order to facilitate the transport of negative charge and/or to match the band gaps between the layers to one another. Alternatively, this layer may serve as a protective layer.

In a preferred embodiment, the inventive OLED, in addition to layers (1) to (6), comprises at least one of the following layers mentioned below:
 a hole injection layer between the anode (1) and the hole-transporting layer (2) having a thickness of 2 to 100 nm, preferably 5 to 50 nm;
 a blocking layer for electrons between the hole-transporting layer (2) and the light-emitting layer (3);
 an electron injection layer between the electron-transporting layer (5) and the cathode (6).

Materials for a hole injection layer may be selected from copper phthalocyanine, 4,4',4"-tris(N-3-methylphenyl-N-phenylamino)triphenylamine (m-MTDATA), 4,4',4"-tris(N-(2-naphthyl)-N-phenylamino)triphenylamine (2T-NATA), 4,4',4"-tris(N-(1-naphthyl)-N-phenylamino)triphenylamine (1T-NATA), 4,4',4"-tris(N,N-diphenylamino)triphenylamine (NATA), titanium oxide phthalocyanine, 2,3,5,6-tetrafluoro-7,7,8,8-tetracyanoquino-dimethane (F4-TCNQ), pyrazino[2,3-f][1,10]phenanthroline-2,3-dicarbonitrile (PPDN), N,N,N',N'-tetrakis(4-methoxyphenyl)benzidine (MeO-TPD), 2,7-bis[N,N-bis(4-methoxy-phenyl)amino]-9,9-spirobifluorene (MeO-Spiro-TPD), 2,2'-bis[N,N-bis(4-methoxy-phenyl) amino]-9,9-spirobifluorene (2,2'-MeO-Spiro-TPD), N,N'-di phenyl-N,N'-di-[4-(N,N-ditolylamino) phenyl]benzidine (NTNPB), N,N'-diphenyl-N ,N-di-[4-(N,N-diphenyl-amino)phenyl]benzidine (NPNPB), N,N'-di(naphthalen-2-yl)-N,N'-diphenylbenzene-1,4-diamine (α-NPP). In principle, it is possible that the hole injection layer comprises at least one compound of the formula I as hole injection material. In addition, polymeric hole-injection materials can be used such as poly(N-vinylcarbazole) (PVK), polythiophenes, polypyrrole, polyaniline, self-doping polymers, such as, for example, sulfonated poly(thiophene-3[2[(2-methoxyethoxy)ethoxy]-2,5-diyl) (Plexcore$^3$ OC Conducting Inks commercially available from Plextronics), and copolymers such as poly(3,4-ethylenedioxythiophene)/poly(4-styrenesulfonate) also called PEDOT/PSS.

As a material for the electron injection layer, LiF, for example, can be selected.

In addition, it is possible that some of the layers used in the inventive OLED have been surface-treated in order to increase the efficiency of charge carrier transport.

The inventive OLED can be produced by methods known to those skilled in the art. In general, the inventive OLED is produced by successive vapor deposition of the individual layers onto a suitable substrate. Suitable substrates are, for example, glass, inorganic semi-conductors or polymer films. For vapor deposition, it is possible to use customary techniques, such as thermal evaporation, chemical vapor deposition (CVD), physical vapor deposition (PVD) and others. In an alternative process, the organic layers of the OLED can be applied from solutions or dispersions in suitable solvents, employing coating techniques known to those skilled in the art.

In general, the different layers have the following thicknesses: anode (1) 50 to 500 nm, preferably 100 to 200 nm; hole-conducting layer (2) 5 to 100 nm, preferably 20 to 80 nm, light-emitting layer (3) 1 to 100 nm, preferably 10 to 80 nm, blocking layer for holes/excitons (4) 2 to 100 nm, preferably 5 to 50 nm, electron-conducting layer (5) 5 to 100 nm, preferably 20 to 80 nm, cathode (6) 20 to 1000 nm, preferably 30 to 500 nm. The relative position of the recombination zone of holes and electrons in the inventive OLED in relation to the cathode and hence the emission spectrum of the OLED can be influenced, among other factors, by the relative thickness of each layer. This means that the thickness of the electron transport layer should preferably be selected such that the position of the recombination zone is matched to the optical resonator property of the diode and hence to the emission wavelength of the emitter. The ratio of the layer thicknesses of the individual layers in the OLED depends on the materials used. It is possible that the electron-conducting layer and/or the hole-conducting layer have greater thicknesses than the layer thicknesses specified when they are electrically doped.

Use of the compounds of the formula I in at least one layer of the OLED, preferably in the light-emitting layer (preferably as an emitter material) makes it possible to obtain OLEDs with high efficiency and with low use and operating voltage. Frequently, the OLEDs obtained by the use of the compounds of the formula I additionally have high lifetimes. The efficiency of the OLEDs can additionally be improved by optimizing the other layers of the OLEDs. For example, high-efficiency cathodes such as Ca or Ba, if appropriate in combination with an intermediate layer of LiF, can be used. Shaped substrates and hole-transporting materials which bring about a reduction in the operating voltage or an increase in the quantum efficiency are likewise usable in the inventive OLEDs. Moreover, additional layers may be present in the OLEDs in order to adjust the energy level of the different layers and to facilitate electroluminescence.

The OLEDs may further comprise at least one second light-emitting layer. The overall emission of the OLEDs may be composed of the emission of the at least two light-emitting layers and may also comprise white light.

The OLEDs can be used in all apparatus in which electroluminescence is useful. Suitable devices are preferably selected from stationary and mobile visual display units and illumination units. Stationary visual display units are, for example, visual display units of computers, televisions, visual display units in printers, kitchen appliances and advertising panels, illuminations and information panels. Mobile visual display units are, for example, visual display units in cellphones, laptops, digital cameras, MP3 players, vehicles and destination displays on buses and trains. Further devices in which the inventive OLEDs can be used are, for example, keyboards; items of clothing; furniture; wallpaper.

In addition, the present invention relates to a device selected from the group consisting of stationary visual display units such as visual display units of computers, televisions, visual display units in printers, kitchen appliances and advertising panels, illuminations, information panels, and mobile visual display units such as visual display units in cellphones, laptops, digital cameras, MP3 players, vehicles and destination displays on buses and trains; illumination units; keyboards; items of clothing; furniture; wallpaper, comprising at least one inventive organic light-emitting diode or at least one inventive light-emitting layer.

The following examples illustrate certain features and advantages of the present invention. They are intended to be illustrative of the invention, but not limiting. All percentages are by weight, unless otherwise indicated.

EXAMPLES

Ligand Example 1

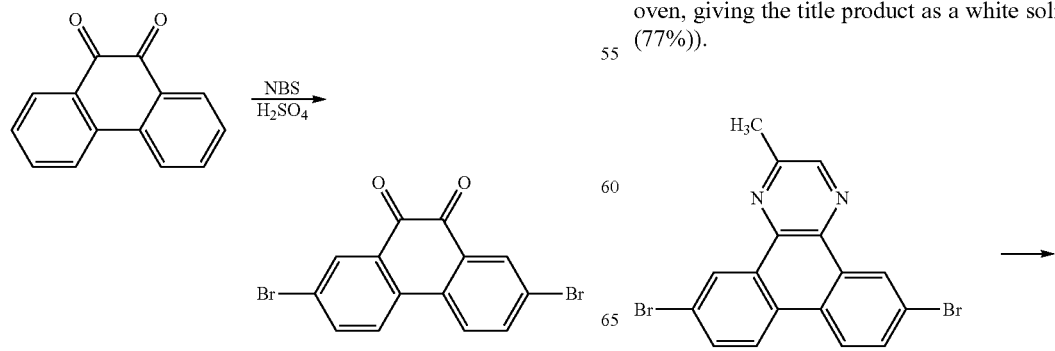

a) 104 g (0.50 mol) of 9,10-dioxophenanthrene are suspended under nitrogen in 2000 ml of sulfuric acid and treated in small portions with a total of 182.5 g (1.03 mol) of N-bromosuccinimide during one hour at a temperature below 40° C. The resulting red brown viscous reaction mass is stirred at room temperature for four hours. The reaction mixture is slowly dropped into 6000 ml of an ice-water mixture under slow stirring. The resulting orange suspension is filtered and the solid washed with 5000 ml of water and 2000 ml of ethanol, and then dried under vacuum at 70° C. The orange solid is dissolved in 2100 ml N,N-dimethylformamide (DMF) under reflux and further stirred at 80° C. for one hour. The resulting suspension is filtered at 80° C. and the solid washed with 1000 ml of DMF and 600 ml of methanol, followed by drying under vacuum at 80° C., giving the title product as a red powder (yield: 96.8 g (53%)). Melting point: 284-285° C.

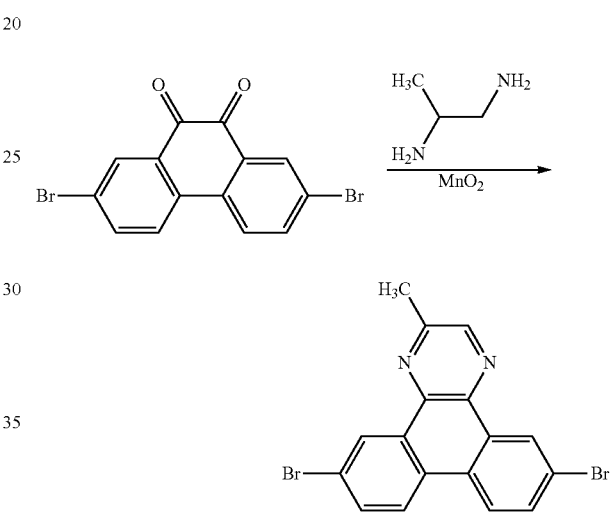

b) 7.9 g (0.11 mol) of 1,2-diaminopropane are added under nitrogen to 32.6 g (0.09 mol) of 2,7-dibromo-9,10-phenanthrenedione in 2000 ml of toluene. The red suspension is heated under reflux for 2 h using a water separator. The resulting brownish suspension is treated with 40 g of manganese(IV)oxide at 94° C., and heating continued under reflux until no intermediate product is visible anymore on the TLC. The hot black suspension is filtered through silica gel (5 cm layer) using a preheated funnel, and the silica gel layer rinsed with 800 ml of hot toluene. A solid immediately precipitates out from the filtrate and is further washed with a small amount of toluene, followed by drying in a vacuum oven, giving the title product as a white solid (yield: 27.7 g (77%)).

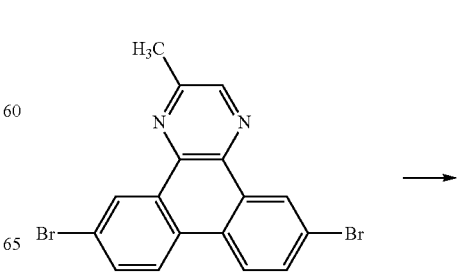

-continued

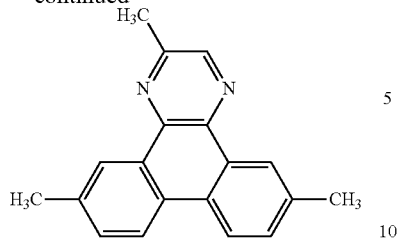

c) 11.1 g (27.6 mmol) of 6,11-dibromo-2-methyldibenzo[f,h]guinoxaline (product of Ligand Example 1b), and 4.97 g (83 mmol) of methylboronic acid are suspended under argon in 70 ml of dioxane and 200 ml of toluene. 0.12 g (0.53 mmol) of palladium(II) acetate and 1.36 g (3.3 mmol) of 2-dicyclohexyl-phosphino-2',6'-dimethoxybiphenyl are added, and the reaction mixture is degassed with argon. A degassed solution of 63.6 g (0.28 mol) of potassium phosphate hydrate in 70 ml of water is added. The yellow suspension is heated under reflux for five hours. The resulting grey emulsion is filtered through Hyflo and the filter cake washed with toluene. The organic phase is separated, further washed three times with 200 ml of water, and concentrated under vacuum. The resulting solid is recrystallized three times from ethanol providing the title product as light white solid (yield: 1.9 g (25%)). Melting point: 176-178° C. $^1$H-NMR (400 MHz, CDCl$_3$): δ=2.64 (s, 3 H), 2.65 (s, 3 H), 2.86 (s, 3 H), 7.55-7.62 (m, 2 H), 8.47 (d, 2 H), 8.76 (s, 1 H), 8.95 (s, 1 H), 9.02 (s, 1 H).

Ligand Example 2

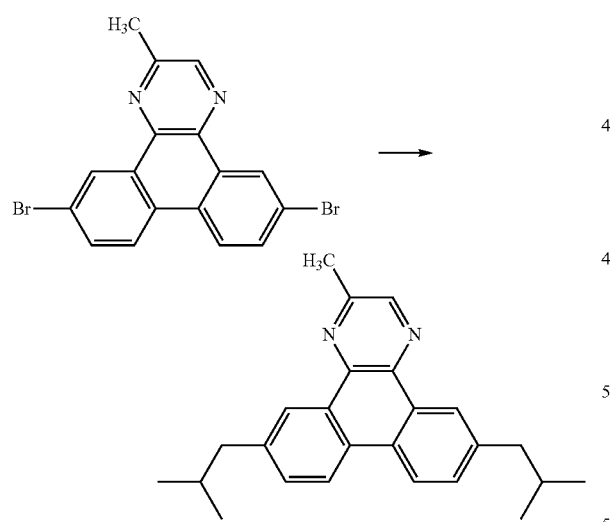

6.03 g (15.0 mmol) of 6,11-dibromo-2-methyldibenzo[f,h]guinoxaline (product of Ligand Example 1b), and 4.58 g (44.9 mmol) of (2-methylpropyl)boronic acid are suspended under argon in 200 ml of toluene. 0.13 g (0.58 mmol) of palladium(II) acetate and 0.74 g (1.8 mmol) of 2-dicyclohexyl-phosphino-2',6'-dinnethoxybiphenyl are added, followed by the addition of 34.5 g (0.15 mol) of potassium phosphate hydrate. The reaction mixture is degassed with argon and the light yellow suspension heated under reflux for three hours. The hot grey suspension is filtered through silica gel (2 cm layer), and the silica gel layer rinsed with toluene. The collected eluents are concentrated under vacuum and the resulting solid recrystallized from ethanol, giving the title product as a white solid (yield: 4.3 g (80.4%)). Melting point: 129-130° C. $^1$H-NMR (300 MHz, CDCl$_3$): δ=0.98 (d, 6 H), 1.00 (d, 6 H), 1.99-2.17 (m, 2 H), 2.76 (dd, 4 H), 2.84 (s, 3 H), 7.52-7.59 (m, 2 H), 8.50 (d, 2 H), 8.76 (s, 1 H), 8.92 (d, 1 H), 9.00 (d, 1 H).

Ligand Example 3

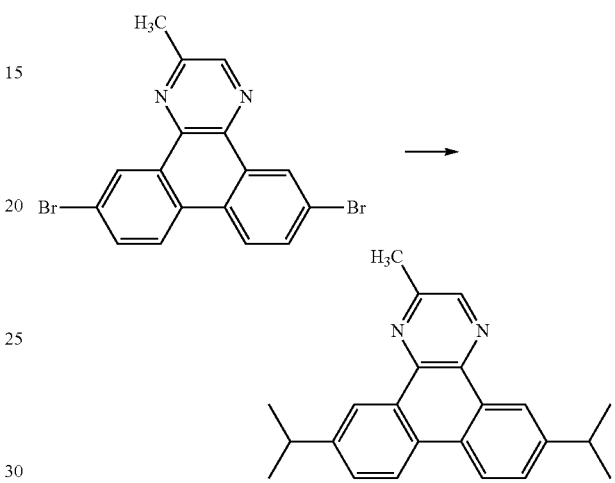

The title product is prepared according to the procedure of Ligand Example 2, with 6,11-dibromo-2-methyldibenzo[f,h]quinoxaline (product of Ligand Example 1b), giving the title product as a white solid after recrystallization from ethanol.

Ligand Example 4

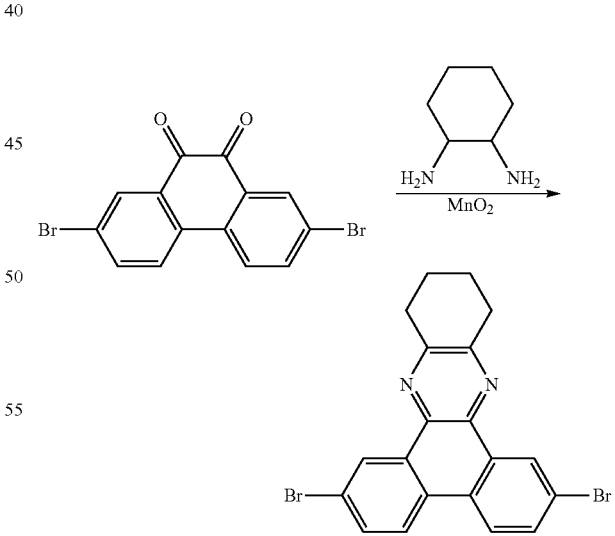

a) 13.7 g (0.12 mol) of 1,2-diaminocyclohexane are added under nitrogen to 36.6 g (0.10 mol) of 2,7-dibromo-9,10-phenanthrenedione in 1000 ml of toluene. The red suspension is heated under reflux for one hour using a water separator. The resulting brownish suspension is diluted by the addition of 1000 ml toluene and treated with 75 g of manganese (IV)oxide at 84° C., and heating continued under reflux until no intermediate product is visible anymore on the TLC. The hot black suspension is filtered through silica gel (5 cm layer) using a preheated funnel, and the silica gel layer rinsed with 500 ml of hot toluene. The combined filtrates are concentrated and the resulting solid dried under vacuum, giving the title product as a white solid (yield: 42.3 g (96%)). Melting point: 253-254° C. $^1$H-NMR (400 MHz, CDCl$_3$): δ=2.07-2.15 (m, 4 H), 3.15-3.26 (m, 4 H), 7.74 (dd, 2 H), 8.22 (d, 2 H), 9.15 (d, 2 H).

temperature to a suspension of 16.0 g (0.42 mol) of lithium aluminium hydride in 250 ml of anhydrous THF. The temperature is slowly increased up to reflux and stirring continued for eight hours. The grey suspension is cooled down to room temperature, 30 ml of water are slowly added, the suspension filtered through Hyflo, followed by extensive washing of Hylo with THF. The combined filtrates are concentrated giving 18.4 g of crude product. Further distillation provided a pure fraction of the title product at a temperature of 86-95° C. at 50 mbar, as a colourless oil (12.1 g (54%)). $^1$H-NMR (300 MHz, CDCl$_3$): δ=0.90 (d, 3H), 0.93 (d, 3 H), 1.18-1.22 (m, 2 H), 1.38 (br. s, 4 H), 1.69-1.79 (m, 1 H), 2.38-2.48 (m, 1 H), 2.67-2.79 (m, 2 H).

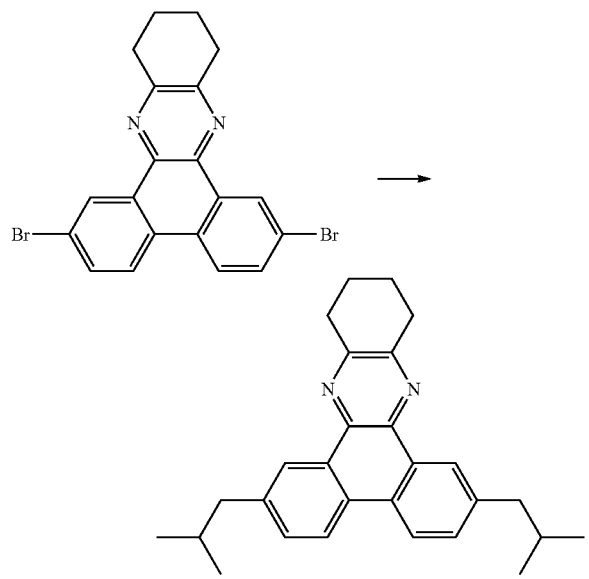

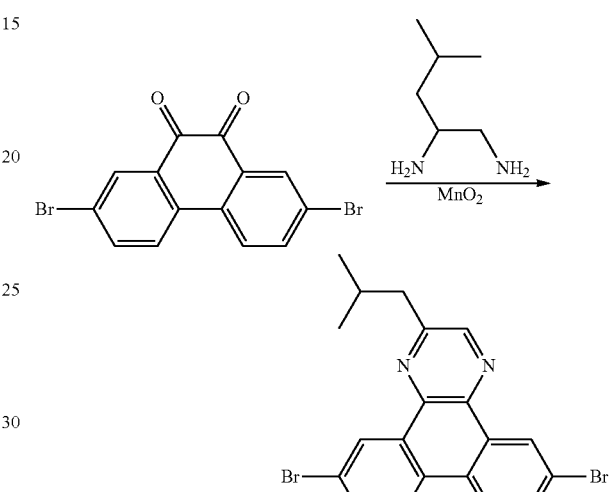

b) 6.63 g (15.0 mmol) of 6,11-dibromo-2-methyldibenzo[f,h]quinoxaline (product of Ligand Example 4a), and 4.58 g (44.9 mmol) of (2-methylpropyl)boronic acid are suspended under argon in 200 ml of toluene. 0.13 g (0.58 mmol) of palladium(II) acetate and 0.74 g (1.8 mmol) of 2-dicyclohexyl-phosphino-2',6'-dinnethoxybiphenyl are added, followed by the addition of 34.5 g (0.15 mol) of potassium phosphate hydrate. The reaction mixture is degassed with argon and the light yellow suspension heated under reflux for two hours. The hot grey suspension is filtered through silica gel (2 cm layer), and the silica gel layer rinsed with toluene. The collected eluents are concentrated under vacuum and the resulting solid recrystallized from ethanol, giving the title product as a white solid (yield: 4.3 g (72%)). Melting point: 211-212° C. $^1$H-NMR (300 MHz, CDCl$_3$): δ=0.99 (d, 12 H), 1.99-2.16 (m, 6 H), 2.75 (d, 4 H), 3.17-3.28 (m, 4 H), 7.51 (dd, 2 H), 8.47 (d, 2 H), 8.93 (d, 2 H).

b) 6.4 g (55 mmol) of the product of Ligand Example 5a are added under nitrogen to 36.6 g (50 mmol) of 2,7-dibromo-9,10-phenanthrenedione in 100 ml of toluene. The orange-red suspension is heated under reflux for two hours using a water separator. The resulting orange-yellow is treated with 20 g of manganese(IV)oxide at 95° C., and heating continued under reflux until no intermediate product is visible anymore on the TLC. The hot black suspension is filtered through Hyflo (5 cm layer) using a preheated funnel, and the Hyflo layer rinsed with hot toluene. The filtrate is cooled down to room temperature and the solid filtered off, giving a first fraction of 12.1 g of a white solid. The filtrate is concentrated giving an additional 10.2 g of a white solid. The two solid fractions are combined and suspended in hot toluene, followed by filtration at room temperature giving the title product as a white solid (yield: 12.4 g (56%)). Melting point: 217-218° C. $^1$H-NMR (300 MHz, CDCl$_3$): δ=1.06 (d, 6 H), 2.28-2.49 (m, 1 H), 2.96 (d, 2 H), 7.81-7.87 (m, 2 H), 8.38 (dd, 2 H), 8.74 (s, 1 H), 9.29 (d, 1 H), 9.35 (d, 1 H).

Ligand Example 5

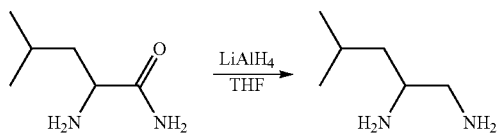

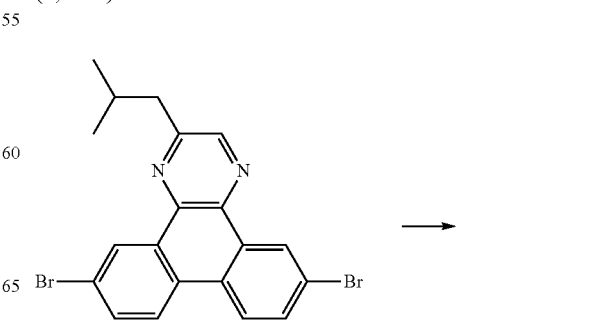

a) 25.0 g (0.19 mol) of leucinannide (H-Leu-NH2) is added in small portions under a nitrogen stream at room

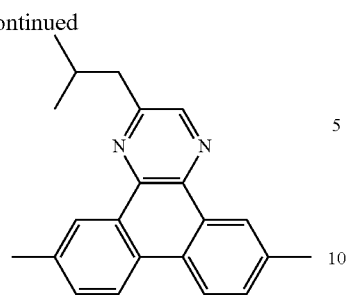

c) 3.7 g (8.3 mmol) of the product of Ligand Example 5b), and 1.5 g (25.1 mmol) of (2-methylpropyl)boronic acid are suspended under argon in 150 ml of toluene. 74 mg (0.33 mmol) of palladium(II) acetate and 0.37 g (0.90 mmol) of 2-dicyclohexyl-phosphino-2',6'-dimethoxybiphenyl are added, followed by the addition of 19.2 g (83.4 mmol) of potassium phosphate hydrate. The reaction mixture is degassed with argon and the light yellow suspension heated under reflux for 27 h. The hot grey suspension is filtered through silica gel (2 cm layer), and the silica gel layer rinsed with toluene. The collected eluents are concentrated under vacuum and the resulting solid recrystallized from ethanol, giving the title product as a white solid (yield: 2.2 g (71%)). Melting point: 211-212° C.

Ligand Example 6

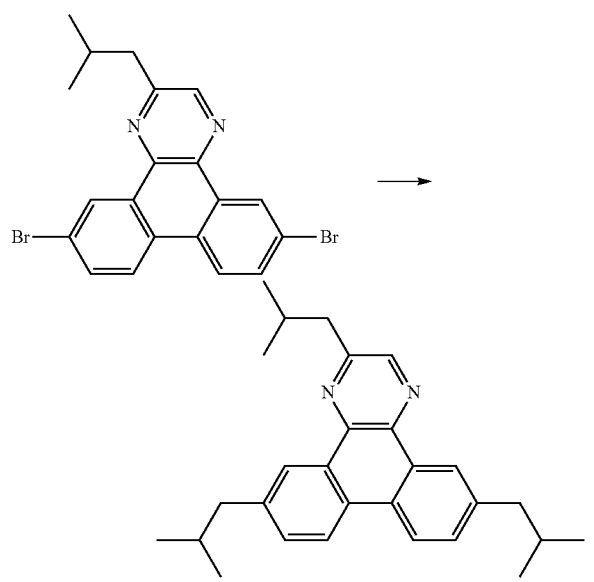

4.4 g (8.3 mmol) of the product of Ligand Example 1b), and 3.06 g (30.0 mmol) of (2-methylpropyl) boronic acid are suspended under argon in 150 ml of toluene. 90 mg (0.40 mmol) of palladium(II) acetate and 0.5 g (1.22 mmol) of 2-dicyclohexyl-phosphino-2',6'-dimethoxybiphenyl are added, followed by the addition of 23 g (99.9 mmol) of potassium phosphate hydrate. The reaction mixture is degassed with argon and the light yellow suspension heated under reflux for three hours. The hot grey suspension is filtered through silica gel (2 cm layer), and the silica gel layer rinsed with toluene. The collected eluents are concentrated under vacuum and the resulting solid recrystallized from ethanol, giving the title product as a white solid (yield: 2.9 g (73%)). Melting point: 129-130° C. $^1$H-NMR (300 MHz, CDCl$_3$): δ=0.99 (d, 6 H), 1.00 (d, 6 H), 1.06 (d, 6 H), 2.00-2.16 (m, 2 H), 2.29-2.44 (m, 1 H), 2.76 (dd, 4 H), 2.96 (d, 2 H), 7.52-7.59 (m, 2 H), 7.00 (d, 2 H), 8.71 (s, 1 H), 8.93 (d, 1 H), 9.02 (d, 1 H).

Ligand Example 7

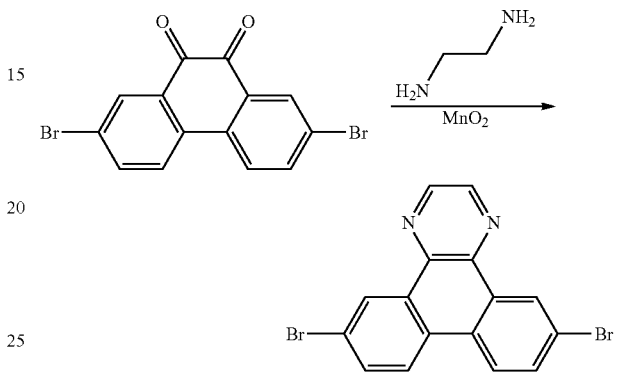

a) 7.2 g (0.12 mol) of 1,2-diaminoethane are added under nitrogen to 36.6 g (0.10 mol) of 2,7-dibromo-9,10-phenanthrenedione in 1000 ml of toluene. The red suspension is heated under reflux for one hour using a water separator. The resulting brownish suspension is diluted with 1000 ml of toluene and treated with 25 g of manganese(IV)oxide at 84° C., and heating continued under reflux until no intermediate product is visible anymore on the TLC (one hour reaction time). The hot black suspension is filtered through silica gel (5 cm layer) using a preheated funnel, and the silica gel layer rinsed with 500 ml of hot toluene. A solid immediately precipitates out from the filtrate and is further washed with a small amount of cold toluene, followed by drying in a vacuum oven, giving the title product as a white solid (yield: 30.9 g (80%)). $^1$H-NMR (400 MHz, CDCl$_3$): δ=7.91 (d, 2 H), 8.45 (d, 2 H), 8.96 (s, 2 H), 9.39 (s, 2 H).

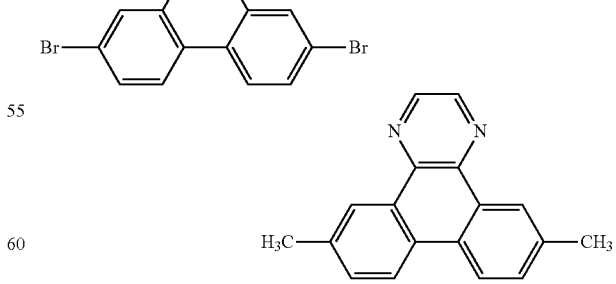

b) The title product is prepared according to the procedure of Ligand Example 6, with 6, 11-dibromodibenzo[f,h]quinoxaline (product of Ligand Example 7a), giving the title product as a white solid after recrystallization from ethanol.

Ligand Example 8

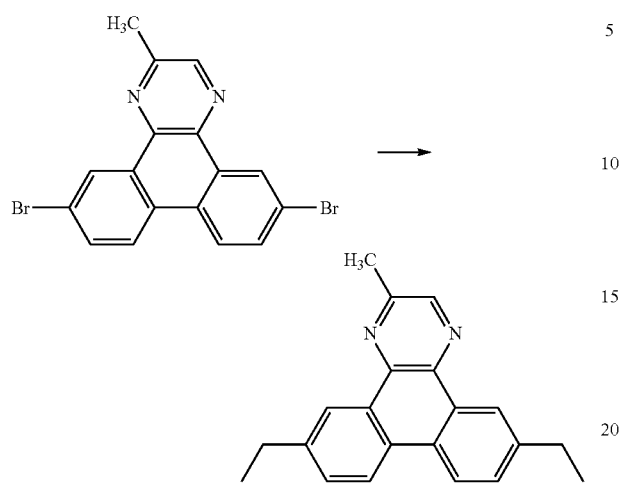

12.06 g (30.0 mmol) of 6,11-dibromo-2-methyldibenzo[f,h]quinoxaline (product of Ligand Example 1b), and 6.65 g (90.0 mmol) of ethylboronic acid are suspended under argon in 200 ml of toluene. 0.27 (1.20 mmol) of palladium (II) acetate and 1.47 g (3.58 mmol) of 2-dicyclohexyl-phosphino-2',6'-dimethoxybiphenyl are added, followed by the addition of 69 g (0.30 mol) of potassium phosphate hydrate. The reaction mixture is degassed with argon and the light yellow suspension heated under reflux for two hours. The hot grey suspension is filtered through silica gel (2 cm layer), and the silica gel layer rinsed with toluene. The collected eluents are concentrated under vacuum and the resulting solid recrystallized three times from ethanol providing the title product as a light beige powder (yield: 4.98 g (55%)). Melting point: 139-140° C. $^1$H-NMR (400 MHz, CDCl$_3$): δ=1.44 (dt, 6 H), 2.85 (s, 3 H), 2.96 (dq, 4 H), 7.57-7.63 (m, 2 H), 8.48 (d, 2 H), 8.75 (s, 1 H), 9.51 (dd, 2 H).

Ligand Example 9

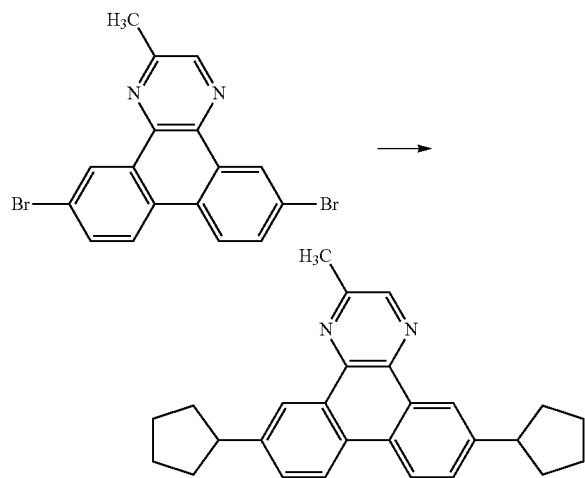

The title product is prepared according to the procedure of Ligand Example 6, with 6,11-dibromo-2-methyldibenzo[f,h]quinoxaline (product of Ligand Example 1b)), giving the title product as a white solid after recrystallization from ethanol.

Ligand Example 10

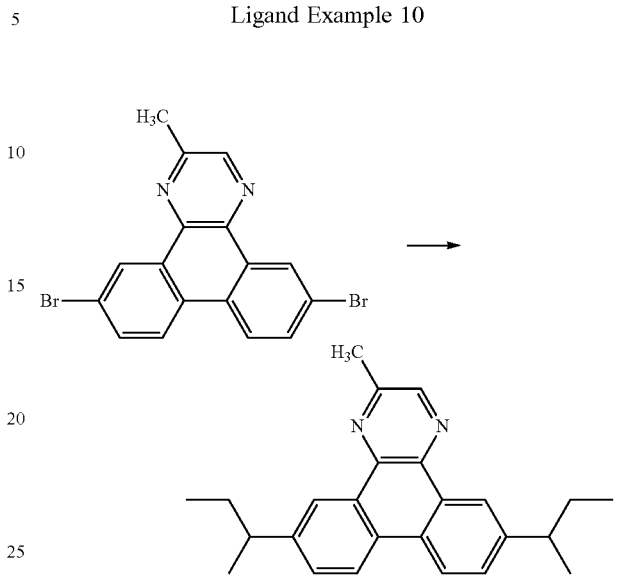

The title product is prepared according to the procedure of Ligand Example 6, with 6,11-dibromo-2-methyldibenzo[f,h]quinoxaline (product of Ligand Example 1b), giving the title product as a white solid after recrystallization from ethanol.

Ligand Example 11

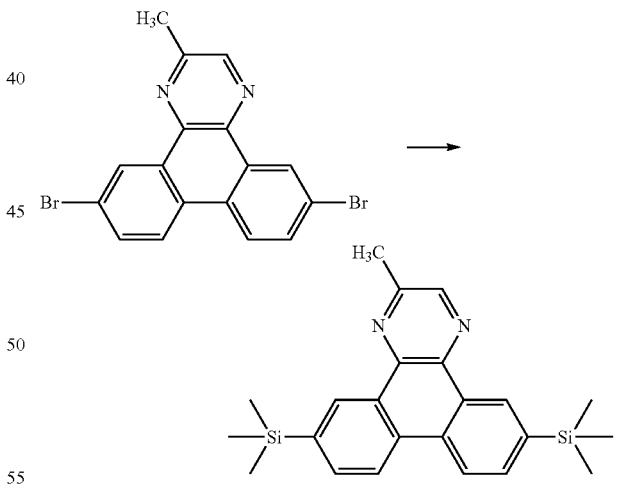

4.02 g (10.0 mmol) of 6,11-dibromo-2-methyldibenzo[f,h]quinoxaline (product of Ligand Example 1b), and 3.5 g (23.6 mmol) of hexamethyldisilane are suspended under argon in 100 ml DMF and 0/2 g of water. 0.09 g (0.01 mmol) of tris(dibenzylideneacetone)dipalladium(0) and 0.06 g (0.18 mmol) of2-di-tert-butylphosphino-2'-(N,N-dimethylamino)biphenyl are added, followed by the addition of 3.3 g (50 mmol) of lithium acetate. The reaction mixture is degassed with argon and the light yellow suspension heated at 100° C. for 21 h. The hot grey suspension is treated with an additional 3.5 g of hexamethyldisilane and heating continued at 109° C. for 4 h, followed by addition of the same amount of hexamethyldisilane and heating at 109° C. for two hours. The grey suspension is filtered through silica gel (2 cm layer), and the silica gel layer rinsed with 100 ml of DMF giving a clear yellow filtrate. The filtrate is treated with water until a beige suspension is obtained. The resulting solid is filtered off and dissolved in 200 ml of a 1:1-mixture of hot ethanol/isopropanol. The turbid mixure is filtered, cooled down to room temperature and treated with 5 ml of water providing a beige suspension. Filtration and drying in a vacuum oven gives the title product as a light beige solid. (yield: 1.9 g (49%)).

Ligand Example 12

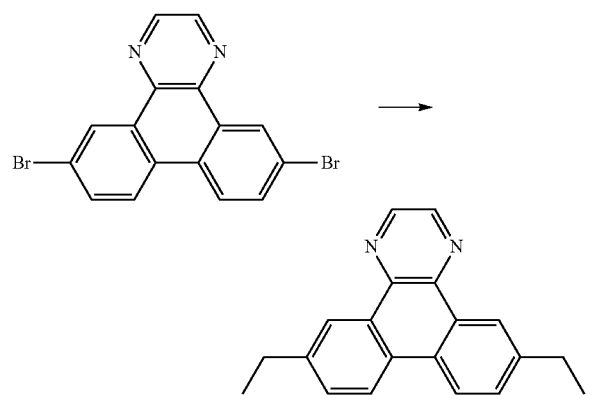

8.53 g (22.0 mmol) of 6,11-dibromodibenzo[f,h]quinoxaline (product of Ligand Example 7a), and 4.90 g (66.3 mmol) of ethylboronic acid are suspended under argon in 300 ml of toluene. 0.2 (0.89 mmol) of palladium(II) acetate and 1.08 g (2.63 mmol) of2-dicyclohexyl-phosphino-2',6'-dimethoxybiphenyl are added, followed by the addition of 50 g (0.22 mol) of potassium phosphate hydrate. The reaction mixture is degassed with argon and the light yellow suspension heated under reflux for two hours. The hot grey suspension is filtered through silica gel (2 cm layer), and the silica gel layer rinsed with toluene. The collected eluents are concentrated under vacuum and the resulting solid recrystallized from ethanol providing the title product as a light beige powder (yield: 2.6 g (41%)).

Ligand Example 13

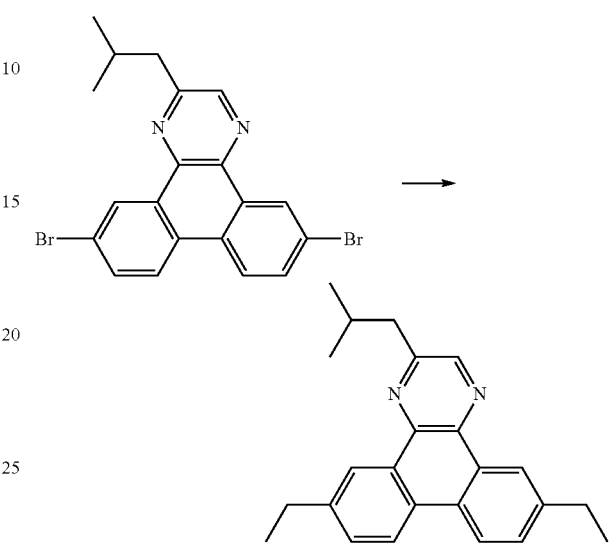

5.7 g (12.8 mmol) of the product of Ligand Example 5b), and 2.9 g (39.3 mmol) of ethylboronic acid are suspended under argon in 200 ml of toluene. 0.11 g (0.49 mmol) of palladium (II) acetate and 0.63 g (1.53 mmol) of 2-dicyclohexyl-phosphino-2',6'-dimethoxy-biphenyl are added, followed by the addition of 29.5 g (128.1 mmol) of potassium phosphate hydrate. The reaction mixture is degassed with argon and the light yellow suspension heated under reflux for three hours. The hot grey suspension is filtered through silica gel (2 cm layer), and the silica gel layer rinsed with toluene. The collected eluents are concentrated under vacuum and the resulting solid recrystallized from ethanol, giving the title product as a white solid (yield: 3.3 g (73%)). Melting point: 99-100° C. $^1$H-NMR (400 MHz, CDCl$_3$): δ=1.09 (d, 6 H), 1.44 (dt, 6 H), 2.34-2A7 (m, 1 H), 2.92-3.02 (m, 6 H), 7.61-7.67 (m, 2 H), 8.54 (d, 2 H), 8.75 (s, 1 H), 9.02 (d, 1 H), 9.10 (d, 1 H).

Diiridium Complex Example 1

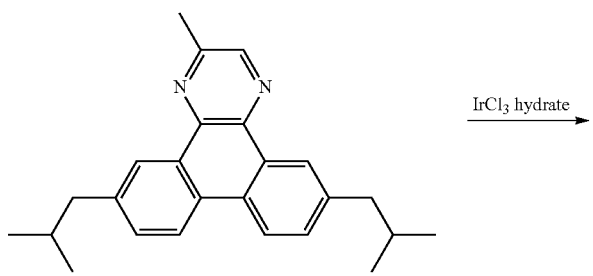

-continued

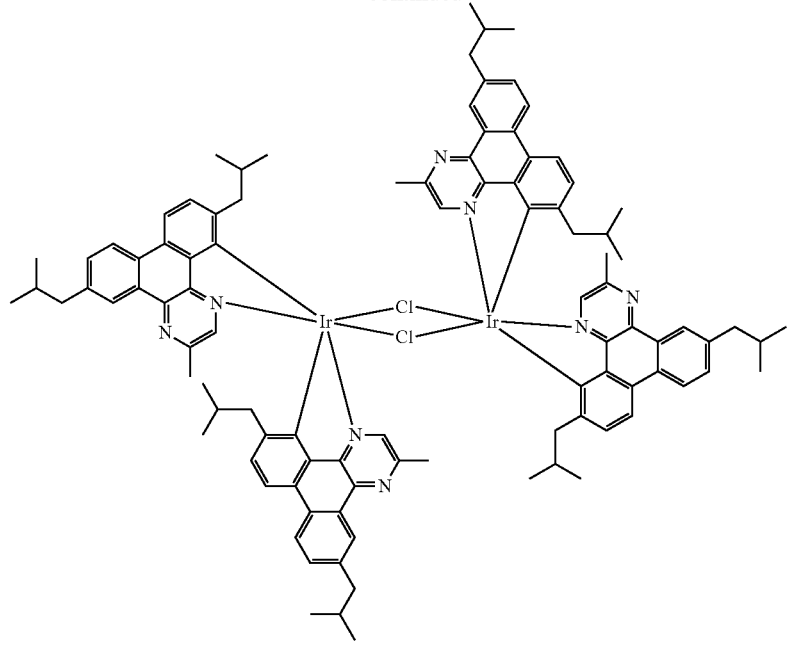

3.56 (10 mmol) of the product of Ligand Example 2 and 1.73 g (4.8 mmol) of iridium (III)chloride hydrate (53.01% iridium-content) are suspended at room temperature under nitrogen in 50 ml of 2-ethoxyethanol. The yellow suspension is heated up to 116° C. and kept at this temperature for 17 h. The red suspension is filtered, washed with ethanol first, followed by hexane, and further dried under vacuum, giving the title product as bright red powder (yield: 4.3 g (96%)).

Diiridium Complex Examples 2-7

The following diiridium complexes are prepared according to the procedure reported for Diiridium Complex Example 1, giving the products of Diiridium Complex Examples 2-6. The respective product structures have been confirmed by HPLC-MS measurements.

| Diiridium Complex Example | Ligand Example | Diiridium complex |
|---|---|---|
| 1 | 2 | 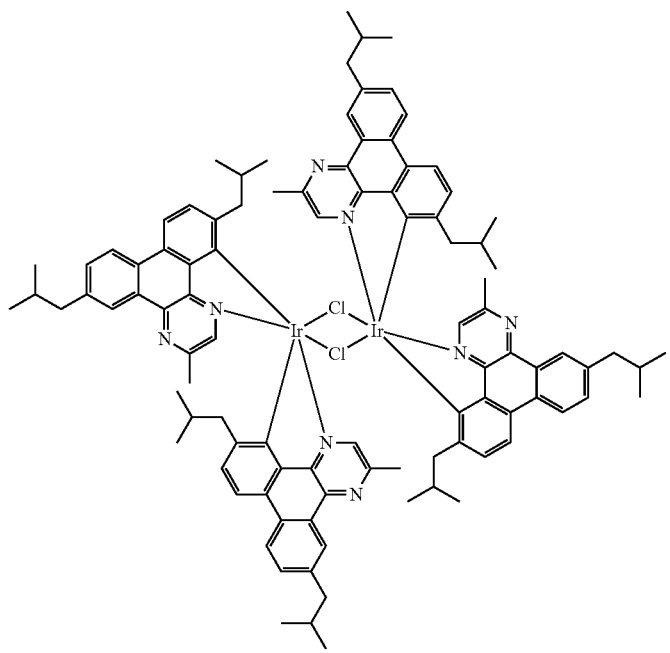 |

-continued
| Diiridium Complex Example | Ligand Example | Diiridium complex |
|---|---|---|
| 2 | 1c) | 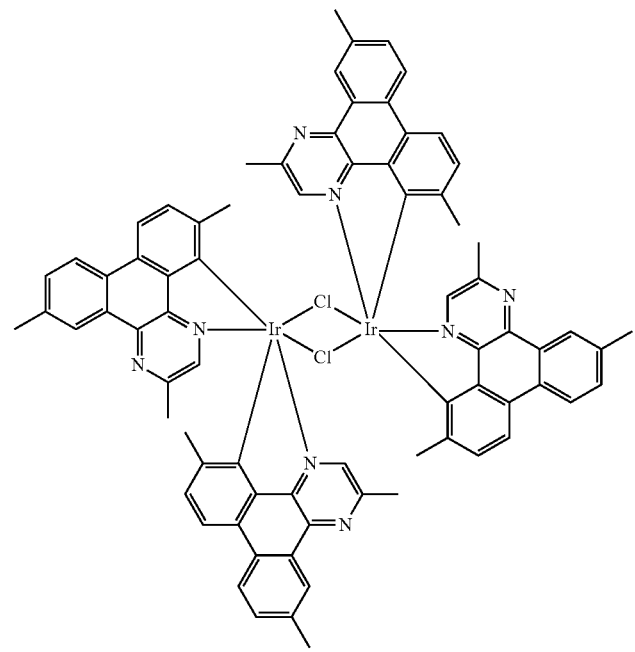 |
| 3 | 4b) | 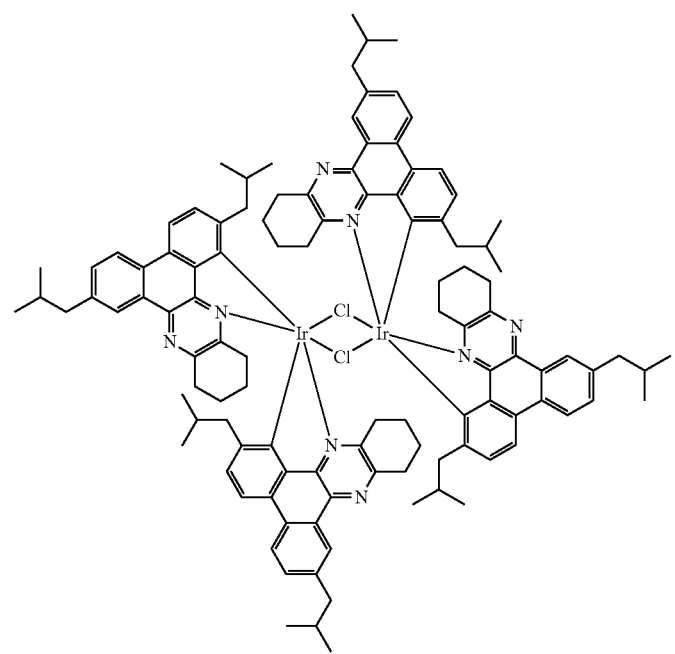 |

| Diiridium Complex Example | Ligand Example | Diiridium complex |
|---|---|---|
| 4 | 6 | 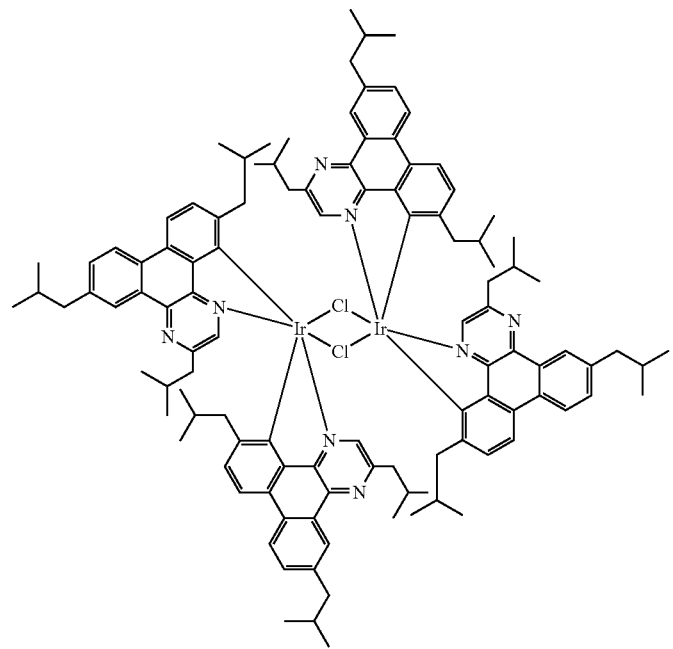 |
| 5 | 8 | 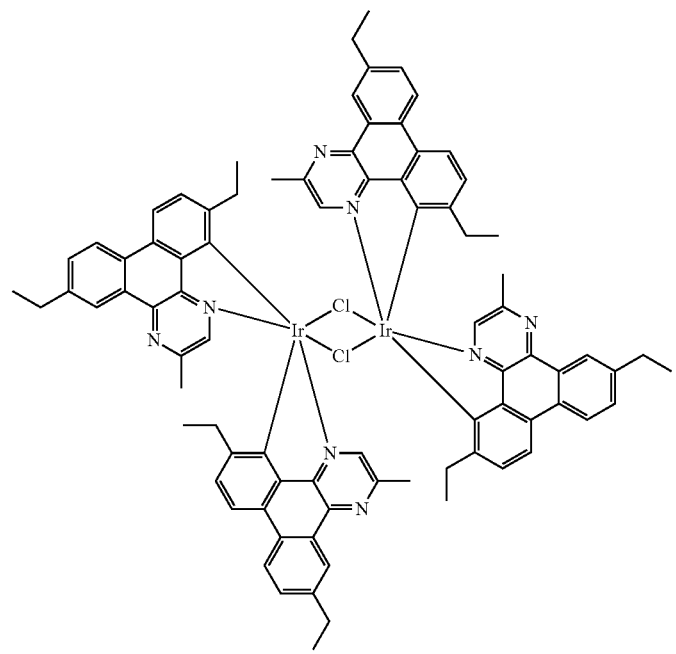 |

-continued
| Diiridium Complex Example | Ligand Example | Diiridium complex |
|---|---|---|
| 6 | 13 | 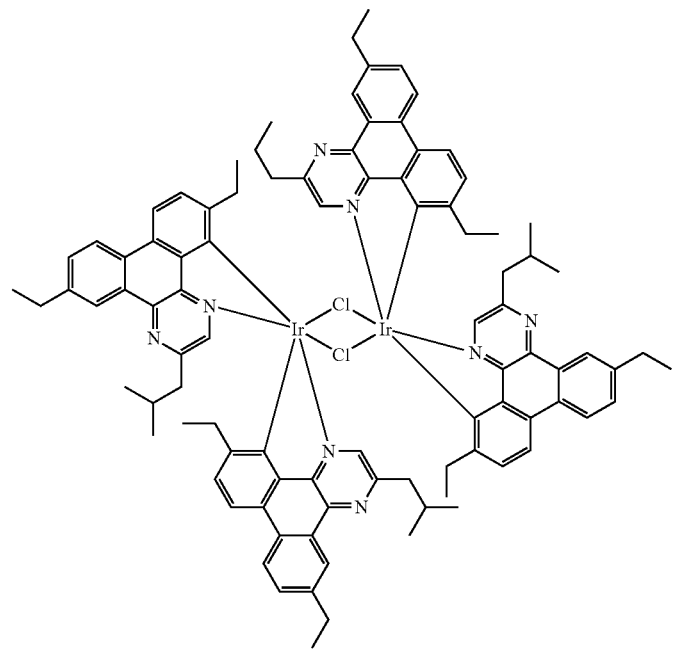 |
Complex Example 1
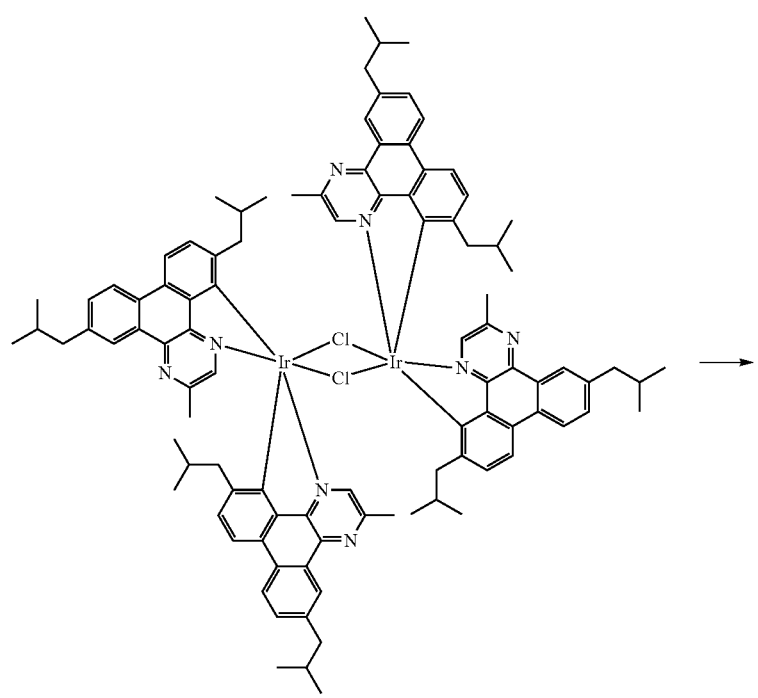

-continued

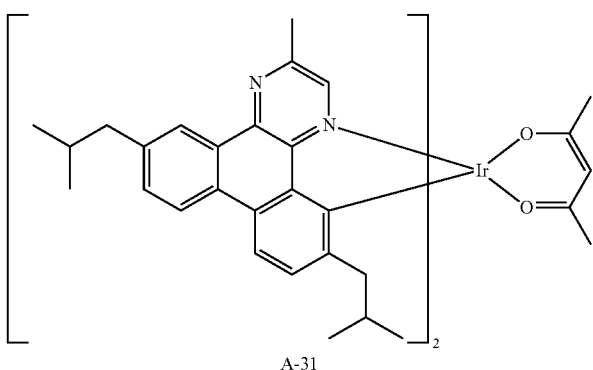

A-31

2.0 g (1.1 mmol) of the product of Diiridium Complex Example 1, and 1.1 g (10 mmol) of sodium carbonate are suspended under nitrogen in 30 ml of ethoxyethanol. The red suspension is treated with 0.85 g (8.5 mmol) of acetylacetone and stirred during one hour at 108° C. The resulting dark red suspension is filtered, rinsed with ethanol, and two times stirred in water. The remaining solid is further washed with ethanol and hexane and then dried under vacuum at 50° C. The title product, compound A-31, is obtained as a bright red powder (yield: 1.74 g (76%)). The product is further purified by high vacuum sublimation. $^1$H-NMR (300 MHz, CDCl$_3$): δ=−0.38 (d, 6 H), 0.03 (d, 6 H), 0.55-0.71 (m, 2 H), 1.03 (d, 12 H), 1.35 (dd, 2 H), 1.64 (s, 6 H), 1.68 (dd, 2 H), 2.04-2.20 (m, 2 H), 2.80 (d, 4 H), 2.88 (s, 6 H), 5.12 (s, 1 H), 7.01 (d, 2 H), 7.60 (dd, 2 H), 8.00 (d, 2 H), 8.50 (s, 2 H), 8.51 (d, 2 H), 8.98 (d, 2 H).

Complex Examples 2-7

The iridium complexes A-2, A-88, A-37, A-17, A-73 and A-79 are prepared according to Complex Example 1, starting from the corresponding products of Diiridium Complex Examples 2 to 6. The respective product structures have been confirmed by HPLC-MS and NMR measurements.

$^1$H-NMR of A-2 (400 MHz, CDCl$_3$): δ=1.29 (s, 6 H), 1.72 (s, 6 H), 2.69 (s, 6 H), 2.93 (s, 6 H), 5.23 (s, 1 H), 6.98 (d, 2 H), 7.64 (dd, 2 H), 7.95 (d, 2 H), 8.49 (d, 2 H), 8.60 (s, 2 H), 9.04 (br. s, 2 H).

$^1$H-NMR of A-88 (300 MHz, CDCl$_3$): δ=−0.25 (d, 6 H), 0.07 (d, 6 H), 0.69 (s, 18 H),0.72-0.83 (m, 2 H), 1.03 (d, 12 H), 1.47 (dd, 2 H), 1.64 (dd, 2 H), 2.05-2.20 (m, 2 H), 2.79 (d, 4 H), 2.84 (s, 6 H), 5.48 (s, 1 H), 7.00 (d, 2 H), 7.61 (dd, 2 H), 7.99 (d, 2 H), 8.37 (s, 2 H), 8.52 (d, 2 H), 8.96 (d, 2 H).

$^1$H-NMR of A-37 (400 MHz, CDCl$_3$): δ=−0.41 (d, 6 H), 0.06 (d, 6 H), 0.59-0.72 (m, 2 H), 1.00-1.15 (m, 24 H), 1.42 (dd, 2 H), 1.63 (s, 6 H), 1.75 (dd, 2 H), 2.09-2.20 (m, 2 H),2.29-2.42 (m, 2 H), 2.76-2.88 (m, 4 H), 2.91-3.05 (m, 4 H), 5.12 (s, 1 H), 7.04 (d, 2 H), 7.63 (dd, 2 H), 8.03 (d, 2 H), 8.49 (s, 2 H), 8.53 (d, 2 H), 9.02 (d, 2 H).

$^1$H-NMR of A-17 (300 MHz, CDCl$_3$): δ=0.29 (t, 6 H), 1.45(t, 6 H), 1.45-1.65 (m, 4 H), 1.67 (s, 6 H), 2.90 (s, 6 H), 2.98 (q, 4 H), 5.19 (s, 1 H), 7.03 (d, 2 H), 7.66 (dd, 2 H), 8.01 (d, 2 H), 8.51 (d, 2 H), 8.54 (s, 2 H), 9.05 (br. s, 2 H).

$^1$H-NMR of A-73 (400 MHz, CDCl$_3$): δ=0.38 (t, 6 H), 0.73 (s, 18 H), 1.48 (t, 6 H), 1.61 (q, 4 H), 2.87 (s, 6 H), 3.00 (q, 4 H), 5.56 (s, 1 H), 7.05 (d, 2 H), 7.69 (dd, 2 H), 8.03 (d, 2 H), 8.43 (s, 2 H), 8.55 (d, 2 H), 9.06 (br. s, 2 H).

$^1$H-NMR of A-79 (300 MHz, CDCl$_3$): δ=0.27 (t, 6 H), 0.96-1.09 (m, 12 H), 1.40-1.52 (m, 8 H), 1.63 (s, 6 H), 1.59-1.76 (m, 2 H), 2.26-2.42 (m, 2 H), 2.86-3.06 (m, 8 H), 5.16 (s, 1 H), 7.04 (d, 2 H), 7.66 (dd, 2 H), 8.01 (d, 2 H), 8.48 (s, 2 H), 8.52 (d, 2 H), 9.06 (br. s, 2 H).

The comparative complexes CC-1 to CC-7 are described in WO2009100991.

The photoluminescence (PL) spectra of the iridium complexes are measured on thin polymer films doped with the respective iridium complexes. The thin films are prepared by the following procedure: a 10%-w/w polymer solution is made by dissolving 1 g of the polymer "PMMA 6N" (Evonik) in 9 g of dichloromethane, followed by stirring for one hour. 2 mg of the respective iridium complexes are added to 0.98 g of the PMMA solution, and stirring continued for one minute. The solutions are casted by doctor-blading with a film applicator (Model 360 2082, Erichsen) with a 60 μm gap onto quartz substrates providing thin doped polymer films (thickness ca. 6 pm). The PL spectra and quantum-yields (Q.Y.) of these films are measured with the integrating-sphere method using the Absolute PL Quantum Yield Measurement System (Hamamatsu, Model C9920-02) (excitation wavelength: 400 nm). The PL quantum efficiencies are given relative to Ir(MDQ)$_2$(acac) (CC-1), described in J.-P. Duan et al., Adv. Mat. 2003, 15, 224, with the PL Quantum Yield (Q.Y.) value of Ir(MDQ)$_2$(acac) given as 100%. The PL O.Y., $\lambda_{max}$, CIE x, y and FWHM of the iridium complex doped PMMA films are shown in the table below:

| Compound | Structure of the Iridium complex | PL Q.Y. | λ$_{max}$ (nm) | CIE x, y | FWHM (nm) |
|---|---|---|---|---|---|
| CC-1 | 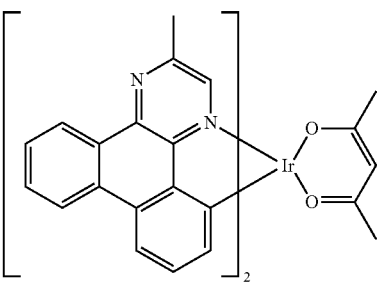 | 100% | 615 | 0.62, 0.38 | 95 |
| CC-2 | 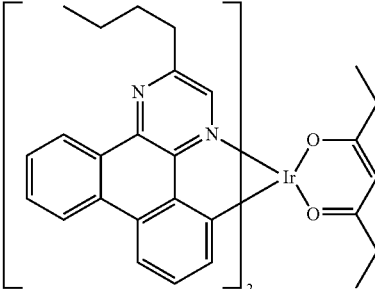 | 101% | 619 | 0.63, 0.37 | 94 |
| CC-3 | 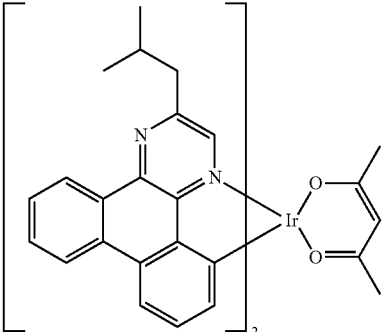 | 103% | 612 | 0.62, 0.38 | 91 |
| CC-4 | 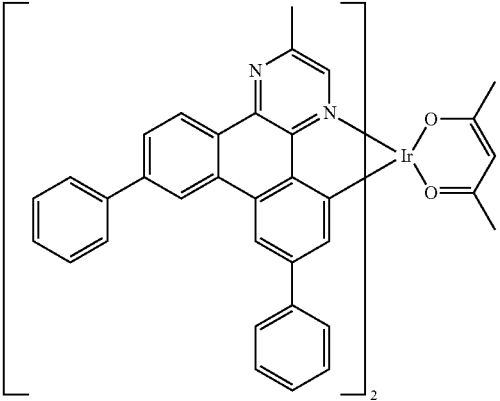 | 100% | 617 | 0.63, 0.37 | 98 |

-continued
| Compound | Structure of the Iridium complex | PL Q.Y. | λ$_{max}$ (nm) | CIE x, y | FWHM (nm) |
|---|---|---|---|---|---|
| CC-5 | 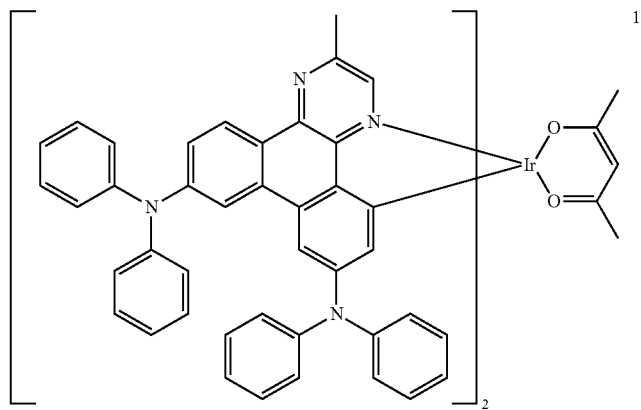 | 101% | 621 | 0.65, 0.35 | 93 |
| CC-6 | 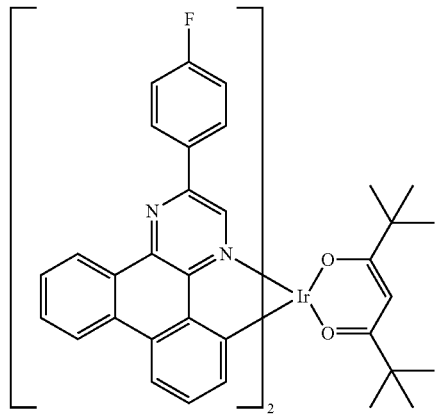 | 100% | 638 | 0.66, 0.34 | 94 |
| CC-7 | 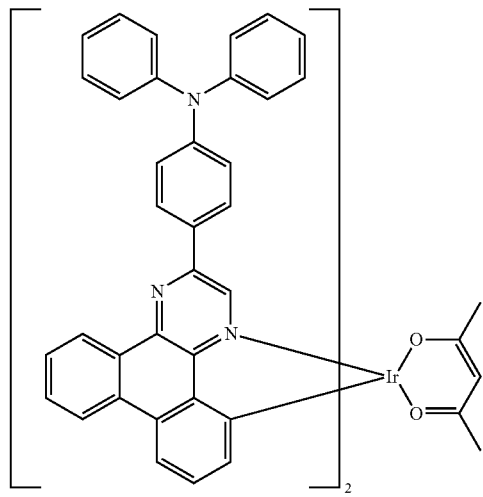 | 100% | 628 | 0.67, 0.33 | 93 |

-continued

| Compound | Structure of the Iridium complex | PL Q.Y. | λ$_{max}$ (nm) | CIE x, y | FWHM (nm) |
|---|---|---|---|---|---|
| A-31 | | 108% | 618 | 0.64, 0.36 | 83 |
| A-2 | | 105% | 618 | 0.64, 0.36 | 86 |
| A-88 | | 108% | 621 | 0.65, 0.35 | 83 |
| A-37 | | 114% | 612 | 0.63, 0.37 | 79 |

| Compound | Structure of the Iridium complex | PL Q.Y. | λ$_{max}$ (nm) | CIE x, y | FWHM (nm) |
|---|---|---|---|---|---|
| A-17 | | 115% | 619 | 0.64, 0.36 | 84 |
| A-73 | | 109% | 623 | 0.65, 0.35 | 85 |
| A-79 | | 114% | 613 | 0.63, 0.37 | 83 |

As evident from the above table, the iridium complexes of the present invention show deeper red color index coordinates (CIE x,y), narrower emission spectra with smaller full width of half maxima (FWHM) of the emission spectra, due to the fact that $R^3$ and $R^8$ represent alkyl groups in comparison to iridium complexes described in WO2009100991, wherein $R^3$ and $R^8$ represent H. Contrary to the teaching of EP1939208A1 said effect is achieved without introduction of an aryl group as $R^1$.

The photoluminescence (PL) spectra of the iridium complexes are measured on thin α-NPD films doped with 4%-w/w of the respective iridium complexes. The thin film samples are prepared by the following procedure: 1 mg of the the respective iridium complexes and 24 mg of α-NPD are added to 2.5 mL of dichloromethane and the mixtures stirred for 1-5 minutes. The resulting solutions are casted by doctor-blading with a film applicator (Model 360 2082, Erichsen) with a 30 μm gap onto quartz substrates. The PL spectra aere measured as described for the PMMA films (excitation wavelength: 400 nm). The lifetime (τ$_V$) of the phosphorescence of the iridium complexes in the prepared films are measured by the following procedure: For excitation of the emission a sequence of short laser pulses (THG Nd-YAG, 355 nm, 1 nsec pulse length, 1 kHz repetition rate) is used. The emissions are detected by the time-resolved photon-counting technique in the multi-channel scaling modus using a combination of photomultiplier, discriminator and a multiscaler card (FAST ComTec GmbH, Model P7888). The τ$_V$, λ$_{max}$, CIE x, y and FWHM of the iridium complex doped α-NPD films are shown in the table below:

| Cpd. | λ$_{max}$ (nm) | CIE x, y | FWHM (nm) | τ$_v$ (μs) |
|---|---|---|---|---|
| CC-1 | 615 | 0.62, 0.38 | 90 | 1.83 |
| CC-2 | 625 | 0.64, 0.36 | 99 | 1.64 |
| CC-5 | 622 | 0.65, 0.35 | 92 | 3.15 |
| A-31 | 627 | 0.65, 0.35 | 86 | 1.44 |
| A-88 | 630 | 0.66, 0.34 | 86 | 1.53 |
| A-17 | 625 | 0.65, 0.35 | 78 | 1.37 |
| A-37 | 615 | 0.64, 0.36 | 72 | 1.30 |
| A-79 | 617 | 0.64, 0.36 | 73 | 1.34 |

As evident from the above table, the iridium complexes of the present invention show deeper red color index coordinates (CIE x,y), together with narrower emission spectra with smaller full width of half maxima (FWHM) of the emission spectra, and a reduced triplet lifetime $\tau_V$ due to the fact that $R^3$ and $R^8$ represent alkyl groups, in comparison to iridium complexes described in WO2009100991, wherein $R^3$ and $R^8$ represent H.

The photoluminescence (PL) spectra of the iridium complexes are measured in a concentration series on thin α-NPD films doped with either of 2%-w/w, 5%-w/w, or 10%-w/w of the respective iridium complexes. The α-NPD film samples of the concentration series are prepared by the following procedure: 0.5 mg iridium complex and 24.5 mg α-NPD, 1.25 mg iridium complex and 23.75 mg α-NPD, 2.5 mg of iridium complex and 22.5 mg α-NPD, are each added to 2.5 ml of dichloromethane. After stirring all mixtures for 1-5 min the solutions casted by doctor-blading with a film applicator (Model 360 2082, Erichsen) with a 30 μm gap onto quartz substrates. The PL spectra are measured as described above (excitation wavelength: 400 nm). The $\lambda_{max}$, CIE x, y and FWHM of the iridium complex doped α-NPD films are shown in the table below:

|  | 2% in α-NPD | | | 5% in α-NPD | | | 10% in α-NPD | | |
| --- | --- | --- | --- | --- | --- | --- | --- | --- | --- |
|  | $\lambda_{max}$ (nm) | CIE x, y | FWHM (nm) | $\lambda_{max}$ (nm) | CIE x, y | FWHM (nm) | $\lambda_{max}$ (nm) | CIE x, y | FWHM (nm) |
| CC-1 | 615 | 0.62 0.38 | 86 | 616 | 0.63 0.37 | 90 | 627 | 0.64 0.36 | 94 |
| A-37 | 615 | 0.64 0.36 | 70 | 620 | 0.65 0.35 | 77 | 622 | 0.65 0.35 | 79 |
| A-17 | 619 | 0.64 0.36 | 77 | 623 | 0.65 0.35 | 78 | 626 | 0.65 0.35 | 78 |
| A-31 | 620 | 0.64 0.36 | 76 | 623 | 0.65 0.35 | 83 | 628 | 0.66 0.34 | 87 |
| A-88 | 625 | 0.65 0.35 | 80 | 629 | 0.66 0.34 | 83 | 628 | 0.66 0.34 | 84 |

As evident from the above table, the iridium complexes of the present invention show deeper red color index coordinates (CIE x,y), together with narrower emission spectra with smaller full width of half maxima (FWHM) of the emission spectra over a broad range of concentrations which are relevant for application of the claimed complexes. The color index coordinates (CIE x,y) can be also less dependent from the amount of emitter used in the matrix material as in the case of the iridium complexes described in WO2009100991.

Comparative Application Example 1

The ITO substrate used as the anode is first cleaned with an acetone/isopropanol mixture in an ultrasound bath. To eliminate any possible organic residues, the substrate is exposed to a continuous ozone flow in an ozone oven for further 25 minutes. This treatment also improves the hole injection properties of the ITO. Then Plexcore® OC AJ20-1000 (commercially available from Plextronics Inc.) is spin-coated and dried to form a hole injection layer (~40 nm).

Thereafter, the organic materials specified below are applied by vapor deposition to the clean substrate at a rate of approx. 0.5-5 nm/min at about $10^{-7}$-$10^{-9}$ mbar. As a hole transport and exciton blocker,

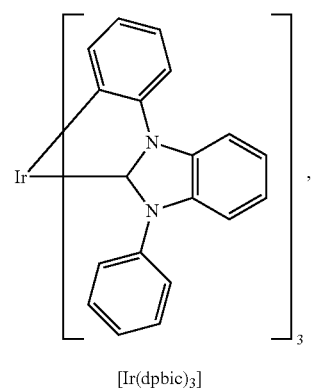

[Ir(dpbic)₃]

for preparation, see iridium complex (7) in patent application WO2005/019373), is applied to the substrate with a thickness of 20 nm, wherein the first 10 nm are doped with $MoO_x$ (~10%) to improve the conductivity.

Subsequently, a mixture of 10% by weight of emitter compound

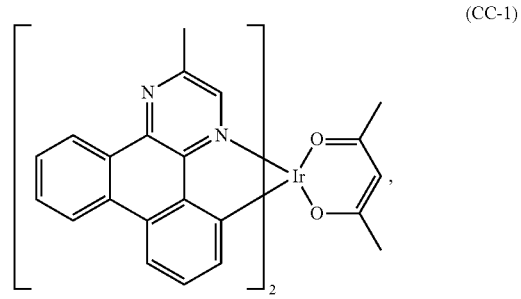

(CC-1)

and 90% by weight of compound

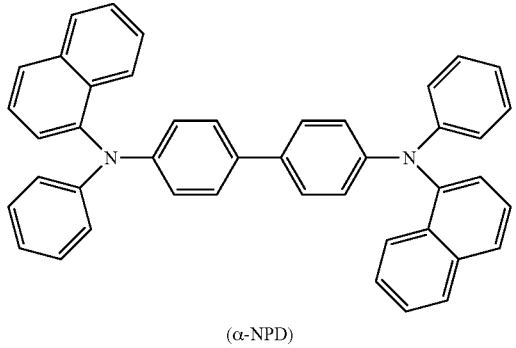 [SMILES: c1ccc(N(c2ccc(-c3ccc(N(c4ccccc4)c4cccc5ccccc45)cc3)cc2)c2cccc3ccccc23)cc1]

(α-NPD)

is applied by vapor deposition in a thickness of 20 nm.

Subsequently, BAlq

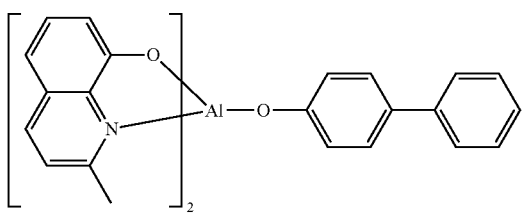

is applied by vapour deposition with a thickness of 10 nm as blocker. An additional layer of BCP

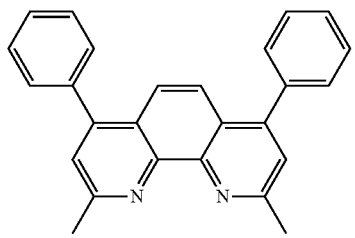 [SMILES: Cc1cc(-c2ccccc2)c2ccc3c(-c4ccccc4)cc(C)nc3c2n1]

doped with $Cs_2CO_3$ is applied as electron transport layer by vapor deposition in a thickness of 50 nm and finally a 100 nm-thick Al electrode completes the device.

All fabricated parts are sealed with a glass lid and a getter in an inert nitrogen atmosphere.

To characterize the OLED, electroluminescence spectra are recorded at various currents and voltages. In addition, the current-voltage characteristic is measured in combination with the light output emitted. The light output can be converted to photometric parameters by calibration with a photometer. To determine the lifetime, the OLED is operated at a constant current density and the decrease in the light output is recorded. The lifetime is defined as that time which lapses until the luminance decreases to half of the initial luminance.

Comparative Application Example 2

The device of Comparative Application Example 2 is prepared as the device of Comparative Application Example 1, except that compound CC-3 is used instead of compound CC-1

Application Examples 1 and 2

The device of Application Examples 1 and 2 is prepared as the device of Comparative Application Example 1, except that compound A-79 and (A-17), respectively are used instead of compound CC-1.

| | $\lambda_{max}$ | CIEx | CIEy | FWHM | U[V] | cd/A | lm/W | EQE |
|---|---|---|---|---|---|---|---|---|
| Comp. Appl. Ex. 1 (CC-1) | 615 | 0.63 | 0.37 | 88 | 3.04 | 18.7 | 19.4 | 12.6 |
| Comp. Appl. Ex. 2 (CC-3) | 608 | 0.62 | 0.38 | 84 | 3.06 | 28 | 28.8 | 16.1 |
| Appl. Ex. 1 (A-79) | 614 | 0.64 | 0.36 | 71 | 3.35 | 25 | 23.5 | 16.2 |
| Appl. Ex. 2 (A-17) | 619 | 0.65 | 0.35 | 76 | 3.38 | 22.4 | 20.9 | 16.7 |

Figure 2:
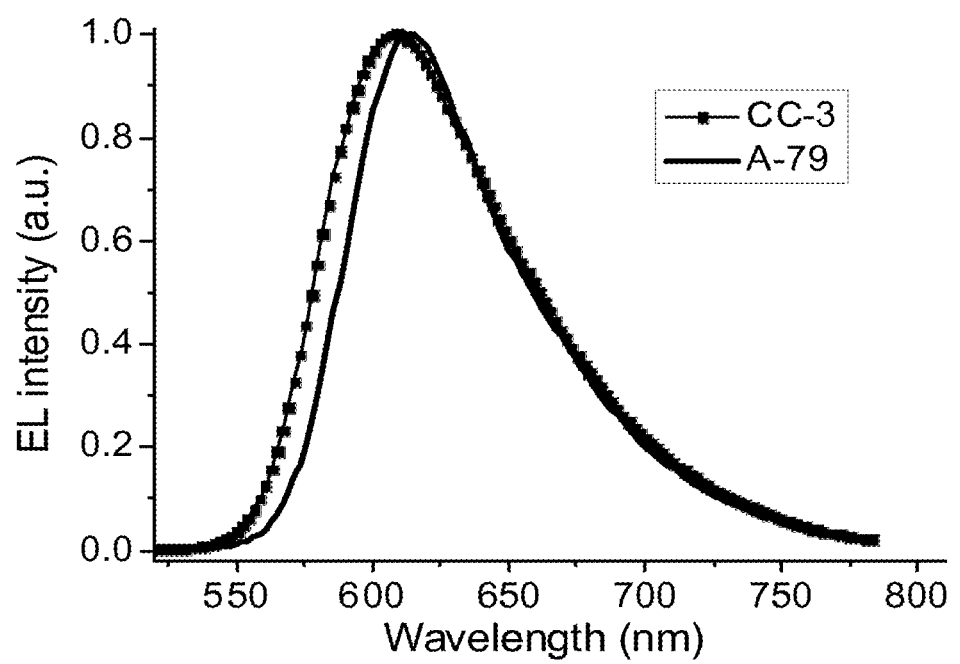
FIG. 2 provides a plot of the EL intensity of compounds CC-3 and A-79 as a function of wavelength.

As evident from the above table, the iridium complexes of the present invention show deeper red color index coordinates (CIE x,y), together with narrower emission spectra with smaller full width of half maxima (FWHM) of the emission spectra, at high EQE, due to the fact that $R^3$ and $R^8$ represent alkyl groups in comparison to iridium complexes described in WO2009100991, wherein $R^3$ and $R^8$ represent H. Reference is made to FIG. 1, which provides a plot of the EL intensity of compounds CC-1 and A-17 as a function of wavelength, and FIG. 2, which provides a plot of the EL intensity of compounds CC-3 and A-79 as a function of wavelength.

Comparative Complex Example 1 (complex CC-8=complex A-156 described in WO2009/100991)

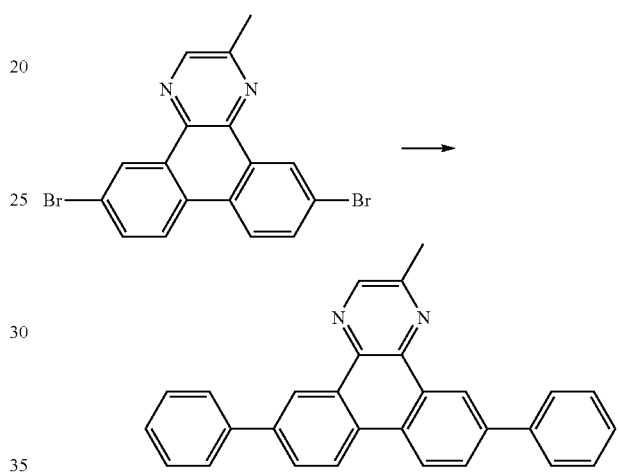

a) 10.0 g (24.9 mmol) of 6,11-dibromo-2-methyldibenzo[f,h]quinoxaline (product of Ligand Example 1b), and 9.1 g (74.6 mmol) of phenylboronic acid are suspended under argon in 250 ml of toluene. 0.22 g (1.0 mmol) of palladium (II) acetate and 1.23 g (3.0 mmol) of 2-dicyclohexylphosphino-2',6'-dimethoxybiphenyl are added, followed by the addition of 57.3 g (0.25 mol) of potassium phosphate hydrate. The reaction mixture is degassed with argon and the light yellow suspension heated under reflux for two hours. The hot grey suspension is filtered through Celite, and the Celite layer several times extracted with 200 ml of hot toluene. The collected eluents are concentrated under vacuum and the resulting solid recrystallized from ethanol, giving the title product as a white solid (yield: 5.1 g (52%)). Melting point: 288-290° C. $^1$H-NMR (400 MHz, $CDCl_3$): δ=2.80 (s, 3 H), 7.32-7.40 (m, 2 H), 7.43-7.52 (m, 4 H), 7.81 (d, 4 H), 7.94-8.01 (m, 2 H), 8.63 (d, 2 H), 8.74 (s, 1 H), 9.39 (d, 1 H),9.45 (d, 1 H).

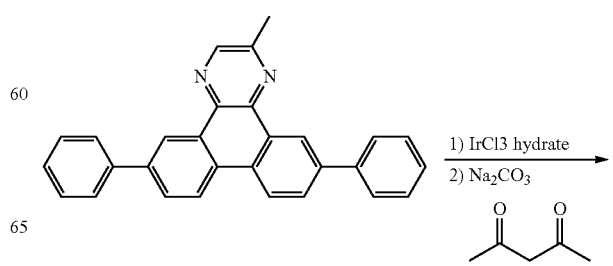

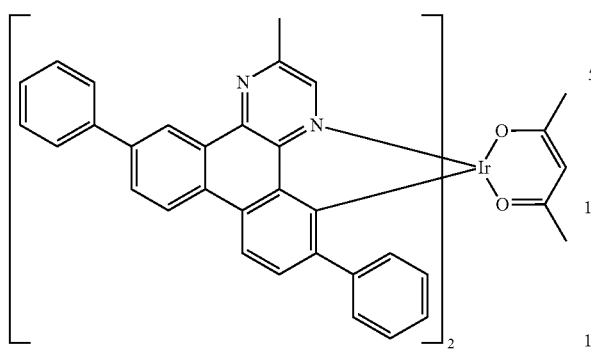

Comparative Complex Example 2 (complex CC-9=complex A-18 described in WO2009/100991)

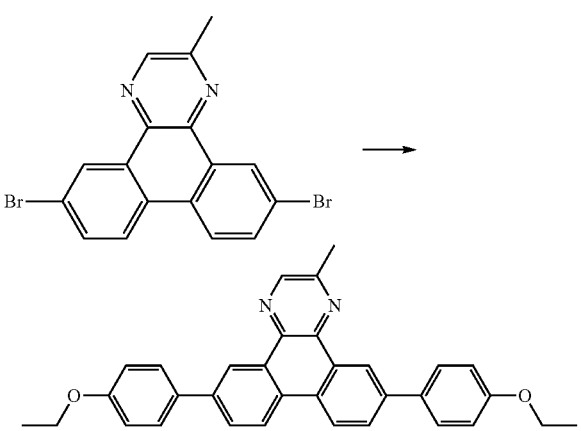

b) The diiridium complex intermediate is prepared first according to the procedure reported for Diiridium Complex Example 1, with 1.11 g (2.8 mmol) of the product of Comparative Complex Example 2a), 0.48 g (1.3 mmol) of iridium(III)chloride hydrate and 30 ml of 2-ethoxyethanol, giving the diiridium complex intermediate as an orange powder (1.24 g, 92%). In a next step, the comparative complex CC-8 is prepared according to Complex Example 1, with 1.19 g (0.58 mmol) of diiridium complex intermediate isolated before, 0.62 g (5.8 mmol) of sodium carbonate, 0.47 g (4.7 mmol) of acetylacetone and 20 ml of 2-ethoxyethanol, giving the comparative complex CC-8 as an orange powder after extensive purification (1.08 g, 85%), with a HPLC-purity of >99% at 250 nm UV-detection. APCI-LC-MS (negative, m/z): exact mass=1082.32 g/mol; found 1082.1 [M]$^+$. APCI-LC-MS (positive, m/z): exact mass=1082.32 g/mol; found 1083.2 [M+1]$^+$.

a) 8.0 g (19.9 mmol) of 6,11-dibromo-2-methyldibenzo[f,h]quinoxaline (product of Ligand Example 1b), and 9.91 g (59.7 mmol) of 4-ethoxyphenylboronic acid are suspended under argon in 250 ml of toluene. 0.18 g (0.8 mmol) of palladium(II) acetate and 0.98 g (2.4 mmol) of 2-dicyclohexyl-phosphino-2',6'-dinnethoxybiphenyl are added, followed by the addition of 45.8 g (0.20 mol) of potassium phosphate hydrate. The reaction mixture is degassed with argon and the grey suspension heated under reflux for 21 hours. The hot grey suspension is filtered through Celite, and the Celite layer several times extracted with 200 ml of hot toluene. The collected eluents are concentrated under vacuum giving the title product as a light yellow solid (yield: 4.0 g (41%)). Melting point: 310-312° C. $^1$H-NMR (300 MHz, CDCl$_3$): δ=1.45-1.56 (m, 6 H), 2.90 (s, 3 H), 4.11-4.20 (m, 4 H), 7.04-7.13 (m, 4 H), 7.84 (d, 4 H), 7.98-8.07 (m, 2 H), 8.68 (d, 2 H), 8.83 (s, 1 H), 9.43 (d, 1 H), 9.49 (d, 1 H).

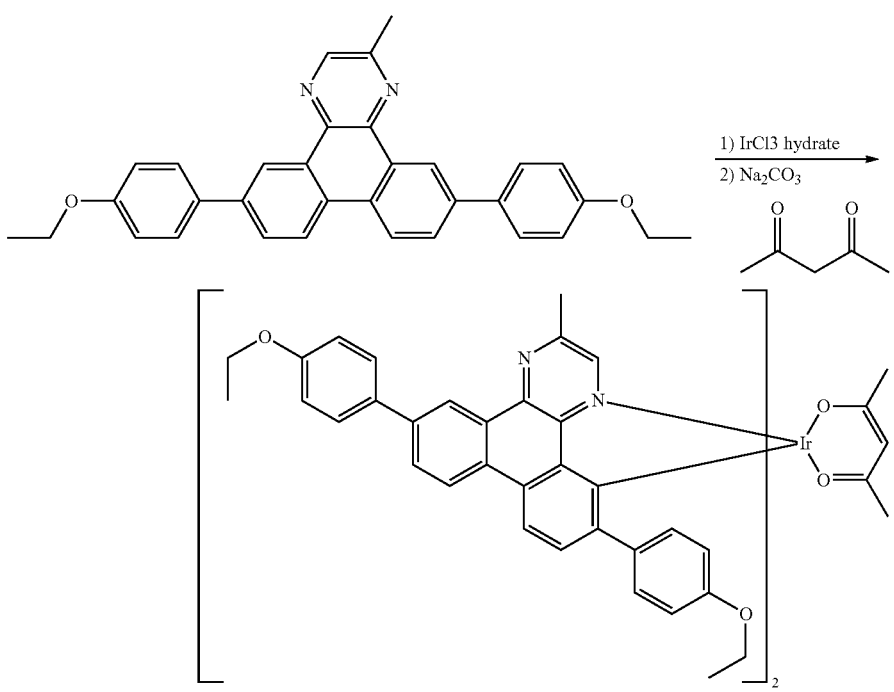

b) The diiridium complex intermediate is prepared first according to the procedure reported for Diiridium Complex Example 1, with 1.3 g (2.7 mmol) of the product of Comparative Complex Example 2a), 0.46 g (1.3 mmol) of iridium(III)chloride hydrate and 50 ml of 2-ethoxyethanol, giving the diiridium complex intermediate as a red powder (1.50 g, 99%). In a next step, the comparative complex CC-9 is prepared according to Complex Example 1, with 1.5 g (0.63 mmol) of diiridium complex intermediate isolated before, 0.67 g (6.3 mmol) of sodium carbonate, 0.5 g (5.0 mmol) of acetylacetone and 20 ml of 2-ethoxyethanol, giving the title complex as a red powder after extensive purification (1.49 g, 94%).

Photoluminescence spectra of complexes CC-1, CC-8, A-37 and A-17 have been measured in PMMA films as described above and are shown in the table below.

| Compound | Structure of the Iridium complex | PL Q.Y. | $\lambda_{max}$ (nm) | CIE x, y |
| --- | --- | --- | --- | --- |
| CC-1 | | 100% | 615 | 0.62, 0.38 |
| CC-8 | | 111% | 587 | 0.57, 0.43 |
| A-37 | | 114% | 612 | 0.63, 0.37 |
| A-17 | | 115% | 619 | 0.64, 0.36 |

As is evident from the above table, the comparative complex CC-8 does not lead to a deeper red color point compared to the complexes of the present invention. CC-8 shows a large green-shift of the emission spectra with CIE x,y of (0.57, 0.43) due to the extended conjugation by phenyl groups attached to the $R^3$ and $R^8$ positions. Complex CC-8 does not sublime at pressures down to $10^{-6}$ to $10^{-7}$ mbar and is not suitable for a vacuum deposition process, but leads to degradation with increase of temperature. Thermal gravimetric analysis (TGA) of complex CC-8 shows a weight loss with an onset temperature of 240-250° C. By contrast, complexes of the present invention show high sublimation yields of >70-80% based on much higher thermal stability and volatility, with onset temperatures in TGA of above 330° C.

Complex CC-9 is not soluble and does not sublime at pressures down to $10^{-6}$ to $10^{-7}$ mbar and is not suitable for a vacuum deposition process, but leads to degradation with increase of temperature. Thermal gravimetric analysis (TGA) of complex CC-9 shows a weight loss with an onset temperature of 200-210° C. Complexes of the present invention show high sublimation yields of >70-80% based on much higher thermal stability and volatility, with onset temperatures in TGA of above 330° C.

The invention claimed is:

1. A compound of formula:

$$L^a \underset{L^a}{\overset{Cl}{\underset{Cl}{Ir}}} \underset{L^a}{\overset{L^a}{Ir}}$$

wherein:
each $L^a$ is independently:

[structure with $R^1$, $R^2$, $R^3$, $R^8$]

wherein:
a) $R^1$ is H, $C_1$-$C_8$ alkyl or $C_3$-$C_8$ cycloalkyl, wherein the $C_3$-$C_8$ cycloalkyl may optionally be substituted by $C_1$-$C_8$ alkyl or $C_1$-$C_8$ perfluoroalkyl;
$R^2$ is H or $C_1$-$C_8$ alkyl;
$R^3$ is $C_1$-$C_8$ alkyl, Si($C_1$-$C_8$ alkyl)$_3$ or $C_3$-$C_8$ cycloalkyl; and
$R^8$ is $C_1$-$C_8$ alkyl, Si($C_1$-$C_8$ alkyl)$_3$ or $C_3$-$C_8$ cycloalkyl; or
b) $R^1$ is a group of formula:

[aryl/heteroaryl structures with $R^4$, $R^{4'}$, $R^{4''}$ substituents]

wherein:
$R^4$ is $C_1$-$C_8$ alkyl, $CF_3$ or $NR^7R^9$;
$R^{4'}$ is $C_1$-$C_8$ alkyl or $CF_3$;
$R^{4''}$ is $C_1$-$C_8$ alkyl or $CF_3$;
$R^7$ is phenyl, 1-naphthyl or 2-naphthyl; and
$R^9$ is phenyl, 1-napthyl or 2-naphthyl; or
$R^7$ and $R^9$, together with the nitrogen atom to which they are bonded, form a group of formula:

[carbazole structure with $R^{10}$ groups]

wherein:
each $R^{10}$ is independently H or $C_1$-$C_8$ alkyl; and
$R^2$ is H;
$R^3$ is $C_1$-$C_8$ alkyl, Si($C_1$-$C_8$ alkyl)$_3$ or $C_3$-$C_8$ cycloalkyl; and
$R^8$ is $C_1$-$C_8$ alkyl, Si($C_1$-$C_8$ alkyl)$_3$ or $C_3$-$C_8$ cycloalkyl; or
c) $R^1$ and $R^2$ together form a —(CH$_2$)$_3$— ring or —(CH$_2$)$_4$— ring, wherein the —(CH$_2$)$_3$— ring or —(CH$_2$)$_4$— ring may optionally be substituted by one or two $C_1$-$C_8$ alkyl and/or by one or two $C_1$-$C_8$ perfluoroalkyl;
$R^3$ is $C_1$-$C_8$ alkyl, Si($C_1$-$C_8$ alkyl)$_3$ or $C_3$-$C_8$ cycloalkyl; and
$R^8$ is $C_1$-$C_8$ alkyl, Si($C_1$-$C_8$ alkyl)$_3$ or $C_3$-$C_8$ cycloalkyl.

2. The compound according to claim 1, wherein:
$R^1$ is a group of formula:

[phenyl group structures with $R^4$, $R^{4''}$ substituents]

and
R² is H.

3. The compound according to claim 1, wherein:
R¹ and R² together form an optionally substituted —(CH$_2$)$_3$— ring or an optionally substituted —(CH$_2$)$_4$— ring.

4. The compound according to claim 1, wherein:
R¹ is $C_1$-$C_8$ alkyl.

5. The compound according to claim 1, wherein:
R² is H.

6. The compound according to claim 1, wherein:
R³ is $C_1$-$C_8$ alkyl, Si($C_1$-$C_4$ alkyl)$_3$ or $C_3$-$C_6$ cycloalkyl; and
R⁸ is $C_1$-$C_8$ alkyl, Si($C_1$-$C_4$ alkyl)$_3$ or $C_3$-$C_6$ cycloalkyl.

7. The compound according to claim 1, wherein:
R³ is $C_1$-$C_8$ alkyl; and
R⁸ is $C_1$-$C_8$ alkyl.

8. An emitting layer comprising the compound according to claim 1.

9. The emitting layer according to claim 8, wherein the emitting layer further comprises a host material.

10. An organic electronic device comprising the compound according to claim 1.

11. An electrophotographic photoreceptor, a photoelectric converter, an organic solar cell, a switching element, an organic light emitting field effect transistor, an image sensor, a dye laser or an electroluminescent device comprising the compound according to claim 1.

12. An apparatus comprising the organic electronic device according to claim 10.

13. The apparatus according to claim 12, wherein the apparatus is selected from the group consisting of a stationary visual display unit, a keyboard, a wallpaper, an illumination unit, an item of clothing and an item of furniture.

* * * * *